US009125937B2

(12) United States Patent
Chezal et al.

(10) Patent No.: US 9,125,937 B2
(45) Date of Patent: Sep. 8, 2015

(54) LABELLED ANALOGUES OF HALOBENZAMIDES AS MULTIMODAL RADIOPHARMACEUTICALS AND THEIR PRECURSORS

(71) Applicants:INSTITUT NATIONAL DE LA SANTE ET DE LA RECHERCHE MEDICALE (INSERM), Paris (FR); COMMISSARIAT A L'ENERGIE ATOMIQUE ET AUX ENERGIES ALTERNATIVES, Paris (FR); UNIVERSITE D'AUVERGNE CLERMONT 1, Clermont-Ferrand (FR); LABORATOIRES CYCLOPHARMA, Saint Beauzire (FR)

(72) Inventors: Jean-Michel Chezal, Clermont-Ferrand (FR); Frederic Dolle, Orsay (FR); Jean-Claude Madelmont, Clermont-Ferrand (FR); Aurelie Maisonial, Clermont-Ferrand (FR); Elisabeth Miot-Noirault, Clermont-Ferrand (FR); Nicole Moins, Clermont-Ferrand (FR); Janine Papon, Clermont-Ferrand (FR); Bertrand Kuhnast, Orsay (FR); Bertrand Tavitian, Orsay (FR); Raphael Boisgard, Orsay (FR)

(73) Assignees: INSTITUT NATIONAL DE LA SANTE ET DE LA RECHERCHE MEDICALE (INSERM), Paris (FR); COMMISSARIAT A L'ENERGIE ATOMIQUE ET AUX ENERGIES ALTERNATIVES, Paris (FR); UNIVERSITE D'AUVERGNE CLERMONT 1, Clermont-Ferrand (FR); LABORATORIES CYCLOPHARMA, Saint Beauzire (FR)

( * ) Notice: Subject to any disclaimer, the term of this patent is extended or adjusted under 35 U.S.C. 154(b) by 2 days.

(21) Appl. No.: 14/031,812

(22) Filed: Sep. 19, 2013

(65) Prior Publication Data

US 2014/0093453 A1 Apr. 3, 2014

Related U.S. Application Data

(62) Division of application No. 12/865,059, filed as application No. PCT/IB2009/050355 on Jan. 28, 2009, now abandoned.

(30) Foreign Application Priority Data

Jan. 31, 2008 (EP) .................................... 08101187

(51) Int. Cl.
| | | |
|---|---|---|
| *A61K 51/04* | (2006.01) | |
| *A61K 49/00* | (2006.01) | |
| *C07D 215/54* | (2006.01) | |
| *C07D 241/44* | (2006.01) | |
| *C07D 401/12* | (2006.01) | |
| *C07D 213/65* | (2006.01) | |
| *C07D 213/76* | (2006.01) | |
| *C07D 487/04* | (2006.01) | |

(52) U.S. Cl.
CPC .......... *A61K 49/0002* (2013.01); *C07D 213/65* (2013.01); *C07D 213/76* (2013.01); *C07D 215/54* (2013.01); *C07D 241/44* (2013.01); *C07D 401/12* (2013.01); *C07D 487/04* (2013.01)

(58) Field of Classification Search
CPC . A61K 51/04; A61K 49/0002; C07D 213/65; C07D 213/76
USPC ............. 424/1.89, 1.85, 1.81, 1.65, 1.11, 9.1; 546/300, 297, 123, 121, 103
See application file for complete search history.

(56) References Cited

U.S. PATENT DOCUMENTS

| | | | |
|---|---|---|---|
| 3,219,528 A | 11/1965 | Thominet | |
| 4,097,487 A | 6/1978 | Murakami | |
| 4,764,522 A | 8/1988 | Imhof et al. | |
| 5,190,741 A | 3/1993 | Moreau et al. | |
| 5,911,970 A | 6/1999 | John et al. | |
| 5,914,327 A | 6/1999 | Trova et al. | |
| 7,427,390 B2 * | 9/2008 | Friebe et al. ................. | 424/1.89 |
| 2001/0006619 A1 | 7/2001 | John et al. | |
| 2002/0028807 A1 | 3/2002 | Simoneau | |
| 2007/0037862 A1 | 2/2007 | Siemeister et al. | |
| 2010/0061928 A1 | 3/2010 | Madelmont et al. | |

FOREIGN PATENT DOCUMENTS

| | | |
|---|---|---|
| EP | 0 082 665 A1 | 6/1983 |
| EP | 0 458 886 B1 | 10/1993 |
| EP | 0 587 311 | 3/1994 |
| SU | 289084 | 12/1970 |
| WO | WO 90/09170 | 8/1990 |
| WO | WO 93/24096 | 12/1993 |
| WO | WO 98/17649 | 4/1998 |
| WO | WO 2005/030725 | 4/2005 |
| WO | WO 2005/042505 A1 | 5/2005 |
| WO | WO 2005/089815 A2 | 9/2005 |
| WO | WO 2005/118580 A2 | 12/2005 |
| WO | WO 2007/022241 | 2/2007 |
| WO | WO 2008/012782 A2 | 1/2008 |
| WO | WO 2008/024725 | 2/2008 |

OTHER PUBLICATIONS

Aeschilmann, "The Relative Stability of the Quinolone and Indolinone Rings." J. Chem. Soc., 1926, pp. 2903-2908.
Ashimori et al., "Novel 1,4-Dihydropyridine Calcium Antagonists. I. Synthesis and Hypotensive Activity of 4-(Substituted Pyridyl)-1,4-dihydropyridine Derivatives." Chem. Pharm. Bull., 1990, pp. 2446-2458, vol. 38(9), Pharmaceutical Society of Japan.
Bissery et al., "Experimental Antitumor Activity of Taxotere (RP 56976, NSC 628503), a Taxol Analogue." Cancer Research, 1991, pp. 4845-4852, vol. 51, American Association for Cancer Research.
Block et al., "The N.C.A. Nucleophilic $^{18}$F-Fluorination of 1,N-Disubstituted Alkanes as Fluoroalkylation Agents." Journal of Labelled Compounds and Radiopharmaceuticals. 1987, pp. 1029-1042, vol. 24, John Wiley & Sons, Ltd.
Chezal et al., "Evaluation of Radiolabeled (Hetero)Aromatic Analogues of N-(2-diethylaminoethyl)-4-iodobenzamide for Imaging and Targeted Radionuclide Therapy of Melanoma." Journal of Medicinal Chemistry, 2008, pp. 3133-3144, vol. 51, No. 11, American Chemical Society.
Coulson et al. "Tetrakis(triphenylphosphine)palladium(0)." Inorganic Synthesis, 1972, pp. 121-124, vol. 13, McGraw-Hill, Inc.
Desbois et al., "Design, synthesis and preliminary biological evaluation of acridine compounds as potential agents for a combined targeted chemo-radionuclide therapy approach to melanoma." Bioorganic & Medicinal Chemistry, 2008, pp. 7671-7690, vol. 16, Elsevier Ltd.

Denoyer et al., "Development of a high-performance liquid chromatographic method for the determination of a new potent radioiodinated melanoma imaging and therapeutic agent." Journal of Chromatography B, 2008, pp. 411-418, vol. 875, Elsevier B.V.

Dewanjee et al., "Radioiodination: Theory, Practice, and Biomedical Applications." 1992, pp. xvii-xxviii, Kluwer Academic Publisher, Norwell, USA.

Dolci et al., "Synthesis of a Fluorine-18 Labeled Derivative of Epibatidine for In Vivo Nicotinic Acetylcholine Receptor PET Imaging." Bioorganic & Medicinal Chemistry, 1999, pp. 467-479, vol. 7, Elsevier Science Ltd.

Dollé et al., "Synthesis, radiosynthesis and in vivo preliminary evaluation of [$^{11}$C]LBT-999, a selective radioligand for the visualisation of the dopamine transporter with PET." Bioorganic & Medicinal Chemistry, 2006, pp. 1115-1125, vol. 14, Elsevier Ltd.

Dollé et al., "Synthesis of 2-[$^{18}$F]Fluoro-3-[2(S)-2-azetidinylmethoxy]pyridine, a Highly Potent Radioligand for in Vivo Imaging Central Nicotinic Acetylcholine Receptors." Journal of Labelled Compounds and Radiopharmaceuticals, 1998, pp. 451-463, vol. 41, John Wiley & Sons, Ltd.

Dollé et al., "Synthesis and Nicotinic Acetylcholine Receptor in Vivo Binding Properties of 2-Fluoro-3-[2(S)-2-azetidinylmethoxy]pyridine: A New Positron Emission Tomography Ligand for Nicotinic Receptors." Journal of Medicinal Chemistry, 1999, pp. 2251-2259, vol. 42, No. 12, American Chemical Society.

Eisenhut et al., "Radioiodinated N-(2-Diethylaminoethyl)benzamide Derivatives with High Melanoma Uptake: Structure-Affinity Relationships, Metabolic Fate, and Intracellular Localization." Journal of Medicinal Chemistry, 2000, pp. 3913-3922, vol. 43, No. 21, American Chemical Society.

Hamacher et al., "Efficient Stereospecific Synthesis of No-Carrier-Added 2-[$^{18}$F]-Fluoro-2-Deoxy-D-Glucose Using Aminopolyether Supported Nucleophilic Substitution." Journal of Nuclear Medicine, Feb. 1986, pp. 235-238, vol. 27, No. 2.

Jones et al., "6-Substituted 5-Chloro-1,3-dihydro-2H-imidazo[4-5-b]pyrazin-2-ones with Hypotensive Activity." Journal of Medicinal Chemistry, 1973, pp. 537-542, vol. 16, No. 5.

Montalbetti et al., "Amide bond formation and peptide coupling." Tetrahedron, 2005, pp. 10827-10852, vol. 61, Elsevier Ltd.

Pesti et al., "Efficient Pyridinylmethyl Functionalization: Synthesis of 10,10-Bis[(2-fluoro-4-pyridinyl)methyl]-9(10H)-anthracenone (DMP 543), an Acetylcholine Release Enhancing Agent." J. Org. Chem., 2000, pp. 7718-7722, vol. 65, No. 23, American Chemical Society.

Sundberg et al., "Bis-Cationic Heteroaromatics as Macrofilaricides: Synthesis of Bis-Amidine and Bis-Guanylhydrazone Derivatives of Substituted Imidazo[1,2-a]pyridines." Journal of Medicinal Chemistry, 1998, pp. 4317-4328, vol. 41, No. 22, American Chemical Society.

Bremer, "Studien in der Reihe der Pyridino-3, 4-triazole," 1935, pp. 274-289, vol. 518, No. 1.

Iwanami et al., "Synthesis and Neuroleptic Activity of Benzamides. Cis-N-(1-Benzyl-2-methylpyrrolidin-3-y1)-5-chloro-2-methoxy-4-(methylamino)benzamide and Related Compounds," Journal of Medicinal Chemistry, 1981, pp. 1224-1230, vol. 24, No. 10, American Chemical Society.

Hendrix et al., "A mild chemospecific reductive dehalogenation of ethylaminobenzamides with lithium aluminum hydride," Tetrahedron Letters, 1999, pp. 6749-6752, vol. 40, No. 37, Elsevier Science Ltd.

International Search Report for International Patent Application No. PCT/IB2009/050355, mailed on Oct. 14, 2009.

Written Opinion for International Patent Application No. PCT/IB2009/050355, mailed on Oct. 14, 2009.

Oct. 3, 2012 Office Action issued in U.S. Appl. No. 12/375,044.

Beer et al., "[$^{123}$I/$^{18}$F] N-(2-Aminoethyl)-5-Halogeno-2-Pyridinecarbox-Amides, Site Specific Tracers for MAO-B Mapping With SPET and PET", Nuclear Medicine and Biology, Elsevier, NY, US, vol. 22, No. 8, Nov. 1, 1995, pp. 999-1004.

Osman et al.; "Comparative Biodistribution and Metabolism of Carbon-11-labeled N-[2-(Dimethylamino)ethyl]acridine-4-carboxamide and DNA-intercalating Analogues"; Cancer Research; Apr. 1, 2001; pp. 2935-2944; vol. 61.

Saleem et al.; "Pharmacokinetic Evaluation of N-[2-(Dimethylamino)Ethyl]Acridine-4-Carboxamide in Patients by Positron Emission Tomography"; Journal of Clinical Oncology; Mar. 1, 2001; pp. 1421-1429; vol. 19-No. 5.

Gamage et al.; "Phenazine-1-carboxamides: Structure-cytotoxicity relationships for 9-substituents and changes in the H-bonding pattern of the cationic side chain"; Bioorganic & Medicinal Chemistry; 2006; pp. 1160-1168; vol. 14.

Olsson et al.; "Microwave-assisted solvent-free parallel synthesis of thioamides"; Tetrahedron Letters; 2000; pp. 7947-7950; vol. 41.

Showalter et al.; "Tyrosine Kinase Inhibitors. 6. Structure-Activity Relationships among N- and 3-Substituted 2,2'-Diselenobis(1H-indoles) for Inhibition of Protein Tyrosine Kinases and Comparative in Vitro and in Vivo Studies against Selected Sulfur Congeners"; Journal of Medicinal Chemistry; 1997; pp. 413-426; vol. 40 No. 4.

United States Office Action dated Jan. 17, 2012 issued in U.S. Appl. No. 12/375,044.

* cited by examiner

*Primary Examiner* — Michael G Hartley
*Assistant Examiner* — Jagadishwar Samala
(74) *Attorney, Agent, or Firm* — Oliff PLC

(57) ABSTRACT

The present invention relates to the compound of formula (I):

$$R_1-Ar-\overset{O}{\underset{R_9}{\overset{\|}{C}}}-N-A-N\overset{R_3}{\underset{R_4}{\diagdown}} \quad (I)$$

in which
$R_1$ represents a hydrogen atom, an optionally labelled halogen, a radionuclide or a $Sn[(C_1-C_4)alkyl]_3$ group,
Ar represents an aryl group or a heteroaryl group,
$R_9$ represents a hydrogen atom, a $(C_1-C_4)$alkyl group or forms together with the group $R_1$—Ar a ring fused with the Ar group,
A represents a group of formula (β) or (δ):

$$-(CH_2)_t- \quad (\beta)$$

$$-(CH_2)_m-D-\underset{\phantom{xx}}{\underbrace{\begin{array}{c}N \\ \diagup R_{10}\end{array}}}-G-(CH_2)_n- \quad (\delta)$$

$R_3$ and $R_4$ independently represent a hydrogen atom, a $(C_1-C_6)$alkyl group, a $(C_1-C_6)$alkenyl group or a group of formula (γ):

$$-Y-Z-W-R_{11} \quad (\gamma)$$

wherein $R_{11}$ represents an optionally labelled halogen, a radionuclide, an aryl or heteroaryl group optionally substituted by an optionally labelled halogen, a radionuclide, a $-NO_2$ group, a $-NR_5R_6$ group, a $-N^+R_5R_6R_7X^-$ group, or a $-OSO_2R_{12}$ group, and their addition salts with pharmaceutically acceptable acids.

The present invention also relates to pharmaceutical compositions comprising them and to their use in diagnosis, in particular with SPECT or PET imaging and in therapy of melanoma via targeted radionuclide therapy.

15 Claims, 5 Drawing Sheets

LABELLED ANALOGUES OF HALOBENZAMIDES AS MULTIMODAL RADIOPHARMACEUTICALS AND THEIR PRECURSORS

This is a Division of application Ser. No. 12/865,059, filed Oct. 12, 2010, which in turn is a U.S. National Phase of International Application PCT/IB2009/050355, filed Jan. 28, 2009, and claims the benefit of European Patent Application No. 08101187.6, filed Jan. 31, 2008. The disclosures of the prior applications are hereby incorporated by reference herein in their entireties.

FIELD OF THE INVENTION

The present invention relates to new aromatic and heteroaromatic analogues of halobenzamides which once labelled with suitable radioactive isotopes are usable as radiopharmaceuticals for the diagnosis by single photon emission computed tomography (SPECT) or positron emission tomography (PET) or for the internal radiotherapeutic treatment of melanoma. The present invention also relates to their synthesis process and also to their corresponding use and methods in imaging and radiotherapy.

BACKGROUND

Melanoma is one of the most dangerous skin tumours with a steadily increasing incidence. Each year, 2 to 3 millions new skin cancers are diagnosed worldwide. Melanoma represents only 132 000 of these tumours but accounts for 79% of all cutaneous neoplasms deaths. Its global incidence has been increasing at a rate of around 3-8% per year in Europe since the mid 1960s. The main reason is the excessive exposure to sunlight and other sources of UV radiations, especially during childhood. Specifically, the current incidence of cutaneous melanoma is close to 10 000 new cases diagnosed per year in France. This is a highly invasive cancer, the development of which is rapidly fatal at the metastatic stage. 5-year survival does not exceed 14%, except in the case where the thickness of the tumour is less than 0.76 mm. In the case where the lesion exceeds this thickness, this tumour gives metastases in an unpredictable and silent fashion. This is why a search is currently underway for a method of investigation which makes possible the early evaluation both of the local extension and of the distant extension of the tumour. Moreover during the last decade, a number of radiopharmaceutical products, selected for their potential melanin affinity, have been experimented but few have had a satisfactory clinical development.

Early detection is crucial for prognosis. Significant progress have been made in the field of diagnosis, for instance with dermoscopy. Moreover, newly developed noninvasive functional imaging techniques such as positron emission tomography (PET) with the glucose analogue fluorine-18-labelled fluorodeoxyglucose ([$^{18}$F]FDG) in association with fused anatomic CT images allows a significant increase in terms of spatial resolution and sensitivity of detection. In the case of melanoma, which can spread widely and unpredictably throughout the body, the use of [$^{18}$F]FDG PET/CT whole-body imaging is very useful to localize all developing metastases in stage III or IV before surgery resection or in order to evaluate the regression of tumour volume during therapy. Nevertheless, this scintigraphic methodology can not discriminate between melanoma metastases and metastases of other origin. However, the use of nonspecific tracer [$^{18}$F]FDG can be limited by the risk of false-positive findings due to an abnormal uptake by inflammatory areas for example. [$^{18}$F]FDG PET scan is also very unlikely to identify metastases in brain or liver, which present a high physiologic background related to [$^{18}$F]FDG metabolism. Moreover, this technique is inappropriate for the diagnosis of early-stage melanoma (stage I or II). In summary, the only method now valuable for staging primary melanoma remains the sentinel lymph node biopsy, which is much more sensitive. The diagnostic and clinical utility of [$^{18}$F]FDG PET/CT imaging is best for patients with more advanced stages of disease.

Several biochemical targeting systems incorporating a lot of radionuclides for diagnosis have been also evaluated for early detection in SPECT or PET imaging of melanoma metastases, as example [$^{123}$I]methylene blue dye, α-MSH analogues radiolabelled with fluorine-18, technetium-99 m, indium-111, yttrium-86 or copper-64, σ1 radioligands such as [$^{18}$F]-1-(3-fluoropropyl)-4-(4-cyanophenoxymethyl)piperidine, analogues of thymidine or DOPA and various radiolabelled iodobenzamides.

If melanoma is diagnosed early (stage I or II), the most efficient treatment remains surgery. The malignant localized lesions, wherein the tumour thickness is <1.5 mm, can be cured by total resection. In this case, the success rates are approaching 90% survival at 5 years. Unfortunately, for tumours discovered when the skin lesion is already thick or ulcerated, so in case of an increased risk of metastatic disease (stage III or IV), the prognosis is very poor. In fact, the median survival rate is around 6 months and the success rates only reach 5% survival at 5 years, due to the lack of efficient therapies for metastatic malignant melanoma. For the postoperative adjuvant therapies, beneficial results were reported only for Interferon-α, which is the most commonly used to decrease the risk of recurrence. However, high doses usually administered cause substantial toxicity. The United States Food and Drug Administration have approved only two agents for the treatment of stage IV melanoma: dacarbazine and interleukin-2. Dacarbazine is an alkylating agent often used for chemotherapy. The overall response rate with this single therapy is around 22% and the median response duration is from 4 to 6 months. The oral analogue of dacarbazine, temozolomide, has also been developed. The response rate with this cytotoxic alkylating agent is comparable to this previously obtained. Interleukin-2 is a recombinant hormone of the immune system originally described as a T-cell-derivated growth factor. The response rate obtained with this therapy remains low (16%) and the treatment is often associated with significant toxic effects due to the high doses administered. None of these drugs has been shown to significantly prolong the survival of stage IV patients. Moreover, external beam radiotherapy can not be considered as an alternative because melanoma is described as radioresistant. Several clinical trials are under way in order to find novel efficient treatments for metastatic melanoma, in the fields of chemo, immuno or radiotherapy, and combined therapies (as biochemotherapy for example). At this time, no real benefit in term of global survival has been demonstrated.

It should be explained that radiopharmaceutical products comprise two functional components, one being radioactive and the other not being radioactive. The radioactive component makes possible the detection of the product in the context of the diagnosis and it constitutes the active agent in the case of therapeutic use. It is a radionuclide with appropriate physical properties. The nonradioactive component, for its part, is a molecule or tracer, optionally biological, intended to accumulate in the target organ, in the context of the present invention, in the melanoma, and to ensure the absorption of radioactivity by the latter. This nonradioactive component is determining for the biological behaviour of the radiopharmaceutical product in the body, in particular regarding the specificity and the pharmacokinetic profile.

Document EP 458 886 describes compounds of use in the diagnosis and treatment of malignant melanoma. From these molecules, N-(2-diethylaminoethyl)-4-iodobenzamide (BZA) forms in particular the subject of more detailed studies, and also N-(2-diethylaminoethyl)-2-iodobenzamide (BZA2), in the medical imaging application and more particularly for the scintigraphic detection of primary ocular melanoma and metastases of cutaneous and ocular melanomas. BZA2, radiolabelled with iodine-123, is object of a clinical trial for melanoma metastases imaging by SPECT.

The document U.S. Pat. No. 5,911,970 for its part describes, inter alia, other benzamide-derived compounds exhibiting a high specificity and affinity to cell surface sigma receptors of cancer cells.

Document WO 2005/089815 describes some radiohalogenated benzamide derivatives and their potential use for tumour diagnosis and tumour therapy of melanoma.

There thus exists, on one hand, a need to have available a specific tracer which makes it possible, from the time of the diagnosis, to carry out an assessment of extension of the disease and then, subsequently, monitoring and dosimetry studies. Such a tracer should advantageously make it possible the differential diagnosis of ocular melanoma, primary lesion, which is often difficult to identify.

On the other hand, as exposed above, treatments remain defeated with regard to disseminated melanoma and the development of novel specific therapeutic approaches for the treatment of melanoma is essential.

There is moreover a need to find new molecules, which depending on the radioisotope which is introduced thereon, are able to form a radiotracer usable for the diagnosis using PET or SPECT imaging and able to form an agent for the internal radionuclide therapy.

There is lastly a need for multimodal radiotracers widening the scope of imaging techniques in the field of diagnosis of melanoma, and more particularly a need of new tracers finding potential application in fluorine-18 PET imaging.

Today, fluorine-18, beyond its adequate physical and nuclear characteristics, appears as the most attractive positron-emitting radioisotope for radiopharmaceutical chemistry and PET imaging, part of this continuous growing interest probably due to the successful use in clinical oncology of [$^{18}$F]FDG, the most widely used PET-radiopharmaceutical. Briefly, fluorine-18 displays simple decay and emission properties with a high 97% positron abundance. Compared with the other conventional short-lived positron-emitting radionuclides carbon-11, nitrogen-13 and oxygen-15, fluorine-18 has a relatively low positron energy (maximum 635 keV) and the shortest positron linear range in tissue (2.3 mm), resulting in the highest resolution in PET imaging. Its half-life (109.8 min) is long enough to give access to relatively extended imaging protocols compared to what is possible with carbon-11, therefore facilitating kinetic studies and high-quality plasma metabolite analysis. Moreover, from a chemical point of view, fluorine-18 allows multi-step synthetic approaches that can be extended over hours. Finally, fluorine-18 can be reliably and routinely produced at the multi-Curie level, using the well-characterized (p, n) nuclear reaction on an oxygen-18-enriched water target on widely implemented biomedical cyclotrons of a relatively low-energy proton beam (e.g., 18 MeV).

To conclude, the use of a specific tracer, radiolabelled by fluorine-18, in PET imaging could lead to an increase of sensitivity of this technique, compared with [$^{18}$F]FDG, especially for the diagnosis of stage I (ocular) or II melanoma and the differential diagnosis with other tumours. Use of PET imaging is complementary to SPECT imaging and even in some contexts PET imaging, and more particularly fluorine-18 PET imaging, compared to SPECT allows better performances in terms of image quality or quantification of uptake namely for dosimetry.

SUMMARY

Thus, the object of the present invention is the targeting of melanoma lesions by the development of molecules which, administered to the body, will make it possible to vectorize a radioisotope. The present invention therefore concerns two fields of applications, namely imaging and radionuclide therapy, depending on the nature of the labelling.

Moreover the compounds in accordance with the present invention are of advantage both for their use in imaging, namely for the diagnosis of malignant melanoma, and in vectorized internal radionuclide therapy, targeting more particularly secondary lesions and primary ocular lesions. One of the major advantages of the compounds according to the present invention lies precisely in their mixed potentiality or bimodality property. In other words, according to the chemical variations under consideration, their respective behaviours in the body destine them more particularly for use in medical imaging, for use in radionuclide therapy or else, and these compounds may prove to be particularly attractive when they are able to be used both in medical imaging and in radionuclide therapy. Said molecules endowed with said bimodal potentiality are of particular interest.

To this end, the compounds of the present invention all comprise at least a fluorine atom so that they are more particularly dedicated to reach an application in PET imaging when said at least one fluorine atom is labelled into fluorine-18 but also comprise another radionuclide and/or halogen allowing them to reach another imaging potentiality of melanoma (for example SPECT) and/or a therapeutic property against melanoma.

Finally, some compounds corresponding to the general formula of the compounds in accordance with the present invention, when they are unlabelled, may also exhibit an intrinsic antitumour activity. Thus, in this specific case, one can say that the nonradioactive component defined above can play, in addition to its role of targeting the melanoma lesions and/or of promoting absorption of radioactivity, a role of cytotoxic agent per se. However, even if some compounds of the present invention may exhibit a chemotherapy potentiality, it is clearly the activity via labelling by a radioactive isotope which is targeted in the present invention.

DETAILED DESCRIPTION

Figure 1:
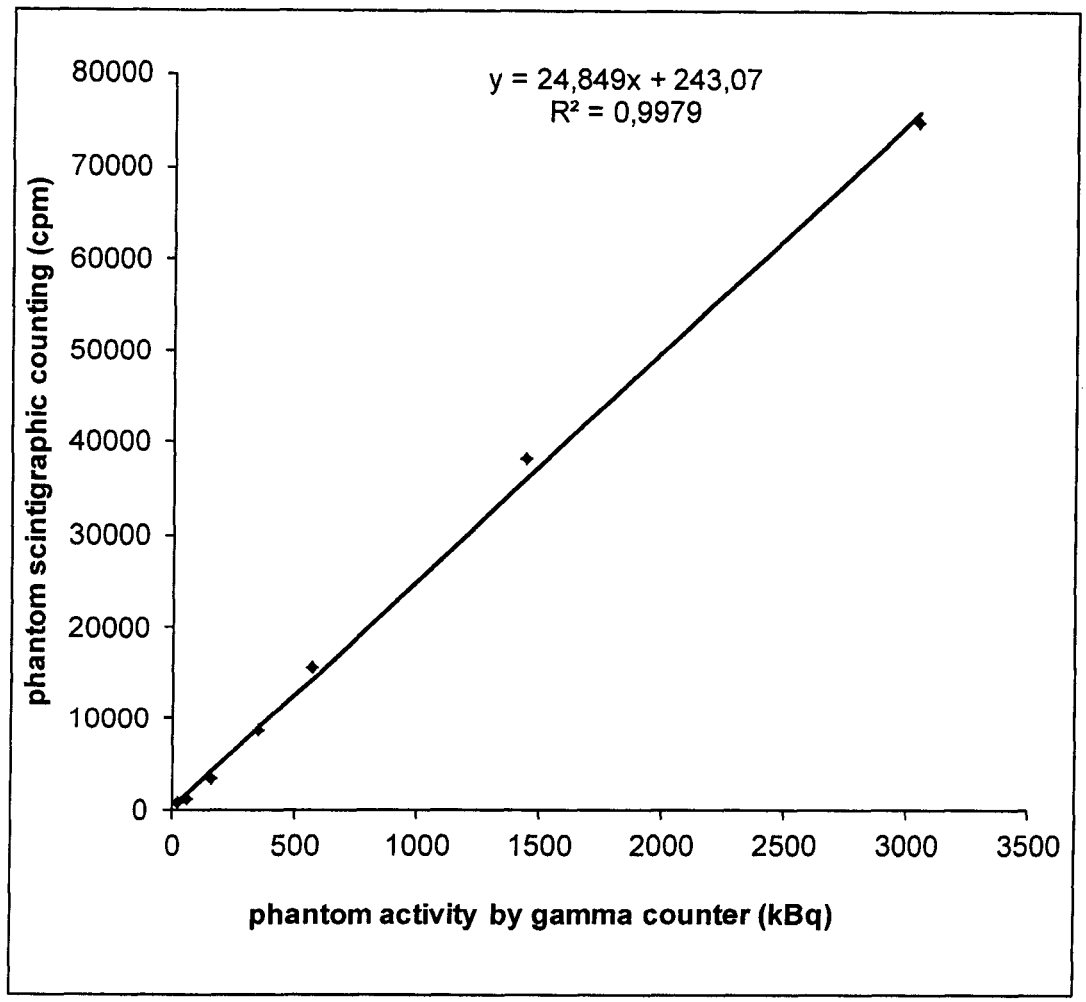
FIG. 1: Phantom activity measurements.

According to a first aspect, a subject-matter of the present invention relates to a compound of formula (I):

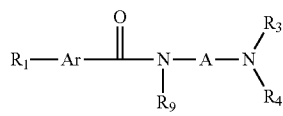

(I)

in which $R_1$ represents a hydrogen atom, an optionally labelled halogen, a radionuclide or a $Sn[(C_1-C_4)alkyl]_3$ group, Ar represents an aryl group or a heteroaryl group, it being possible for the said aryl or heteroaryl group to be mono or disubstituted by:

an optionally labelled halogen,
a hydroxy group,
a $(C_1-C_4)$alkyl group,
a $(C_1-C_8)$alkoxy group,
a —$NO_2$ group,
an oxo group,
a —$NR_5R_6$, —$N^+R_5R_6R_7X^-$, —$NHCO_2R_8$, —$NHCOR_8$, —$CONHR_8$, —$NHCONHR_8$, —$SR_8$, —$COR_8$, —$CO_2R_8$ or —$SO_2R_8$ group,
an aryl or an arylalkyl group, or
a $Sn[(C_1-C_4)alkyl]_3$ group, $R_5$, $R_6$ and $R_7$ independently represent a hydrogen atom, a $(C_1-C_4)$alkyl group, an aryl group or an arylalkyl group, $X^-$ represents a monovalent anion, for example a sulphate, a halide and more particularly an iodide or a triflate, $R_8$ represents a hydrogen atom, a $(C_1-C_8)$alkyl group, an aryl group or an arylalkyl group, $R_9$ represents a hydrogen atom, a $(C_1-C_4)$alkyl group or forms together with the group $R_1$—Ar a ring fused with the Ar group, forming the following bicyclic ring:

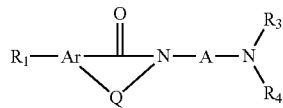

(Ia)

wherein Q is a $(CH_2)_p$ group or a —CO— group and p is an integer ranging from 1 to 3, the bond between $R_1$—Ar and Q being for example bound to Ar in ortho position from the bond between Ar and the remaining structure. The obtained structure corresponds for example to the following phthalimide formula (α):

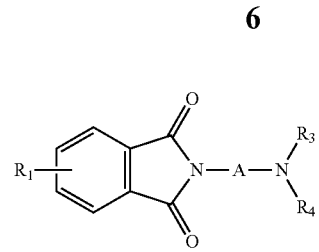

(α)

wherein $R_1$ is as defined above, and $R_3$, $R_4$ and A are as defined beneath, and which forms part of the present invention.

A represents a group of formula (β) or (δ):

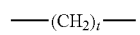

(β)

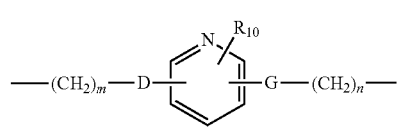

(δ)

wherein t is an integer ranging from 2 to 4, m and n are integers independently ranging from 0 to 4, D and G are independently selected from —$(CH_2)_x$—, —O—, —NH—, —S—, —$SO_2$—, —CONH—, —NHCO—, —$CO_2$— and —$NHCO_2$—, wherein x is a integer ranging from 0 to 4, $R_{10}$ represents a hydrogen atom, an optionally labelled halogen, a radionuclide, a —$NO_2$ group, a —$NR_5R_6$ group, a —$N^+R_5R_6R_7X^-$ group, wherein $R_5$, $R_6$, $R_7$ and $X^-$ are as defined above, $R_3$ and $R_4$ independently represent a hydrogen atom, a $(C_1-C_6)$alkyl group, a $(C_1-C_6)$alkenyl group or a group of formula (γ):

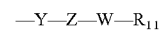

(γ)

wherein

Y, Z, W independently represent (i) a bond, (ii) a $(C_1-C_8)$alkylene group, a $(C_2-C_{10})$alkenylene group, a $(C_2-C_{10})$alkynylene group, or (iii) a group selected from —O—, —NH—, —S—, —$SO_2$—, —CO—, —$CO_2$—, —CONH—, —NHCO— and —$NHCO_2$—, with the proviso that at most one of Y, Z, W has the above definition (iii), $R_{11}$ represents an optionally labelled halogen, a radionuclide, an aryl or heteroaryl group optionally substituted by an optionally labelled halogen, a radionuclide, a —$NO_2$ group, a —$NR_5R_6$ group or a —$N^+R_5R_6R_7X^-$ group, wherein $R_5$, $R_6$, $R_7$ and $X^-$ are as defined above, or a —$OSO_2R_{12}$ group, wherein $R_{12}$ is a $(C_1-C_6)$alkyl group, a $(C_3-C_8)$cycloalkyl, an aryl group or a heteroaryl group, wherein said alkyl, cycloalkyl, aryl or heteroaryl groups are optionally substituted by 1 to 3 group(s) chosen among a halogen, a $(C_1-C_4)$alkyl group, a —$NO_2$ group, a —CN group or a —$NR_5R_6$ group, where $R_5$ and $R_6$ are as defined above, with the proviso that:
the compound of formula (I) comprises at least one optionally labelled fluorine atom or a precursor group thereof and in particular of a fluorine-18 atom, and
the $R_1$—Ar group comprises at least an optionally labelled halogen or a radionuclide other than an optionally labelled fluorine atom,
and their addition salts with pharmaceutically acceptable acids.

According to a particular embodiment, Ar is different from a phenyl group.

According to another particular embodiment, when Ar is a phenyl group, at least one of the $R_3$ and $R_4$ groups represents a group of formula (ε)

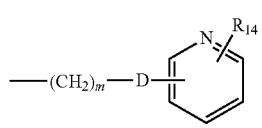

wherein:
m and D are as defined above, and
$R_{14}$ represents a hydrogen atom, an optionally labelled halogen, a radionuclide, a —$NO_2$ group, a —$NR_5R_6$ group or a —$N^+R_5R_6R_7X^-$ group, wherein $R_5$, $R_6$, $R_7$ and $X^-$ are as defined above.

According to another particular embodiment, the present invention is directed to a compound of formula (I) as defined above, inclusive of the two above-mentioned particular embodiments in connection to the Ar definition, except the above-mentioned proviso, now reading as follows:
with the proviso that:
the compound of formula (I) comprises at least one optionally labelled fluorine atom or a precursor group thereof and in particular a fluorine-18 atom, and
the $R_1$—Ar group comprises at least an optionally labelled halogen or a radionuclide other than said previous optionally labelled fluorine atom or said previous precursor group thereof.

In the framework of the present invention, a precursor group of an optionally labelled fluorine atom is in particular chosen, in aromatic series, among a —$NO_2$ group, a halogen with the exclusion of fluorine, a —$N^+R_5R_6R_7X^-$ group, wherein $R_5$, $R_6$, $R_7$, and $X^-$ are as defined above, and in aliphatic series among a halogen with the exclusion of fluorine, or a —$OSO_2R_{12}$ group, wherein $R_{12}$ is a $(C_1-C_6)$alkyl group, a $(C_3-C_8)$cycloalkyl, an aryl group or an heteroaryl group, wherein said alkyl, cycloalkyl, aryl or heteroaryl groups are optionally substituted by 1 to 3 group(s) chosen among a halogen, a $(C_1-C_4)$alkyl group, a —$NO_2$ group, a —CN group or a —$NR_5R_6$ group, where $R_5$ and $R_6$ are as defined above.

By "aromatic series" is meant the compounds wherein the precursor group is linked to an aryl or heteroaryl group and by "aliphatic series" is meant compounds wherein the precursor group is linked to alkyl, alkenyl, alkynyl, alkylene, alkenylene or alkynylene group.

In other words, a precursor group according to the invention is in particular chosen among a —$NO_2$ group, a halogen with the exclusion of fluorine, a —$N^+R_5R_6R_7X^-$ group, wherein $R_5$, $R_6$, $R_7$ and $X^-$ are as defined above, when said precursor group is linked to an aryl or heteroaryl group among a halogen with the exclusion of fluorine, or a —$OSO_2R_{12}$ group, wherein $R_{12}$ is a $(C_1-C_6)$alkyl group, a $(C_3-C_8)$cycloalkyl, an aryl group or an heteroraryl group, wherein said alkyl, cycloalkyl, aryl or heteroaryl groups are optionally substituted by 1 to 3 group(s) chosen among a halogen, a $(C_1-C_4)$alkyl group, a —$NO_2$ group, a —CN group or a —$NR_5R_6$ group, where $R_5$ and $R_6$ are as defined above when said precursor group is linked to alkyl, alkenyl, alkynyl, alkylene, alkenylene or alkynylene group.

Moreover formula (I) encompasses the radiotracers themselves, which are the agents for imaging and/or for targeted radionuclide therapy of melanoma which typically encompass only one radioisotope, but also the corresponding precursors, more particularly the compounds which are not yet labelled, i.e. their non-radiolabelled precursors.

According to one aspect, the present invention relates to a compound of formula (I), wherein the at least one optionally labelled fluorine atom or precursor group thereof is comprised in the $R_3$ or $R_4$ group.

According to another aspect, the present invention relates to a compound of formula (I), wherein the at least one optionally labelled fluorine atom or precursor group thereof is comprised in the $R_1$—Ar group.

According to another aspect, the present invention relates to a compound of formula (I), wherein the at least one optionally labelled fluorine atom or precursor group thereof is comprised in the (δ) group as defined above.

According to another aspect, the invention is directed to labelled compounds of formula (I), and in particular to compounds of formula (I) comprising a fluorine-18 atom and wherein the group $R_1$—Ar comprises at least a $Sn[(C_1-C_4)$alkyl$]_3$ group or a halogen other than a fluorine atom.

According to still another aspect, the invention is directed to compounds of formula (I) which simultaneously comprise two labelled atoms, i.e. a fluorine-18 atom and another labelled atom different from fluorine-18, for example a labelled iodine atom.

According to another aspect, a subject-matter of the invention is a product chosen from the compounds of formula (I), and in particular a labelled compound of formula (I) as defined above for the diagnosis and/or the treatment of melanoma.

When A represents formula (δ) and $R_{10}$ is different from a hydrogen atom, $R_{10}$ is preferentially linked to the 2, 4 or 6 positions of the pyridine ring.

In the context of the present invention, the term:
"halogen" is understood to mean chlorine, fluorine, bromine, iodine or astatine,
"arylalkyl" refers to an alkyl radical in which one of the hydrogen atoms bound to a carbon atom, typically a terminal or $sp^3$ carbon atom, is replaced with an aryl radical. Typically arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Arylalkyl groups comprise 6 to 20 carbon atoms. Typically, the alkyl moiety, including alkyl, alkenyl or alkynyl groups, of the arylalkyl group consists of 1 to 6 carbon atoms and the aryl moiety consists of 5 to 14 carbon atoms,
"$(C_1-C_4)$alkyl" as used herein refers to $C_1-C_4$ normal, secondary, or tertiary unsaturated hydrocarbon. Examples are, but are not limited to, methyl, ethyl, 1-propyl, 2-propyl, 1-butyl, 2-methyl-1-propyl (i-Bu), 2-butyl (s-Bu), 2-methyl-2-propyl (t-Bu). In a particular embodiment, the term also includes $(C_1-C_4)$haloalkyl group, which is a $(C_1-C_4)$alkyl group bearing at least one halogen,
"$(C_2-C_{10})$alkenyl", as used herein, is a $C_2-C_{10}$ normal or secondary hydrocarbon chain with at least one site of unsaturation, i.e. a carbon-carbon, $sp^2$ double bond. Example includes, but is not limited to ethenyl. The double bond may be in the cis or trans configuration, "alkynyl", as used herein, is a normal or secondary hydrocarbon chain with one site of unsaturation, i.e. a carbon-carbon, sp triple bond. Example includes, but is not limited to ethynyl, "$(C_1-C_8)$alkylene", as used herein, means a saturated divalent radical comprising 1 to 8 carbon atoms, including straight or branched chain moieties. Some examples of branched-chain alkylene moieties are ethylethylene, 2-methyltrimethylene, 2,2-dimethyltrimethylene etc, "$(C_2-C_{10})$alkenylene", as used herein, is a divalent radical comprising 2 to 10 carbon atoms and comprising at least one site of unsaturation, "$(C_2-C_{10})$alkynylene", as used herein, is a divalent radical comprising 2 to 10 carbon atoms and comprising at least one triple bond, "$(C_1-C_4)$alkoxy group", as used herein, is —$O(C_1-C_4)$ alkyl group wherein the $(C_1-C_4)$alkyl group is as defined above.

"aryl" refers to a mono or polycyclic aromatic hydrocarbon radical of 6-20 atoms derived by the removal of one hydrogen from a carbon atom of a parent aromatic ring system. Typical aryl groups include, but are not limited to 1 ring or 2 or 3 rings fused together. Said radical is typically derived from the rings selected from benzene, naphthalene, anthracene, and the like. "Aryl" preferably refers to radicals such as phenyl, naphthyl, anthryl or phenanthryl. According to a particular embodiment, the term "aryl" is directed to naphthyl, anthryl or phenanthryl.

"heteroaryl" denotes a 5 or 6-membered aromatic ring comprising 1 to 4 heteroatoms or a bi or tricyclic aromatic ring comprising from 1 to 4 heteroatoms. According to one embodiment, at least one of the rings is a 6 membered-ring, the other fused ring or rings are 5 or 6-membered rings, "heteroatom" is understood to mean nitrogen, oxygen or sulphur. Preferably "heteroatom" is nitrogen.

For example, a radical corresponding to a 5 or 6 aromatic membered ring containing 1 to 4 heteroatoms, in accordance with the present invention, can be: pyridyl, thiazolyl, furyl, thienyl, pyrrolyl, pyrazolyl, imidazolyl, pyranyl, isothiazolyl, isoxazolyl, pyrazinyl, pyridazinyl, pyrimidinyl, tetrazolyl, triazinyl, furazanyl or thiofuranyl.

For example, a radical corresponding to a bi or tricyclic aromatic ring containing 1 to 4 heteroatoms, in accordance with the present invention, can be: chromenyl, isochromenyl, benzofuryl, thianaphthalenyl, indolyl, indolenyl, quinolyl, isoquinolyl, benzimidazolyl, thianthrenyl, isobenzofuryl, xanthenyl, phenoxathinyl, indolizinyl, isoindolyl, indazolyl, purinyl, quinolizinyl, phthalazinyl, naphthyridinyl, quinoxalinyl, cinnolinyl, pteridinyl, carbazolyl, β-carbolinyl, phenanthridinyl, acridinyl, acridonyl, phenanthrolinyl, phenazinyl, phenothiazinyl, phenoxazinyl, benzotriazolyl, benzisoxazolyl, benzothienyl, benzothiazolyl, isatinoyl, quinazolinyl, benzothiophenyl, perimidinyl, benzisoquinolinyl, imidazotriazinyl, imidazopyridinyl.

Mention may be made, as example of bi or tricyclic aromatic radical in accordance with the present invention, of the radical having benzene as one of the rings, including indole, isoindole, quinoline, isoquinoline, quinoxaline, benzimidazole, indazole, phthalazine, quinazoline, cinnoline, naphthalene or benzothiophene for the bicycles and carbazole, phenanthridine, acridine, acridone, phenothiazine, phenoxazine, phenazine, phenanthroline, carboline, perimidine and benzisoquinoline for the tricycles.

Mention may be made, as example of bi or tricyclic aromatic radical in accordance with the invention, each of the rings of which, taken in isolation, is an aromatic radical comprising at least one heteroatom, of naphthyridine, quinolizine, purine, imidazopyridine, indolizine, pteridine, imidazotriazine or pyrazinopyridazine for the bicycles.

Preferentially, the heteroaryl group contains, at least, one nitrogen atom as heteroatom. According to a particular embodiment, the heteroaryl comprises only nitrogen atoms as heteroatom(s). Thus, conveniently, the heteroaryl group contains 1 to 4 nitrogen atoms, in particular 1 or 2 nitrogen atoms.

Preferentially, the heteroaryl group can be pyridyl, quinoxalinyl, quinolyl, isoquinolyl, imidazopyridyl, naphthyridinyl, acridinyl, acridonyl or phenazinyl.

In the context of the present invention, acridone is an acridine substituted by an oxo group on the 9 position.

In the framework of the present invention, the heteroaryl group can be partially hydrogenated. However, in the case of bi or tricyclic rings, each of the rings, separately considered, contains at least one double bond. In the present invention, the terms "aromatic ring", "aryl" and "heteroaryl" include all position isomers thereof.

Within the meaning of the present invention, the term "radionuclide" is understood to mean an isotope of natural or artificial origin which demonstrates radioactive properties. The radionuclide can be a radioisotope chosen from iodine-123, iodine-124, iodine-125, iodine-131, bromine-75, bromine-76, bromine-77, fluorine-18, astatine-210 or astatine-211.

According to a particular embodiment, $R_1$, $R_{10}$, $R_{11}$ and $R_{14}$ can independently, and preferably not simultaneously represent a radionuclide selected from iodine-123, iodine-124, iodine-125, iodine-131, astatine-211 and fluorine-18.

Moreover, the term "labelled" as used herein means "radiolabelled" and is more precisely directed to a compound comprising at least one radionuclide, i.e. a radioactive nuclide.

According to a specific embodiment, the compound of formula (I) comprises at least one iodine atom and more particularly said iodine atom being located on the $R_1$—Ar group.

According to a more particular embodiment, the present invention is directed to a compound of formula (I) wherein:
$R_1$ is an optionally labelled iodine atom, in particular iodine-123, iodine-124, iodine-125 or iodine-131,
A represents a (β) group,
$R_3$ represents a $(C_1-C_6)$alkyl group, and
$R_4$ represents a (γ) group, said group comprising a fluorine atom or a precursor thereof, the remaining groups being as defined above.

According to a particular embodiment of the present invention, when Ar comprises only one ring, the preferred compound of formula (I) exhibits the $R_1$ group in the ortho or para position with respect to the group:

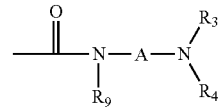

According to a particular embodiment, the compound of formula (I) exhibits a bi or tricyclic aromatic radical as defined above and the $R_1$ group is bonded to one of the rings and the group:

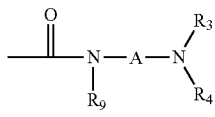

is bound to the other ring or to one of the other rings.

According to yet another particular embodiment of the present invention, preference is given to a compound of formula (I), characterized in that Ar is a bi or tricyclic heteroaryl group as defined above and in that $R_1$ is bound to the ring, taken in isolation, not comprising a heteroatom or comprising the least thereof and the group

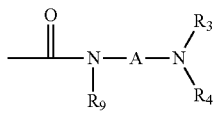

is bound to another ring comprising the greater number of heteroatom(s).

The following particular embodiments form part of the present invention, which may be considered independently or which may be combined together, their addition salts with pharmaceutically acceptable acids being encompassed:

The compound of formula (I), wherein Ar represents a group selected from naphthyl, anthryl, pyridyl, quinoxalinyl, quinolyl, isoquinolyl, imidazopyridyl, naphthyridinyl, acridinyl, acridonyl and phenazinyl, it being possible for said group to be monosubstituted by a methyl group, a methoxy group or an optionally labelled halogen, The compound of formula (I), wherein $R_9$ is a hydrogen atom, The compound of formula (I), wherein A is a (β) group wherein more particularly t is 2, The compound of formula (I), wherein $R_3$ and $R_4$ independently represent a hydrogen atom, a $(C_1$-$C_4)$alkyl group, a group —Y—Z—W—$R_{11}$ (γ), wherein Y, Z and W independently represent
  (i) a bond,
  (ii) a $(C_1$-$C_4)$alkylene group, a $(C_2$-$C_{10})$alkenylene group or a $(C_2$-$C_{10})$alkynylene group, or
  (iii) a group selected from —O—, —NH—, —CONH— and —NHCO— with the proviso that at most one of Y, Z, W has the above definition (iii), and $R_{11}$ represents
  An optionally labelled halogen, and more particularly an optionally labelled fluorine atom,
  A

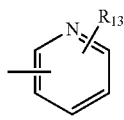

group, wherein $R_{13}$ represents a hydrogen atom, an optionally labelled halogen, a radionuclide, a —$NO_2$ group, a —$NR_5R_6$ group or a —$N^+R_5R_6R_7X^-$ group, wherein $R_5$, $R_6$, $R_7$ and $X^-$ are as defined above.

According to a particular embodiment, an additional subject-matter of the present invention is a compound of formula (Ib),

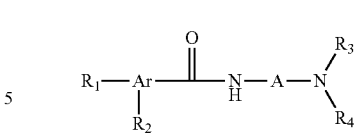

(Ib)

in which:

$R_1$ and A are as defined above,

Ar represents an aryl or a heteroaryl group, $R_2$ is chosen among an optionally labelled halogen, a radionuclide, a hydroxy group, a $(C_1$-$C_4)$alkyl group, a $(C_1$-$C_8)$alkoxy group, a —$NO_2$ group, an oxo group, a —$NR_5R_6$ group, a —$N^+R_5R_6R_7X^-$ group, wherein $X^-$ is as defined above, a —$NHCO_2R_8$ group, a —$NHCOR_8$ group, a —$CONHR_8$ group, a —$NHCONHR_8$ group, a —$SR_8$ group, a —$COR_8$ group, a —$CO_2R_8$ group, a —$SO_2R_8$ group, an aryl group or a $Sn[(C_1$-$C_4)alkyl]_3$ group, $R_5$, $R_6$ and $R_7$ independently represent a hydrogen atom, a $(C_1$-$C_4)$alkyl group, an aryl group or an arylalkyl group, and $R_8$ represents a hydrogen atom, a $(C_1$-$C_8)$alkyl group, an aryl group or an arylalkyl group, $R_3$ and $R_4$ independently represent a hydrogen atom, a $(C_1$-$C_6)$alkyl group, a $(C_1$-$C_6)$alkenyl group or a group of formula (ε) or (φ)

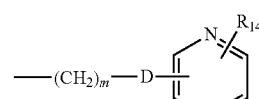

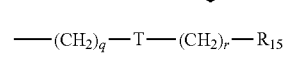

wherein:

m and D are as defined above, $R_{14}$ represents a hydrogen atom, an optionally labelled halogen, a radionuclide, a —$NO_2$ group, a —$NR_5R_6$ group or a —$N^+R_5R_6R_7X^-$ group, wherein $R_5$, $R_6$, $R_7$ and $X^-$ are as defined above, q and r are integers and independently ranging from 0 to 8, T represents a bond, a $(C_1$-$C_4)$alkylene group, a $(C_2$-$C_{10})$alkenylene group or a $(C_2$-$C_{10})$alkynylene group, and $R_{15}$ represents
  an optionally labelled halogen,
  a radionuclide,
  a —$OSO_2R_{12}$ group, wherein $R_{12}$ is as defined above, with the proviso that:

the compound of formula (Ib) comprises at least one optionally labelled fluorine atom or a precursor group thereof and in particular a fluorine-18 atom, and the $R_1$—Ar group comprises at least an optionally labelled halogen or a radionuclide other than an optionally labelled fluorine atom, and their addition salts with pharmaceutically acceptable acids.

According to a particular embodiment, Ar is different from a phenyl group.

According to another particular embodiment, when Ar is a phenyl group, at least one of the $R_3$ and $R_4$ groups represents a group of formula (ε)

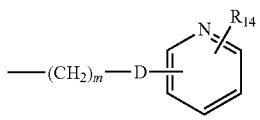

(ε)

wherein:
m and D are as defined above, and
$R_{14}$ represents a hydrogen atom, an optionally labelled halogen, a radionuclide, a —$NO_2$ group, a —$NR_5R_6$ group or a —$N^+R_5R_6R_7X^-$ group, wherein $R_5$, $R_6$, $R_7$ and $X^-$ are as defined above.

According to another particular embodiment, the present invention is directed to a compound of formula (Ib) as defined above, inclusive of the two above-mentioned particular embodiments in connection to the Ar definition, except the above-mentioned proviso, now reading as follows:

with the proviso that:
the compound of formula (Ib) comprises at least one optionally labelled fluorine atom or a precursor group thereof and in particular a fluorine-18 atom, and
the $R_1$—Ar group comprises at least an optionally labelled halogen or a radionuclide other than said previous optionally labelled fluorine atom or said previous precursor group thereof.

In the framework of the definition of formula (Ib), when A represents formula (δ) and $R_{10}$ is different from a hydrogen atom, $R_{10}$ is preferentially linked to the 2, 4 or 6 position of the pyridine ring. Moreover, when $R_3$ and/or $R_4$ represents formula (ε) and $R_{14}$ is different from a hydrogen atom, $R_{14}$ is preferentially linked to the 2, 4 or 6 position of the pyridine ring.

According to a particular embodiment, the present invention relates to a compound of formula (Ib), wherein the aryl or heteroaryl group is chosen from pyridyl, quinolyl, isoquinolyl, quinoxalinyl, acridinyl, acridonyl, phenazinyl, naphthyl, naphthyridinyl and imidazopyridyl.

The following particular embodiments form part of the present invention, which may be considered independently or which may be combined together, their addition salts with pharmaceutically acceptable acids encompassed:

The compound of formula (Ib), wherein Ar represents a group selected from naphthyl, anthryl, pyridyl, quinoxalinyl, quinolyl, imidazopyridyl, naphthyridinyl, acridinyl, acridonyl and phenazinyl, it being possible for said group to be monosubstituted by a methyl group, a methoxy group or an optionally labelled halogen, The compound of formula (Ib), wherein A is a (β) group wherein more particularly t is 2, The compound of formula (Ib), wherein $R_3$ and $R_4$ independently represent a hydrogen atom, a ($C_1$-$C_6$)alkyl group, a ($C_1$-$C_6$)alkenyl group or a group of formula (ε) or (φ)

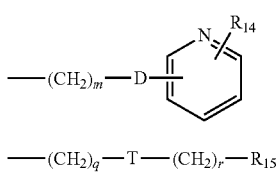

(ε)

(φ)

wherein:
m is as defined above,
D is —$(CH_2)_x$—, —O—, —NH—, —CONH— or —NHCO— x ranges from 0 to 2,
$R_{14}$ represents a hydrogen atom, an optionally labelled halogen, a radionuclide, a —$NO_2$ group, a —$NR_5R_6$ group or a —$N^+R_5R_6R_7X^-$ group, wherein $X^-$ is as defined above,
$R_5$, $R_6$ and $R_7$ are a hydrogen atom or a ($C_1$-$C_4$)alkyl group,
q and r are integers and independently ranging from 0 to 3,
T represents a bond, a ($C_1$-$C_4$)alkylene group, a ($C_2$-$C_{10}$) alkenylene group or a ($C_2$-$C_{10}$)alkynylene group, and
$R_{15}$ represents
an optionally labelled halogen,
a radionuclide,
a —$OSO_2R_{12}$ group, wherein $R_{12}$ is a trifluoromethyl group, a toluoyl group, a bromophenyl group, a nitrophenyl group or a methyl group.

According to a particular embodiment, the present invention is directed to a compound of formula (Ib) as defined above,
wherein Ar represents a group selected from naphthyl, anthryl, pyridyl, quinoxalinyl, quinolyl, imidazopyridyl, naphthyridinyl, acridinyl, acridonyl and phenazinyl, it being possible for said group to be monosubstituted by a methyl group, a methoxy group or an optionally labelled halogen, and
wherein:
when A represents a group of formula (β) as defined above,
either at least one of the $R_3$ and $R_4$ groups represents a group of formula (ε) or (φ)

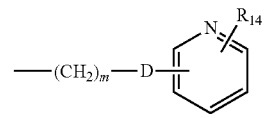

(ε)

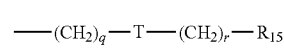

(φ)

wherein
m, D, q, T, and r are as defined above, and
$R_{14}$ and $R_{15}$ represent an optionally labelled fluorine atom or a precursor group thereof and in particular a fluorine-18 atom;
or $R_3$ and $R_4$ represent a ($C_1$-$C_6$)alkyl group or a ($C_1$-$C_8$) alkenyl group, and the optionally labelled fluorine atom or a precursor group thereof and in particular a fluorine-18 atom is located in the $R_2$ group;
when A represents a group of formula (δ) as defined above,
$R_{10}$ represents an optionally labelled fluorine atom or a precursor group thereof and in particular a fluorine-18 atom.

An additional subject matter of the present invention is a compound of formula (Ic)

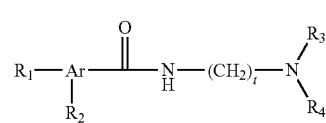

(Ic)

in which:
Ar is chosen from pyridyl, quinolyl, isoquinolyl, quinoxalinyl, acridinyl, acridonyl, phenazinyl, naphthyl, naphthyridinyl and imidazopyridyl, $R_1$ is an optionally labelled iodine atom, $R_2$ represents a hydrogen atom, a $(C_1-C_4)$alkyl group, a $(C_1-C_4)$alkoxy group, an optionally labelled halogen, a —SH group, a —OH group, a —$NR_5R_6$ group or a —$N^+R_5R_6R_7X^-$ group, wherein $X^-$ is as defined above and wherein $R_5$, $R_6$ and $R_7$ can independently represent a hydrogen atom or a $(C_1-C_4)$ alkyl group, t is as defined above, $R_3$ and $R_4$ represent the formula (φ)

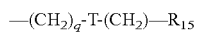  (φ)

wherein:

q and r are integers and independently ranging from 0 to 4,

T represents a bond, a $(C_1-C_4)$alkylene group, a $(C_2-C_{10})$alkenylene group or a $(C_2-C_{10})$alkynylene group or a group selected from —O—, —NH—, —CONH— and —NHCO—, and $R_{15}$ represents a hydrogen atom, an optionally labelled halogen (preferably a fluorine atom), a radionuclide, a —$OSO_2R_{12}$ group, wherein $R_{12}$ is as defined above, or a

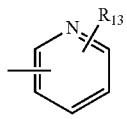

group, wherein $R_{13}$ represents a hydrogen atom, an optionally labelled halogen, a radionuclide, a —$NO_2$ group, a —$NR_5R_6$ group or a —$N^+R_5R_6R_7X^-$ group, wherein $X^-$ is as defined above and wherein $R_5$, $R_6$ and $R_7$ are as defined above and in particular independently represent a hydrogen atom or a $(C_1-C_4)$alkyl group, with the proviso that the compound of formula (Ic) comprises at least one optionally labelled fluorine atom or precursor group thereof and in particular a fluorine-18 atom, said fluorine atom being preferably located in the $R_2$, $R_3$ or $R_4$ group, and that the $R_1$—Ar group comprises at least an optionally labelled halogen or a radionuclide other than an optionally labelled fluorine atom, and their addition salts with pharmaceutically acceptable acids.

According to a particular embodiment, the above-mentioned proviso reads as follows:

with the proviso that:

the compound of formula (Ic) comprises at least one optionally labelled fluorine atom or a precursor group thereof and in particular of a fluorine-18 atom, said fluorine atom being preferably located in the $R_2$, $R_3$ or $R_4$ group, and the $R_1$—Ar group comprises at least an optionally labelled halogen or a radionuclide other than said previous optionally labelled fluorine atom or said previous precursor group thereof.

For compounds of formula (Ic), t is in particular equal to 2, 3 or 4, and more particularly equal to 2.

According to another particular embodiment, the present invention is directed to a compound of formula (Ic) wherein:

Ar, $R_1$, $R_2$ and t are as defined above, $R_3$ and $R_4$ independently represent a $(C_1-C_6)$alkyl group or a $(C_1-C_6)$alkenyl group or a group of formula (ε)

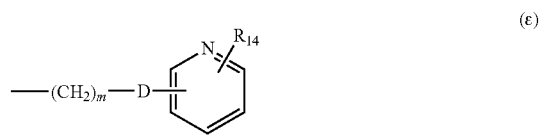  (ε)

wherein:

m and D are as defined above, and $R_{14}$ represents an optionally labelled halogen, a radionuclide, a —$NO_2$ group, a —$NR_5R_6$ group or a —$N^+R_5R_6R_7X^-$ group, wherein $R_5$, $R_6$, $R_7$ and $X^-$ are as defined above.

An additional subject matter of the present invention is a compound of formula (Id)

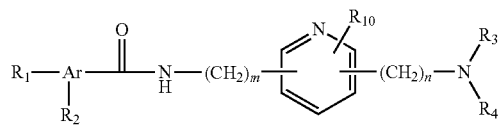  (Id)

in which:

Ar is chosen from pyridyl, quinolyl, isoquinolyl, quinoxalinyl, acridinyl, acridonyl, phenazinyl, naphthyl, naphthyridinyl and imidazopyridyl, $R_1$ is an optionally labelled iodine atom, $R_2$ represents a hydrogen atom, a $(C_1-C_4)$alkyl group, a $(C_1-C_4)$alkoxy group, an optionally labelled halogen, an —SH group, an —OH group, an —$NR_5R_6$ group or a —$N^+R_5R_6R_7X^-$ group, wherein $X^-$ is as defined above and wherein $R_5$, $R_6$ and $R_7$ can independently represent a hydrogen atom or a $(C_1-C_4)$alkyl group, $R_3$ and $R_4$ independently represent a $(C_1-C_6)$alkyl group or a $(C_1-C_6)$alkenyl group, m and n are integers independently ranging from 0 to 4, $R_{10}$ represents a hydrogen atom, an optionally labelled halogen, a radionuclide, a —$NO_2$ group, a —$NR_5R_6$ group, a —$N^+R_5R_6R_7X^-$ group, wherein $R_5$, $R_6$, $R_7$ and $X^-$ are as defined above, with the proviso that the compound of formula (Id) comprises at least one optionally labelled fluorine atom or precursor group thereof and in particular a fluorine-18 atom, said fluorine atom being preferably located in the $R_{10}$ group, and that the $R_1$—Ar group comprises at least an optionally labelled halogen or a radionuclide other than said previous optionally labelled fluorine atom or said previous precursor group thereof.

and their addition salts with pharmaceutically acceptable acids.

According to a particular embodiment, the present invention is directed to a compound of formula (Id) wherein:

Ar, $R_1$, $R_2$, m and n are as defined above;

$R_3$ and $R_4$ independently represent a $(C_1-C_6)$alkyl group or a $(C_1-C_6)$alkenyl group;

$R_{10}$ represents an optionally labelled halogen, in particular a fluorine atom and more particularly a fluorine-18 atom.

According to another aspect, a subject-matter of the invention is a product chosen from the compounds of formula (Ia), (Ib), (Ic) or (Id) and in particular a labelled compound of formula (Ia), (Ib), (Ic) or (Id) as defined above for the diagnosis and/or the treatment of melanoma.

In the framework of the invention, the groups of variable definition, in particular the $R_1$ and $R_2$ radicals, can take any position on the Ar group, and in particular on the heteroaryl. According to a specific embodiment, the $R_1$ group is bound to one of the rings and the group

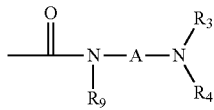

is bound to the other ring or to one of the other rings.

According to yet another embodiment, the $R_2$ radical is located, when this is possible, on a ring other than that carrying the $R_1$ group.

According to a preferred embodiment of the present invention, the compound is chosen from:

N-[2-[N-ethyl-N-[2-(2-fluoropyridin-3-yloxy)ethyl]amino]ethyl]-6-iodoquinoxaline-2-carboxamide (10), N-[2-[N-ethyl-N-[2-[(6-fluoropyridin-2-yl)amino]ethyl]amino]ethyl]-6-iodoquinoxaline-2-carboxamide (16), N-[2-[[N-ethyl-N-(6-fluoropyridin-2-yl)]amino]ethyl]-6-iodoquinoxaline-2-carboxamide (20), N-[2-[[N-ethyl-N-(2-fluoroethyl)]amino]ethyl]-6-iodoquinoxaline-2-carboxamide (25), N-[2-[[N-ethyl-N-(2-fluoropyridin-4-yl)methyl]amino]ethyl]-6-iodoquinoxaline-2-carboxamide (33), N-[2-[N-ethyl-N-[2-[[(2-fluoropyridin-4-yl)carbonyl]amino]ethyl]amino]ethyl]-6-iodoquinoxaline-2-carboxamide (39), N-[2-[[N-ethyl-N-2-(2-fluoropyridin-4-yl)ethyl]amino]ethyl]-6-iodoquinoxaline-2-carboxamide (46), N-[2-[[N-ethyl-N-3-(2-fluoropyridin-4-yl)propyl]amino]ethyl]-6-iodoquinoxaline-2-carboxamide (52), N-[2-[N-ethyl-N-((E)-4-fluorobut-2-enyl)]amino]ethyl]-6-iodoquinoxaline-2-carboxamide (56)

N-[2-[N-ethyl-N-[2-(2-nitropyridin-3-yloxy)ethyl]amino]ethyl]-6-iodoquinoxaline-2-carboxamide (60)

N-[2-[N-2-[(6-bromopyridin-2-yl)amino]ethyl]-N-(ethyl)amino]ethyl]-6-iodoquinoxaline-2-carboxamide (63)

N-[2-[N-ethyl-N-[2-(2-fluoropyridin-3-yloxy)ethyl]amino]ethyl]-6-iodoquinoline-2-carboxamide (67)

N-[2-[N-ethyl-N-[2-(2-fluoropyridin-3-yloxy)ethyl]amino]ethyl]-6-iodonaphthalene-2-carboxamide (70)

N-[2-[N-ethyl-N-[2-(2-fluoropyridin-3-yloxy)ethyl]amino]ethyl]-8-iodo-[1,6]naphthyridine-2-carboxamide (73)

N-[2-[N-ethyl-N-[2-(2-fluoropyridin-3-yloxy)ethyl]amino]ethyl]-6-iodoimidazo[1,2-α]pyridine-2-carboxamide (76)

N-[2-[N-ethyl-N-[2-(2-fluoropyridin-3-yloxy)ethyl]amino]ethyl]-7-iodoacridone-4-carboxamide (79)

N-[2-[N-ethyl-N-[2-(2-fluoropyridin-3-yloxy)ethyl]amino]ethyl]-7-iodophenazine-1-carboxamide (84)

N-[[4-(N N-diethylaminomethyl)-2-fluoropyridin-3-yl]methyl]-6-iodoquinoxaline-2-carboxamide (91)

N-[2-(diethylamino)ethyl]-4-fluoro-6-iodoquinoline-3-carboxamide (96) N-[2-(diethylamino)ethyl]-4-fluoro-6-iodoquinoline-8-carboxamide (102)

N-[2-(diethylamino)ethyl]-4-fluoro-6-iodoquinoline-2-carboxamide (106)

N-[2-(diethylamino)ethyl]-2-fluoro-6-iodoquinoline-4-carboxamide (110)

and their pharmaceutically acceptable salts, more particularly their chlorhydrates, or bases.

The compounds of formulae (I), (Ia), (Ib), (Ic) and (Id) can comprise one or more asymmetric carbon atoms. They can thus exist in the form of enantiomers or of diastereoisomers. These enantiomers, diastereoisomers and their mixtures, including the racemic mixtures, form part of the invention.

The pharmaceutically acceptable salts of the compounds of formulae (I), (Ia), (Ib), (Ic) and (Id) include the addition salts with pharmaceutically acceptable acids, such as inorganic acids, for example hydrochloric, hydrobromic, phosphoric or sulphuric acid and organic acids, such as acetic, trifluoroacetic, propionic, oxalic, succinic, fumaric, malic, tartaric, citric, ascorbic, maleic, glutamic, benzoic, toluenesulphonic, methanesulphonic, stearic and lactic acid.

The compounds of formulae (I), (Ia), (Ib), (Ic) and (Id) or their salts can form solvates (namely hydrates); the invention includes such solvates.

A further aspect of the invention pertains to a radiolabelled compound of formula (Ib), (Ic) or (Id) as described above, wherein said radiolabelling occurs by means of a radionuclide which can be a radioisotope chosen among iodine-123, iodine-124, iodine-125, iodine-131, bromine-75, bromine-76, bromine-77, fluorine-18, astatine-210 or astatine-211, and particularly is chosen among fluorine-18, iodine-123, iodine-124, iodine-125 et iodine-131.

When the compounds in accordance with the present invention of formulae (I), (Ia), (Ib), (Ic) and (Id), are used for medical imaging purposes, $R_1$ or the radionuclide located on the $R_1$—Ar group is preferably a radionuclide possessing γ or $β^+$ emission which can be detected according to conventional radioimaging techniques, for example scintigraphic imaging by single photon emission computed tomography (SPECT) and by positron emission tomography (PET).

Such a radionuclide possessing γ or $β^+$ emission advantageously exhibits an optimum energy for the measurement by means of a γ camera or PET camera. Mention may in particular be made, as radionuclides acceptable for medical imaging, of iodine-123, iodine-124, iodine-125, iodine-131, bromine-75, bromine-76, bromine-77 and fluorine-18.

Iodine-123 is particularly suitable for SPECT scintigraphic diagnosis and fluorine-18 or iodine-124 for a PET scintigraphic diagnosis.

When the compounds of the invention of formulae (I), (Ia), (Ib), (Ic) and (Id) are used for therapeutic purposes, $R_1$ or the radionuclide located on the $R_1$—Ar group is preferably a radionuclide possessing α, $β^-$ or Auger electron emission. The radionuclides suitable in this context, capable of providing a cytotoxic effect, can be chosen from iodine-131, iodine-125, astatine-210 and astatine-211.

Iodine-131 is particularly suitable for an application in the treatment of melanoma in internal radionuclide therapy. Furthermore, iodine-125, due to its Auger electron emission, can be used in internal radiotherapy provided that it is internalized in the cell.

Compounds according to the general formulae (I), (Ia), (Ib), (Ic) and (Id) can be prepared by condensation of a compound according to the general formula (IIa) or (IIb)

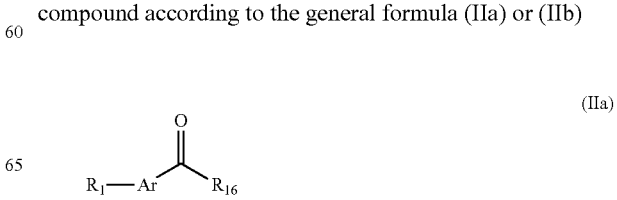

-continued

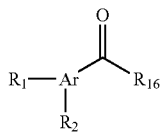
(IIb)

wherein:
R$_1$, R$_2$ and Ar are as defined above,
R$_{16}$ is a —OH group, a halogen, a —OR$_{17}$ group or a —OCOR$_{18}$ group,
wherein
R$_{11}$ is a (C$_1$-C$_6$)alkyl, an aryl or heteroaryl group, for example chosen from benzene, pentafluorobenzene, p-nitrobenzene, triazole, benzotriazole, 7-azabenzotriazole and succinimide and more particularly is a (C$_1$-C$_4$)alkyl or a p-nitrophenyl group,
R$_{18}$ is a (C$_1$-C$_6$)alkyl, an aryl or a (C$_1$-C$_4$)alkoxy group as ethoxy for example.
with a diamine, according to the general formula (III)

H$_2$N-A-NR$_3$R$_4$ (III)

wherein:
A, R$_3$ and R$_4$ are as defined above.

Condensation of compound (II) with diamine (III) can be performed according to general methods described by Montalbetti, C. A. G. N.; Falque, V. Amide bond formation and peptide coupling. *Tetrahedron* 2005, 61, 10827-10852.

Preferentially, the amide bond formation between an ester (II) and diamine (III) can be achieved in the presence or not of trimethylaluminium under reflux of anhydrous solvents such as dichloromethane, toluene or every other appropriate solvent. This condensation can also be achieved at room temperature in tetrahydrofuran, in the case of activated p-nitrophenyl ester.

Preferentially, the amide bond formation between an acyl halide (II), particularly an acyl chloride (II), and diamine (III) can be achieved in any inert dry solvents, in presence or not of a non-nucleophilic tertiary amine as base to trap the formed HCl. These reactions can also be accelerated in presence of pyridine, N,N-dimethylaminopyridine or metallic zinc used as catalyst.

These syntheses processes form part of the present invention.

Diamines, according to the general formula (III) as defined above can be prepared preferentially via intermediates containing a protective group on the primary amine.

The term "protective group" for the functional amino group discussed above are described in Greene and Wuts, "Protective groups in Organic Synthesis", John Wiley & Sons (1991), the entire teachings of which are incorporated into this application by reference. The person skilled in the art can select, using no more than routine experimentation, suitable protecting groups for use in the disclosed synthesis, including protecting groups other than those described below, as well as conditions for applying and removing the protecting groups.

According to a particular embodiment, the protective group can be a phthalimide group or a tert-butoxycarbonyl (Boc) group. In this case, diamines, according to the general formula (III), can be obtained after removing of the protective group and liberation of the primary amine, at room temperature or under reflux, by acidic hydrolysis of corresponding intermediates, containing a phthalimide or a Boc group or for phthalimide derivatives by reaction of those compounds with aqueous or ethanolic hydrazine solution.

The compounds of formula (III) including the compounds of formula (III) containing a protective group on the primary amine such as a phthalimide group or a tert-butoxycarbonyl (Boc) group, wherein A, R$_3$ and R$_4$ are as defined above, and wherein
A is a group (δ) as defined above and at least one optionally labelled fluorine atom or a precursor group thereof is located on said group, or
at least one of the R$_3$ and R$_4$ groups represents a group of formula (ε) as defined above and at least one optionally labelled fluorine atom or a precursor group thereof is located on said group,
form part of the present invention.

Compounds 5, 15, 19, 32, 38, 45, 51, 59, 62, 64 and 65 are compounds of formula (III) which are novel.

The synthesis routes of said compounds are more particularly illustrated in examples 1, 2, 3, 5, 6, 7, 8, 10, 11, 12 and 13.

The compounds of formulae (I), (Ia), (Ib), (Ic) and (Id) in which R$_3$ or R$_4$ is a hydrogen can preferably be prepared by condensation of the amine (III) with an ester (II) in which R$_{17}$ is a p-nitrophenyl group. This reaction can preferably be carried out in tetrahydrofuran at ambient temperature.

The compounds of formula (IIa) or (IIb), wherein R$_{16}$ is a —OH group or a —OR$_{17}$ group, can be synthesized from the compounds (IVa) or (IVb) according to various methodologies:

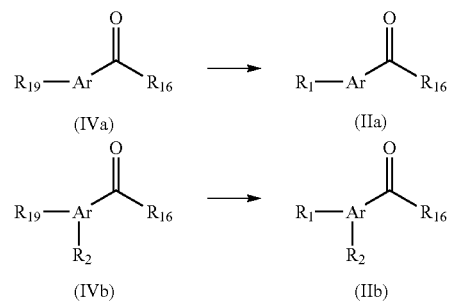

When R$_{19}$ is a hydrogen atom: by direct iodination of the aromatic or heteroaromatic part preferably using N-iodosuccinimide at reflux of the acetonitrile or of any other appropriate solvent. This iodination can also be carried out in the presence of diiodine, sodium periodate and sulphuric acid. The iodination can also be obtained after formation of an organolithium compound at low temperature, followed by treatment with diiodine.

When R$_{19}$ is a halogen: by direct exchange in the presence of alkali metal iodide, in an acidic medium, and in the presence or absence of a catalyst, such as copper sulphate. The halogen/iodine exchange can also be obtained after passing through an organometallic compound (organolithium compound, organomagnesium compound, organostannane compound, and the like) at low temperature, followed by treating the latter with diiodine.

When R$_{19}$ is a —NH$_2$ group: by a diazotization reaction, the amine being treated at 0° C. with sodium nitrite in an acidic medium, and then, after formation of the diazonium salt, by addition of alkali metal iodide and heating. This diazotization can also be carried out in an organic medium, the amino derivative being treated with tert-butyl nitrite in the presence of diiodomethane or of diiodine.

When R$_{19}$ is a —NO$_2$ or —NO group: by reduction, either by catalytic hydrogenation or by using a metal (Fe, Sn, and the like) in the presence of an acid (HCl, HBr, acetic acid, and the like). The amine thus obtained is treated according to the protocol described above.

The starting compounds of formulae (IVa), (IVb) and some compounds of formula (III), except the new ones as defined above are commercially available or are described in the literature, or can be synthetized in accordance with methods which are described therein or which are known to the man skilled in the art.

Radioiodination of compounds, according to the general formula (I), (Ia), (Ib), (Ic) or (Id), by iodine-123, iodine-124, iodine-125 or iodine-131, can be performed using several differents methods (Dewandjee, M. K. Radioiodination: theory, practice, and biomedical application. Kluwer academic publishers, Norwell, USA, 1992). For example, it can be achieved by an exchange, in acidic conditions, between the non radioactive iodinated molecule and an alkaline radioactive halide. The exchange can be carried out, for example under a temperature in a range of 100 to 200° C., using an aqueous solution of compounds, according to the general formula (I), (Ia), (Ib), (Ic) or (Id), and radioactive halide as [$^{125}$I]NaI in buffered medium or in acetic acid, in the presence or not of catalysts such as, for example, copper(II) sulfate. Radiolabelling can also be performed between a trialkylstannane precursor of compounds, according to the general formula (I), (Ia), (Ib), (Ic) or (Id), and an alkaline halide as [$^{125}$I]NaI or [$^{131}$I]NaI in the presence of an oxidative agent as chloramine-T, peracetic acid, hydrogen peroxide or in the presence or not of an acid as hydrochloric acid, acetic acid or an acid buffer solution, preferentially at room temperature and in an appropriate solvent.

Radiofluorination strategies and nature of the source of fluorine-18 for nucleophilic [$^{18}$F]fluorination.

Fluorine-18-labelling of compound according to the general formula (I), (Ia), (Ib), (Ic) or (Id), can be performed by nucleophilic substitutions with [$^{18}$F]fluoride, in order to maximize the specific radioactivities. Electrophilic substitutions can however also be used. Nucleophilic substitutions (aliphatic and aromatic) with [$^{18}$F]fluoride will usually be performed either on an immediate precursor of the target molecule (direct labelling using a one-step process) or on an indirect precursor followed by one or more chemical steps leading to the target radiotracer.

There is no particular restriction on the nature of the sources of [$^{18}$F]fluorides to be used in this reaction, and any sources of [$^{18}$F]fluorides conventionally used in reactions of this type may equally be used here, provided that it has no adverse effect on other parts of the molecule. Examples of suitable sources of [$^{18}$F]fluorides include: alkali metal [$^{18}$F]fluorides, such as sodium [$^{18}$F]fluoride, potassium [$^{18}$F]fluoride, cesium [$^{18}$F]fluoride; ammonium [$^{18}$F]fluoride, tetraalkylammonium [$^{18}$F]fluorides, such as tetrabutylammonium [$^{18}$F]fluoride. Of these, the alkali metal [$^{18}$F]fluorides, and notably a potassium [$^{18}$F]fluoride, are preferred. The source of [$^{18}$F]fluorides may be activated by the presence of a ligand able to complex the counter cationic species of the source of [$^{18}$F]fluorides. The ligand may be notably a cyclic or polycyclic multidentate ligand. Examples of suitable ligands include notably crown ethers such as 1,4,7,10,13-pentaoxacyclooctadecane (18C6) or cryptands such as 4,7,13,16,21,24-hexaoxa-1,10-diazabicyclo-[8,8,8]hexacosane sold under the name K222®. Preferably, the source of [$^{18}$F]fluoride is an alkaline metal [$^{18}$F]fluoride-cryptate complex, notably a potassium [$^{18}$F]fluoride-cryptate complex, preferably the potassium [$^{18}$F]fluoride-4,7,13,16,21,24-hexaoxa-1,10-diazabicyclo-[8,8,8]hexacosane ([$^{18}$F]KF/K222®). The complex [$^{18}$F]KF/K222® may be prepared by any conventional methods, for example as disclosed in Dollé, F.; Dolci, L.; Valette, H.; Hinnen, F.; Vaufrey, F.; Guenther, I.; Fuseau, C.; Coulon, C.; Bottlaender, M.; Crouzel, C. Synthesis and Nicotinic Acetylcholine Receptor in vivo Binding Properties of 2-Fluoro-3-[2(S)-2-azetidinylmethoxy]pyridine: A New Positron Emission Tomography Ligand for Nicotinic Receptors. *J. Med. Chem.* 1999, 42, 2251-2259; in Dollé, F.; Valette, H.; Vaufrey, F.; Fuseau, C.; Bottlaender, M.; Crouzel, C. Synthesis of a fluorine-18 labelled derivative of epibatidine for in vivo nicotinic acetylcholine receptor PET imaging. *Bioorg. Med. Chem.* 1999, 7, 467-479 and in Dollé, F.; Emond, P.; Mavel, S.; Demphel, S.; Hinnen, F.; Mincheva, Z.; Saba, W.; Valette, H.; Chalon, S.; Halldin, C.; Helfenbein, J.; Legaillard, J.; Madelmont, J. C.; Deloye, J. B.; Bottlaender, M.; Guilloteau, D. Synthesis, radiosynthesis and in vivo preliminary evaluation of [$^{11}$C]LBT-999, a selective radioligand for the visualisation of the dopamine transporter with PET. *Bioorg. Med. Chem.* 2006, 14, 1115-1125.

Typical example 1: One-step nucleophilic [$^{18}$F]fluorination in the aliphatic series.

The simplest pathway proposed for the labelling with fluorine-18 of [$^{18}$F]fluoroalkyl derivatives (compounds of formula (I), (Ia), (Ib), (Ic) or (Id)) is a one-step radiochemical process, involving a direct substitution of an appropriated atom or group (a leaving part) by [$^{18}$F]fluorine.

The best leaving-groups are the weakest bases, which is consistent with the principle that stable species make better leaving-groups. Iodide is usually the best leaving-group of the halides and fluoride the poorest. The sulphonic ester groups, such as the triflate ($CF_3SO_3$—), tosylate (p-Me$C_6H_4SO_3$—), mesylate ($CH_3SO_3$—), brosylate (p-Br$C_6H_4SO_3$—) and nosylate (m-$NO_2C_6H_4SO_3$—), are better leaving-groups than halides, leading to the following ranking order: $RSO_3$>I>Br>Cl>F. Of course, fluorine, in spite of its excellent leaving-group ability, is seldom used in fluorine-18 chemistry because of obvious isotopic dilution, leading to low specific radioactivity.

Aliphatic nucleophilic substitutions are usually performed under basic or neutral conditions, with a large assortment of solvents possible. Indeed, the effects of the solvent on $SN_2$-type reactions depend on the charge dispersal in the transition state compared to the one in the reactants. However, in radiofluorinations with [$^{18}$F]fluoride the solubility of the reactants appears to play a larger role in solvent choice than the solvent effects on reaction rates. The most common solvents are the polar aprotic ones, such as acetonitrile, in which the [$^{18}$F]fluoride salt ([$^{18}$F]KF, [$^{18}$F]CsF, [$^{18}$F]Bu$_4$NF or [$^{18}$F]KF/K222® complex for example) and the organic precursors for labelling show good solubility. The reaction is often performed at reflux temperature of the solvent for a few minutes.

Typical example 2: Two-step process involving a nucleophilic [$^{18}$F]fluorination in the aliphatic series followed by a (multi)deprotection step.

A typical pathway also often proposed for the labelling with fluorine-18 of [$^{18}$F]fluoroalkyl derivatives (compounds of formula (I), (Ia), (Ib), (Ic) or (Id)) is a two-step radiochemical process, involving first a direct substitution of an appropriated atom or group (a leaving part) by [$^{18}$F]fluoride (as described above) followed by a (multi)deprotection step. (Multi)Deprotection step is usually performed under basic or acidic conditions and depends on the chemical nature of the protective groups. Heating the reaction mixture for a few minutes may be required.

Typical example 3: Two-step process involving a nucleophilic [$^{18}$F]fluorination in the aliphatic series followed by a coupling step.

One robust and reliable pathway frequently proposed for the labelling with fluorine-18 of [$^{18}$F]fluoroalkyl derivatives (compounds of formula (I), (Ia), (Ib), (Ic) or (Id)) is a two-step radiochemical process, involving first the preparation of an appropriate halogeno or better sulphonyloxy [$^{18}$F]reagent. The radiosynthesis of n-bromo-, n-tosyloxy- and n-mesyloxy-1-[$^{18}$F]fluoroalkanes (n=1-3) from the corresponding bifunctional alkanes by nucleophilic aliphatic substitution with no-carrier-added [$^{18}$F]fluoride as for example its activated [$^{18}$F]KF/K222® complex ((a) Coenen, H. H.; Klatte, B.; Knoechel, A.; Schueller, M.; Stocklin, G. Preparation of n.c.a. [17-18F]-fluoroheptadecanoic acid in high yields via aminopolyether-supported, nucleophilic fluorination. *J. Label. Compds Radiopharm.* 1986, 23, 455-467. (b) Hamacher, K.; Coenen, H. H.; Stöcklin, G. Efficient stereospecific synthesis of no-carrier-added 2-[$^{18}$F]-fluoro-2-deoxy-D-glucose using aminopolyether supported nucleophilic substitution. *J. Nucl. Med.* 1986, 27, 235-238) has been extensively studied (Block, D.; Coenen, H. H.; Stocklin, G. The N.C.A. nucleophilic $^{18}$F-fluorination of 1,N-disubstituted alkanes as fluoroalkylation agents. *J. Label. Compds Radiopharm.* 1987, 24, 1029-1042) and uses methodologies described in the section above.

Typical example 4: One-step nucleophilic [$^{18}$F]fluorination in the aromatic series.

The simplest pathway proposed for the labelling with fluorine-18 of [$^{18}$F]fluoroaryl derivatives (compounds of formula (I), (Ia), (Ib), (Ic) or (Id)) is a one-step radiochemical process, involving a direct substitution of an appropriated atom or group (a leaving part) by [$^{18}$F]fluoride.

Leaving-groups include the halogens and particularly the nitro group (with the following accepted order of decreasing leaving-group ability: F>NO$_2$>Cl>Br and I). However, this depends greatly on the nature of the nucleophile and with [$^{18}$F]fluoride, the trimethylammonium group is often a better alternative, when available. Indeed, aryltrimethylammonium salts, which are relatively stable and easy to handle, tend to be more reactive than compounds with a neutral leaving-group and usually require milder conditions and give higher radiochemical yields in [$^{18}$F]fluoride substitution. They are also particularly convenient because of their superior separation from the reaction product, the neutral aryl [$^{18}$F]fluoride, using HPLC or an SPE-cartridge, due to the large differences in physical-chemical properties. The possible side-reaction consisting of fluorodemethylation on the trimethylammonium group, leading to volatile [$^{18}$F]fluoromethane, is a limiting factor in the use of this leaving-group. Again, fluorine, in spite of its excellent leaving-group ability, is seldom used in fluorine-18 chemistry because of obvious isotopic dilution, leading to low specific radioactivity.

Aromatic nucleophilic radiofluorinations are usually performed in aprotic polar solvents, such as DMSO, sulfolane or dimethylacetamide, and often under basic conditions (due for example to the presence of Kryptofix-222®/potassium carbonate). Completion of the [$^{18}$F]fluoride incorporation often requires moderate to high temperatures (100° C.-170° C.) for ten to thirty minutes. Microwave technology can be a successful application here resulting in improved yields and shorter reaction times.

Said one-step nucleophilic [$^{18}$F]fluorination in the aromatic series is more particularly illustrated in example 45.

Typical example 5: Two-step process involving a nucleophilic [$^{18}$F]fluorination in the aromatic series followed by a (multi)deprotection step.

A typical pathway also often proposed for the labelling with fluorine-18 of [$^{18}$F]fluoroaryl derivatives (compounds of formula (I), (Ia), (Ib), (Ic) or (Id)) is a two-step radiochemical process, involving first a direct substitution of an appropriated atom or group (a leaving part) by [$^{18}$F]fluoride (as described above) followed by a (multi)deprotection step. (Multi)Deprotection step is usually performed under basic or acidic conditions and depends on the chemical nature of the protective groups. Heating the reaction mixture for a few minutes may be required.

Typical example 6: Three-step process involving a nucleophilic [$^{18}$F]fluorination (in the aromatic or aliphatic series) followed by a (multi)deprotection step and a coupling step.

A possible pathway also proposed for the labelling with fluorine-18 of [$^{18}$F]fluoroalkyl or [$^{18}$F]fluoroaryl derivatives (compound of formula (I), (Ia), (Ib), (Ic) or (Id)) is a three-step radiochemical process, involving first a direct substitution of an appropriated atom or group (a leaving part) by [$^{18}$F]fluoride (as described above), followed by a (multi) deprotection step and a coupling step.

Said three-step process is more particularly illustrated in example 44.

The invention also relates to a method for preparing a [$^{18}$F]radiolabelled compound according to the general formula (I), (Ia), (Ib), (Ic) or (Id) comprising at least the steps of i) reacting a dedicated precursor for labelling with a source of [$^{18}$F]fluoride in an appropriate solvent and optionally ii) recovering the obtained [$^{18}$F]radiolabelled compound according to the general formula (I), (Ia), (Ib), (Ic) or (Id).

The method for preparing the [$^{18}$F]radiolabelled compounds of general formula (I), (Ia), (Ib), (Ic) or (Id) can take place over a wide range of temperatures, and the precise reactions temperatures are not critical to the invention. In general, it is convenient to carry out the reactions at a temperature of from about 50° C. to about 150° C. The time required for the reactions may also vary widely, depending on many factors, notably the reactions temperatures and the nature of the reagents. However, provided that the reactions are effected under the preferred conditions outlined above, a period of from about 5 minutes to about 15 minutes will usually suffice. The [$^{18}$F]radiolabelled compound of general formula (I), (Ia), (Ib), (Ic) or (Id) thus prepared may be recovered from the reaction mixture by conventional means. For example, the compounds may be recovered by filtration on a pre-packed separation column. Additionally, the product can, if desired, be further purified by various well known techniques, such as chromatography techniques, notably High Performance Liquid Chromatography (HPLC).

The trialkylstannane precursor compounds of the compounds of formulae (I), (Ia), (Ib), (Ic) and (Id) also form part of the present invention. They are referred to as compounds of formula (Va) and (Vb):

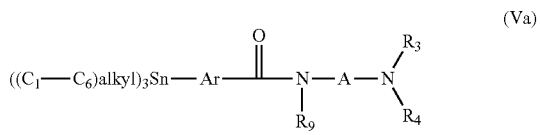

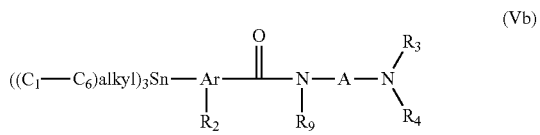

in which R$_2$, R$_3$, R$_4$, R$_9$ and A have the same meaning as above.

The following examples illustrate the invention.

Column chromatography was performed with Merck neutral aluminium oxide 90 standardized (63-200 µm) or silica gel A normal phase (35-70 µm). Thin layer chromatography was performed on Merck neutral aluminium oxide 60F$_{254}$ plates or Merck silica gel 60F$_{254}$ plates. The plates were visualized with UV light (254 nm) and/or by development with iodine, nynhydrin or potassium permanganate. Melting points were determined on an electrothermal IA9300 (capillary) or a Reichert-Jung-Koffler apparatus and were not corrected. NMR spectra (400 or 200 MHz) for $^1$H were recorded on a Bruker Avance 400 or Bruker Avance 200 instruments using CDCl$_3$, or DMSO-d$_6$ as solvent. Infrared spectra were recorded in KBr pellets or in CCl$_4$ on a FTIR Nicolet impact 410 or an FT vector 22 instrument (ν expressed in cm$^{-1}$). Mass spectra (MS) were obtained in electron impact mode on 5989A instruments (Agilent Technologies). Electrospray ionization mass spectra (ESI-MS) were obtained on a TSQ 7000 ThermoQuest Finnigam (Les Ulis, France). The samples were analyzed in CH$_3$OH/H$_2$O (1/1, v/v, containing 1% HCOOH) or CH$_3$CN/H$_2$O (1/1, v/v, containing 1% HCOOH) in positive mode or in CH$_3$OH/H$_2$O (1/1, v/v, containing 1% NH$_4$OH) in negative mode, at a final concentration of 8-12 pmol/μL. Each ESI-MS spectrum was recorded by averaging 10 spectra. Microanalyses were performed by Analytical Laboratory of the CNRS (Vernaison, France) for the elements indicated and were within 0.4% of the theoretical values unless indicated. All air-sensitive reactions were run under argon atmosphere. All solvents were dried using common techniques.

In the following examples,
Compounds ethyl 6-iodoquinoline-2-carboxylate (66), ethyl 6-iodonaphthalene-2-carboxylate (69), and ethyl 8-iodo-[1,6]naphthyridine-2-carboxylate (72) were prepared according to Chezal, J. M.; Papon, J.; Labarre, P.; Lartigue, C.; Galmier, M. J.; Decombat, C.; Chavignon, O.; Maublant, J.; Teulade, J. C.; Madelmont, J. C.; Moins, N. Evaluation of radiolabelled (hetero)aromatic analogues of N-(2-diethylaminoethyl)-4-iodobenzamide for imaging and targeted radionuclide therapy of melanoma. *J. Med. Chem.*, 2008, 51, 3133-3144.

Compounds 2-fluoroisonicotinic acid (27) and 2-fluoro-4-picoline (41) were prepared according to Ashimori, A.; Ono, T.; Uchida, T.; Ohtaki, Y.; Fukaya, C.; Watanabe, M.; Yokoyama, K. Novel 1,4-dihydropyridine calcium antagonists. I. Synthesis and hypotensive activity of 4-(substituted Pyridyl)-1,4-dihydropyridine derivatives. *Chem. Pharm. Bull.*, 1990, 38(9), 2446-2458.

Compounds ethyl 7-iodoacridone-4-carboxylate (78) and methyl 6-iodoanthranilate (97) were prepared according to Desbois, N.; Gardette, M.; Papon, J.; Labarre, P.; Maisonial, A.; Auzeloux, P.; Lartigue, C.; Bouchon, B.; Debiton, E.; Blache, Y.; Chavignon, O.; Teulade, J. C.; Maublant, J.; Madelmont, J. C.; Moins, N.; Chezal, J. M. Design, synthesis and preliminary biological evaluation of acridine compounds as potential agents for a combined targeted chemo-radionuclide therapy approach to melanoma. *Bioorg. Med. Chem.* 2008, 16, 7671-7690.

EXAMPLE 1

N-[2-[N-ethyl-N-[2-(2-fluoropyridin-3-yloxy)ethyl]amino]ethyl]-6-iodoquinoxaline-2-carboxamide dihydrochloride salt (11)

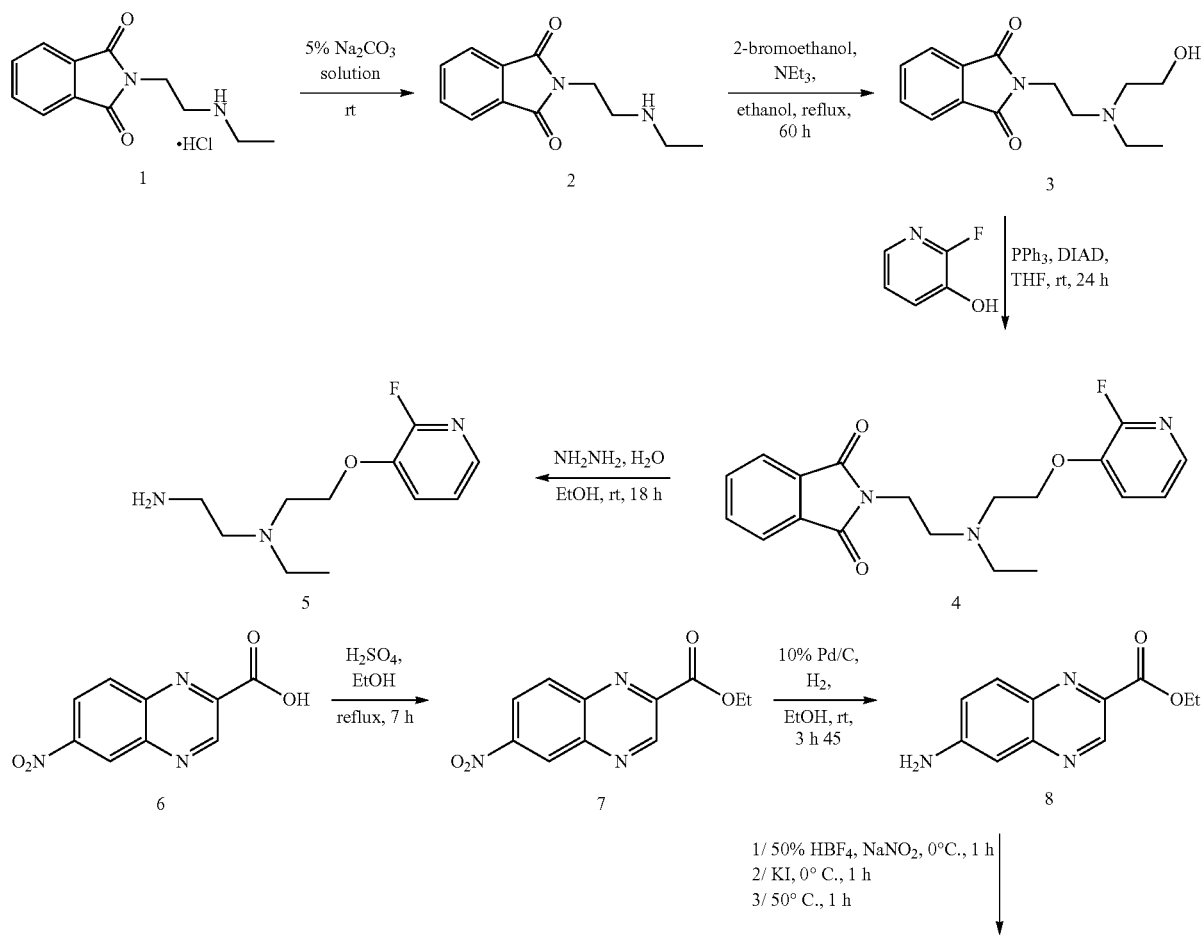

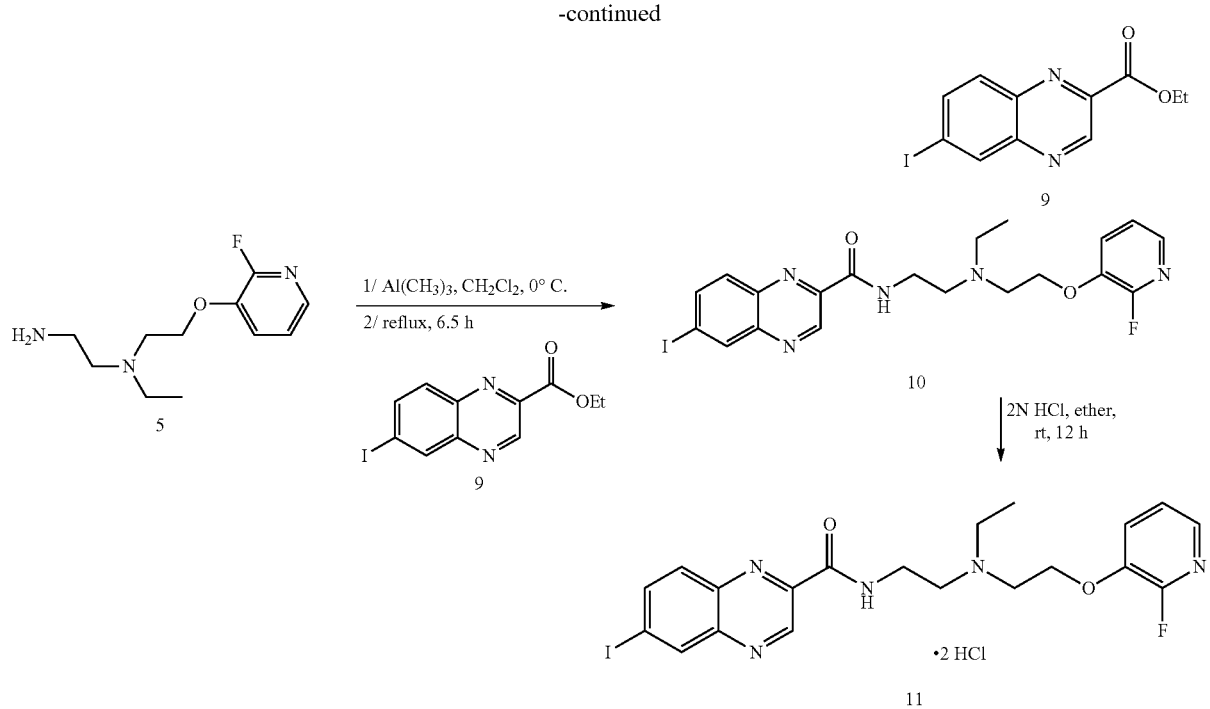

N-[2-(ethylamino)ethyl]phthalimide (2)

A suspension of N-[2-(ethylamino)ethyl]phthalimide hydrochloride salt (1) (2.00 g, 7.86 mmol) (Jones, J. H.; Holtz, W. J.; Cragoe, E. J. 6-Substituted 5-chloro-1,3-dihydro-2H-imidazo[4,5-b]pyrazin-2-ones with hypotensive activity. *J. Med. Chem.* 1973, 16, 537-42) in dichloromethane (100 mL) was washed with a 5% aqueous sodium carbonate solution (5 mL). The mixture was extracted with dichloromethane (40 mL). The organic layers were combined, dried on magnesium sulfate, filtered and evaporated under vacuum to give compound 2 (1.41 g, 6.47 mmol) as a yellow solid. Yield 82%; mp 111-113° C. (dec.); IR (KBr) ν 1292, 1395, 1430, 1541, 1637, 1712, 2929, 3200-3600 $cm^{-1}$; $^1$H NMR (200 MHz, $CDCl_3$) δ 1.07 (t, 3H, J=7.1 Hz), 2.68 (q, 2H, J=7.1 Hz), 2.92 (t, 2H, J=6.5 Hz), 3.81 (t, 2H, J=6.5 Hz), 7.68 (m, 2H), 7.82 (m, 2H).

N-[2-[N-ethyl-N-(2-hydroxyethyl)amino]ethyl]phthalimide (3)

To a solution of compound 2 (15.00 g, 68.7 mmol) in anhydrous ethanol (300 mL) were successively added, under argon, 2-bromoethanol (14.8 mL, 0.21 mol) and triethylamine (29.0 mL, 0.21 mol). The mixture was stirred under reflux for 60 h. After cooling to room temperature, the solvent was evaporated under vacuum and the residue was chromatographed ($SiO_2$, AcOEt/EtOH, 99/1, v/v) to give compound 3 (13.00 g, 49.6 mmol) as a white solid. Yield 72%; $R_f$ ($SiO_2$, AcOEt/EtOH, 99/1, v/v) 0.49; mp 56-58° C.; IR (KBr) ν 1018, 1387, 1405, 1702, 2825, 2959, 3400-3600 $cm^{-1}$; $^1$H NMR (200 MHz, $CDCl_3$) δ 0.93 (t, 3H, J=7.1 Hz), 2.58 (q, 2H, J=7.1 Hz), 2.68 (t, 2H, J=5.3 Hz), 2.76 (t, 2H, J=6.2 Hz), 3.11 (se, 1H), 3.53 (t, 2H, J=5.3 Hz), 3.77 (t, 2H, J=6.2 Hz), 7.71 (m, 2H), 7.82 (m, 2H); MS m/z 262 ($M^+$, 1), 231 (11), 174 (21), 130 (8), 102 (100), 76 (10), 58 (29).

N-[2-[N-ethyl-N-[2-(2-fluoropyridin-3-yloxy)ethyl]amino]ethyl]phthalimide (4)

To a solution of compound 3 (1.65 g, 6.29 mmol) in anhydrous tetrahydrofuran (THF, 80 mL) were successively added, under argon, 2-fluoro-3-hydroxypyridine (0.72 g, 6.37 mmol) (Dollé, F.; Valette, H.; Bottlaender, M.; Hinnen, F.; Vaufrey, F.; Guenther, I.; Crouzel, C. Synthesis of 2-[$^{18}$F]fluoro-3-[2(S)-2-azetidinylmethoxy]pyridine, a highly potent radioligand for in vivo imaging central nicotinic acetylcholine receptors. *J. Label. Compds. Radiopharm.* 1998, 41, 451-463), triphenylphosphine (1.65 g, 6.29 mmol) and dropwise diisopropyl azodicarboxylate (DIAD, 1.71 mL, 8.68 mmol). The mixture was stirred at room temperature for 24 h. The solvent was evaporated under reduced pressure and the residue was chromatographed ($Al_2O_3$, AcOEt) to give compound 4 (1.77 g, 4.95 mmol) as a yellow solid. Yield 79%; $R_f$ ($Al_2O_3$, AcOEt) 0.84; mp 58-60° C.; IR (KBr) ν 1192, 1240, 1290, 1395, 1452, 1712, 2847, 2943 $cm^{-1}$; $^1$H NMR (200 MHz, $CDCl_3$) δ 1.29 (t, 3H, J=7.1 Hz), 2.97 (q, 2H, J=7.1 Hz), 3.14 (t, 2H, J=6.5 Hz), 3.24 (t, 2H, J=5.9 Hz), 4.08 (t, 2H, J=6.5 Hz), 4.31 (t, 2H, J=5.9 Hz), 7.35 (ddd, 1H, $^5J_{H-F}$=0.9 Hz, J=4.8, 7.8 Hz), 7.52 (ddd, 1H, $^4J_{H-F}$=10.0 Hz, J=1.6, 7.8 Hz), 7.97 (m, 3H), 8.07 (m, 2H); MS m/z 357 ($M^+$, 1), 231 (15), 197 (100), 174 (23), 130 (10), 85 (17), 76 (10), 57 (45).

N-(2-aminoethyl)-N-ethyl-N-[2-(2-fluoropyridin-3-yloxy)ethyl]amine (5)

To a solution of compound 4 (1.50 g, 4.20 mmol) in ethanol (135 mL) was added hydrazine monohydrate (2.04 mL, 42.0 mmol). The mixture was stirred at room temperature for 14 h. The precipitate was filtered and then washed with ethanol (2×10 mL). The filtrate was evaporated under vacuum and the residue was chromatographed (Al$_2$O$_3$, CH$_2$Cl$_2$/EtOH, 9/1, v/v) to give compound 5 (949 mg, 4.18 mmol) as a yellow oil. Yield 99%; R$_f$ (Al$_2$O$_3$, CH$_2$Cl$_2$/EtOH, 9/1, v/v) 0.36; IR (CCl$_4$) ν 1120, 1190, 1250, 1283, 1453, 1466, 2700-3000 cm$^{-1}$; $^1$H NMR (200 MHz, CDCl$_3$) δ 1.08 (t, 3H, J=7.1 Hz), 1.54 (se, 2H), 2.67 (m, 6H), 2.94 (t, 2H, J=6.0 Hz), 4.12 (t, 2H, J=6.0 Hz), 7.13 (ddd, 1H, $^5$J$_{H-F}$=0.9 Hz, J=4.8, 7.9 Hz), 7.32 (ddd, 1H, $^4$J$_{H-F}$=10.1 Hz, J=1.6, 7.9 Hz), 7.76 (td, 1H, $^4$J$_{H-F}$=1.6 Hz, J=1.6, 4.8 Hz); ESI-MS m/z 227.9 [M+H]$^+$.

Ethyl 6-nitroquinoxaline-2-carboxylate (7)

To a solution of 6-nitroquinoxaline-2-carboxylic acid (6) (5.00 g, 22.8 mmol) (Higashida, S.; Sakurai, M.; Yabe, Y.; Nishihgaki, T.; Komai, T.; Handa, H. Preparation of peptide inhibitors of HIV protease, peptides capable of inhibiting the activity of HIV protease, their preparation and their therapeutic use. European Patent, EP 0 587 311, 1994) in dry ethanol (50 mL), was added under argon, concentrated sulfuric acid (750 μL). After being stirred at reflux for 7 h, the reaction mixture was cooled to room temperature and a saturated aqueous sodium carbonate solution (50 mL) was added. The solution was extracted with dichloromethane (3×30 mL) and the combined organic layers were dried on magnesium sulfate, filtered and evaporated to dryness to afford ester 7 (3.79 g, 15.3 mmol) as a brown solid. Yield 67%; mp 221-223° C.; IR (KBr) ν 1282, 1347, 1531, 1741 cm$^{-1}$; $^1$H NMR (200 MHz, CDCl$_3$) δ 1.58 (t, 3H, J=7 Hz), 4.68 (q, 2H, J=7 Hz), 8.53 (d, 1H, J=9 Hz), 8.68 (dd, 1H, J=2.5, 9 Hz), 9.14 (d, 1H, J=2.5 Hz), 9.72 (s, 1H); MS m/z 248 (M$^+$1, 4), 203 (36), 175 (100), 128 (23), 101 (32), 75 (24).

Ethyl 6-aminoquinoxaline-2-carboxylate (8)

To a flask containing compound 7 (2.93 g, 11.9 mmol) in ethanol (500 mL) was added 10% Pd/C (300 mg). The mixture was degassed and stirred under a H$_2$ atmosphere for 3 h 45. The catalyst was removed by filtration through Celite® 545, washed with ethanol (50 mL) and the filtrate was evaporated. The resulting crude product was purified by chromatography (Al$_2$O$_3$, CH$_2$Cl$_2$/EtOH, 99/1, v/v) to afford the title product 8 (1.69 g, 7.79 mmol) as a dark yellow solid. Yield 66%; R$_f$(Al$_2$O$_3$, CH$_2$Cl$_2$/EtOH, 99/1, v/v) 0.55; mp 181-183° C.; IR (KBr) ν 1299, 1487, 1613, 1701, 3202, 3431 cm$^{-1}$; $^1$H NMR (200 MHz, CDCl$_3$) δ 1.49 (t, 3H, J=7 Hz), 4.38 (m, 2H), 4.56 (q, 2H, J=7 Hz), 7.16 (d, 1H, J=2.5 Hz), 7.26 (dd, 1H, J=2.5, 9 Hz), 8.05 (d, 1H, J=9 Hz), 9.35 (s, 1H); MS m/z 217 (M$^+$, 23), 145 (100), 117 (19), 90 (16), 63 (14).

Ethyl 6-iodoquinoxaline-2-carboxylate (9)

To a mixture of compound 8 (1.37 g, 6.31 mmol) in a 50% aqueous fluoroboric acid solution (10 mL), at 0° C., was added dropwise, a solution of sodium nitrite (480 mg, 6.96 mmol) in water (3 mL). The reaction mixture was stirred for an additional hour at 0° C. and a solution of potassium iodide (1.57 g, 9.46 mmol) in water (5 mL) was added. The reaction was stirred at 0° C. for 1 h and then warmed at 50° C. until no more gas evolution was observed (1 h). After cooling to room temperature, the mixture was basified with a saturated aqueous sodium carbonate solution (60 mL) and extracted with dichloromethane (3×40 mL). The combined organic layers were washed with a 5% aqueous sodium bisulfite solution (2×30 mL), dried on magnesium sulfate, filtered and concentrated under vacuum. The crude product was purified by chromatography (Al$_2$O$_3$, CH$_2$Cl$_2$) to give compound 9 (0.68 g, 2.07 mmol) as a yellow solid. Yield 33%; R$_f$ (Al$_2$O$_3$, CH$_2$Cl$_2$) 0.80; mp 160-162° C.; IR (KBr) ν 1103, 1151, 1230, 1237, 1717 cm$^{-1}$; $^1$H NMR (400 MHz, CDCl$_3$) δ 1.51 (t, 3H, J=7 Hz), 4.59 (q, 2H, J=7 Hz), 7.99 (d, 1H, J=9 Hz), 8.10 (dd, 1H, J=2.9 Hz), 8.62 (d, 1H, J=2 Hz), 9.51 (s, 1H); MS m/z 328 (M$^+$, 19), 284 (43), 256 (100), 128 (29), 101 (50), 75 (30).

N-[2-[N-ethyl-N-[2-(2-fluoropyridin-3-yloxy)ethyl] amino]ethyl]-6-iodoquinoxaline-2-carboxamide (10)

To a stirred solution of compound 5 (55 mg, 0.24 mmol) in anhydrous dichloromethane (3 mL) was added at 0° C., under argon, a 2.0 M trimethylaluminium solution in heptane (0.12 mL, 0.24 mmol). After 10 min, a solution of compound 9 (57 mg, 0.17 mmol) in anhydrous dichloromethane (2 mL) was added and the mixture was refluxed for 6.5 h. After cooling to room temperature, water (15 mL) was added. The mixture was decanted and the aqueous layer was extrated with dichloromethane (3×20 mL). The organic layers were combined, dried on magnesium sulfate, filtered and evaporated under reduced pressure. The residue obtained was chromatographed (Al$_2$O$_3$, CH$_2$Cl$_2$/EtOH, 98/2, v/v) to give compound 10 (84 mg, 0.16 mmol) as a brown oil. Yield 94%; R$_f$(Al$_2$O$_3$, CH$_2$Cl$_2$/EtOH, 98/2, v/v) 0.58; IR (CCl$_4$) ν 1453, 1468, 1522, 1684, 2750-3000 cm$^{-1}$; $^1$H NMR (400 MHz, CDCl$_3$) δ 1.12 (t, 3H, J=6.8 Hz), 2.76 (q, 2H, J=6.8 Hz), 2.89 (t, 2H, J=5.7 Hz), 3.03 (t, 2H, J=5.3 Hz), 3.64 (q, 2H, J=5.7 Hz), 4.15 (t, 2H, J=5.3 Hz), 6.99 (dd, 1H, J=4.8, 7.3 Hz), 7.23 (m, 1H), 7.59 (d, 1H, J=8.8 Hz), 7.64 (m, 1H), 8.00 (d, 1H, J=8.8 Hz), 8.43 (se, 1H), 8.57 (s, 1H), 9.61 (s, 1H); ESI-MS m/z 509.9 [M+H]$^+$.

N-[2-[N-ethyl-N-[2-(2-fluoropyridin-3-yloxy)ethyl] amino]ethyl]-6-iodoquinoxaline-2-carboxamide dihydrochloride salt (11)

To a solution of compound 10 (0.23 g, 0.45 mmol) in anhydrous dichloromethane (5 mL) was added, under argon, a 2.0 N hydrochloric acid solution in anhydrous ether (10 mL). The mixture was stirred at room temperature for 10 min and the solvent was evapored under vacuum. The residue was then suspended in anhydrous ether (10 mL) and the mixture was stirred, under argon, at room temperature for one night. The precipitate was collected by filtration to give compound 11 (0.24 g, 0.41 mmol) as a very hygroscopic beige solid. Yield 91%; mp 99-101° C. (dec.); IR (KBr) ν 1464, 1533, 1560, 1671, 2400-2700, 2800-3100, 3200-3400 cm$^{-1}$; $^1$H NMR (200 MHz, DMSO-d$_6$) δ 1.31 (t, 3H, J=7.0 Hz), 3.40 (m, 4H), 3.78 (m, 4H), 4.19 (m, 6H), 4.55 (t, 2H, J=3.5 Hz), 7.28 (dd, 1H, J=5.3, 7.7 Hz), 7.70 (m, 2H), 7.90 (d, 1H, J=8.8 Hz), 8.25 (dd, 1H, J=1.9, 8.8 Hz), 8.64 (d, 1H, J=1.8 Hz), 9.40 (m, 2H), 10.53 (se, 1H); ESI-MS m/z 509.9 [M+H]$^+$; Anal. Calcd for C$_{20}$H$_{21}$O$_2$IN$_5$F, 2HCl, H$_2$O: C, 40.02; H, 4.20; N, 11.67. Found: C, 40.40; H, 4.34; N, 11.28.

EXAMPLE 2

N-[2-[N-ethyl-N-[2-[(6-fluoropyridin-2-yl)amino]ethyl]amino]ethyl]-6-iodoquinoxaline-2-carboxamide dihydrochloride salt (17)

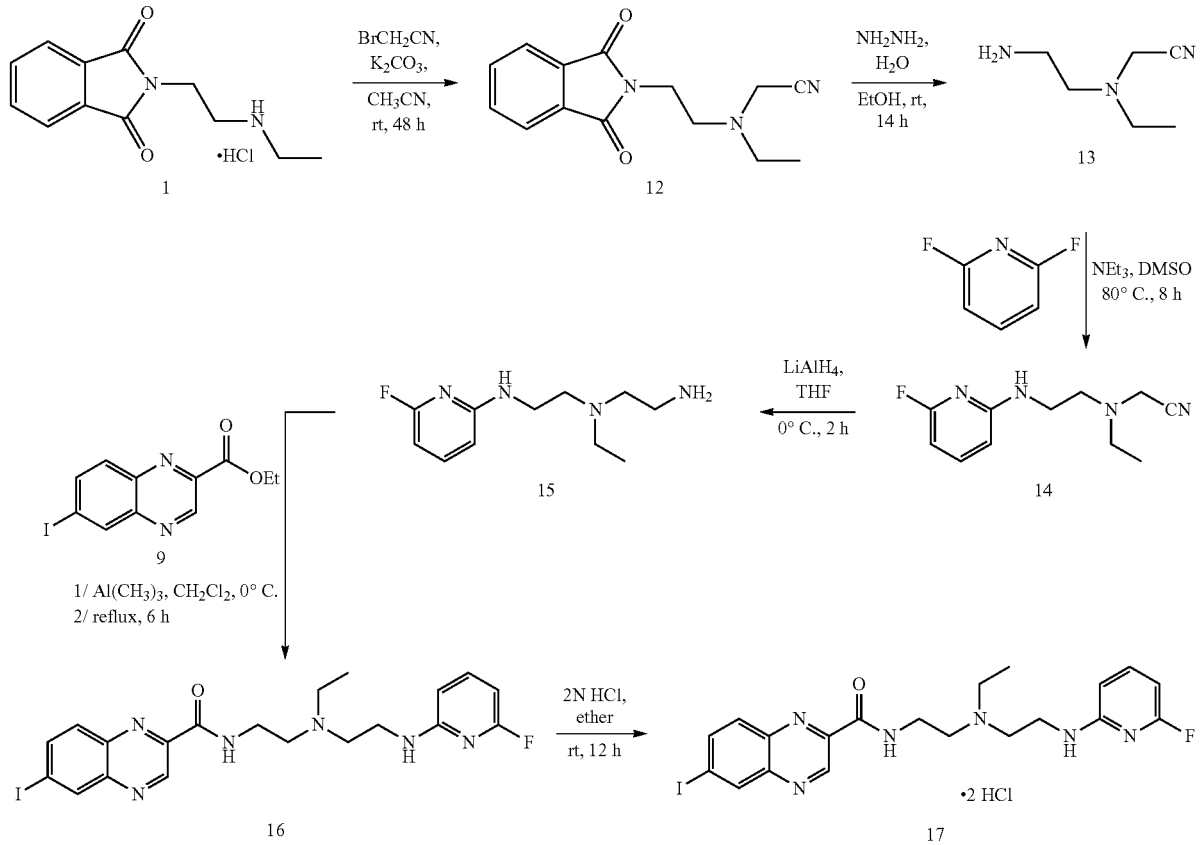

N-[2-[(N-cyanomethyl-N-ethyl)amino]ethyl]phthalimide (12)

To a solution of compound 1 (10.00 g, 39.3 mmol) in anhydrous acetonitrile (160 mL) were added successively, under argon, potassium carbonate (5.43 g, 39.3 mmol) and bromoacetonitrile (2.72 mL, 39.3 mmol). The mixture was stirred at room temperature for 48 h. The precipitate was filtered and the filtrate was evaporated under vacuum. The residue was chromatographed ($Al_2O_3$, $CH_2Cl_2$) to give compound 12 (8.24 g, 32.0 mmol) as a beige solid. Yield 82%; $R_f$ ($Al_2O_3$, $CH_2Cl_2$) 0.94; mp 80-82° C.; IR (KBr) v 1100, 1322, 1356, 1398, 1420, 1708, 1767, 2235, 2846, 2979 $cm^{-1}$; $^1$H NMR (200 MHz, $CDCl_3$) δ 0.92 (t, 3H, J=7.1 Hz), 2.55 (q, 2H, J=7.1 Hz), 2.79 (t, 2H, J=6.1 Hz), 3.65 (s, 2H), 3.75 (t, 2H, J=6.1 Hz), 7.67 (m, 2H), 7.78 (m, 2H); MS m/z 257 ($M^+$, 2), 97 (100), 76 (12), 69 (23).

[N-(2-aminoethyl)-N-ethyl]aminoacetonitrile (13)

This compound was prepared, starting from compound 12 (2.78 g, 10.8 mmol), according to the procedure developed for compound 5. Reaction time at room temperature: 14 h; the purification was performed using column chromatography ($Al_2O_3$, $CH_2Cl_2$/EtOH, 9/1, v/v) to give compound 13 (1.17 g, 9.20 mmol) as a yellow oil. Yield 85%; $R_f$($Al_2O_3$, $CH_2Cl_2$/EtOH, 9/1, v/v) 0.25; IR ($CCl_4$) v 1321, 1427, 1459, 1664, 2240, 2829, 2940, 2975 $cm^{-1}$; $^1$H NMR (400 MHz, $CDCl_3$) δ 1.01 (t, 3H, J=7.1 Hz), 1.97 (se, 2H), 2.50 (m, 4H), 2.70 (t, 2H, J=5.5 Hz), 3.52 (s, 2H); ESI-MS m/z 128.5 $[M+H]^+$.

N-ethyl-N-[2-[(6-fluoropyridin-2-yl)amino]ethyl]aminoacetonitrile (14)

To a stirred solution of compound 13 (1.90 g, 14.9 mmol) in anhydrous dimethylsulfoxide (DMSO, 40 mL) were successively added, under argon, 2,6-difluoropyridine (2.05 mL, 22.4 mmol) and triethylamine (3.15 mL, 22.4 mmol). The mixture was heated at 80° C. for 8 h. After cooling to room temperature, water (400 mL) was added. The mixture was decanted and the aqueous layer was extracted with dichloromethane (3×100 mL). The organic layers were combined, washed with a brine solution (3×150 mL), dried on magnesium sulfate, filtered and evaporated under vacuum. The residue was chromatographed ($Al_2O_3$, AcOEt/cyclohexane, 1/1, v/v) to give compound 14 (1.29 g, 5.82 mmol) as a brown oil. Yield 39%; $R_f$($Al_2O_3$, AcOEt/cyclohexane, 1/1, v/v) 0.53; IR ($CCl_4$) v 1228, 1423, 1457, 1500, 1577, 1620, 2750-3000, 3422 $cm^{-1}$; $^1$H NMR (400 MHz, $CDCl_3$) δ 1.13 (t, 3H, J=7.1 Hz), 2.67 (q, 2H, J=7.1 Hz), 2.83 (t, 2H, J=5.9 Hz), 3.38 (t, 2H, J=5.9 Hz), 3.64 (s, 2H), 5.00 (se, 1H), 6.14 (dd, 1H, J=2.4, 7.9 Hz), 6.21 (dd, 1H, J=2.4, 7.9 Hz), 7.47 (q, 1H, $^4J_{H-F}$=7.9 Hz, J=7.9 Hz): MS m/z 222 ($M^+$, 5), 125 (31), 97 (100), 69 (22).

N-(2-aminoethyl)-N-ethyl-N-[2-[N-(6-fluoropyridin-2-yl)amino]ethyl]amine (15)

To a solution of lithium aluminium hydride (288 mg, 7.58 mmol) in anhydrous tetrahydrofuran (20 mL) was added under argon, at 0° C., a solution of compound 14 (1.12 g, 5.04 mmol) in anhydrous tetrahydrofuran (10 mL). The mixture was stirred 0° C. for 2 h. Then water (388 µL), a 3.0 N aqueous sodium hydroxide solution (388 µL) and water (388 µL) were successively added to the mixture until no more gas evolution was observed. The precipitate was filtered and the filtrate was dried on magnesium sulfate, filtered and evaporated under vacuum. The residue was chromatographed ($Al_2O_3$, $CH_2Cl_2$/EtOH/$NH_4OH$, 80/19/1, v/v/v) to give compound 15 (0.55 g, 2.43 mmol) as a brown oil. Yield 48%; IR ($CCl_4$) ν 1227, 1456, 1501, 1621, 2750-3000 cm$^{-1}$; $^1$H NMR (200 MHz, $CDCl_3$) δ 0.97 (t, 3H, J=7.0 Hz), 2.08 (se, 2H), 2.59 (m, 8H), 3.25 (q, 2H, J=5.5 Hz), 5.39 (se, 1H), 6.05 (ddd, 1H, $^3J_{H-F}$=0.6 Hz, J=2.4, 7.8 Hz), 6.17 (ddd, 1H, $^5J_{H-F}$=0.4 Hz, J=2.4, 7.8 Hz), 7.39 (q, 1H, $^4J_{H-F}$=7.8 Hz, J=7.8 Hz); MS m/z 227 (M+1, 1), 196 (15), 139 (60), 114 (17), 101 (61), 96 (17), 72 (27), 58 (100).

N-[2-[N-ethyl-N-[2-[(6-fluoropyridin-2-yl)amino]ethyl]amino]ethyl]-6-iodoquinoxaline-2-carboxamide (16)

This compound was prepared, starting from compound 15 (55 mg, 0.24 mmol), according to the procedure developed for compound 10. Reaction time under reflux: 6 h, to give compound 16 (84 mg, 0.16 mmol) as an orange-coloured oil. Yield 97%; $R_f$ ($Al_2O_3$, $CH_2Cl_2$/EtOH, 98/2, v/v) 0.70; IR ($CCl_4$) ν 1521, 1619, 1685, 2760-3000, 3405 cm$^{-1}$; $^1$H NMR (400 MHz, $CDCl_3$) δ 1.09 (t, 3H, J=7.1 Hz), 2.72 (q, 2H, J=7.1 Hz), 2.82 (m, 2H), 3.35 (q, 2H, J=5.7 Hz), 3.63 (q, 2H, J=5.9 Hz), 5.40 (se, 1H), 6.01 (dd, 1H, J=2.3, 8.0 Hz), 6.11 (dd, 1H, J=2.3, 8.0 Hz), 7.30 (q, 1H, $^4J_{H-F}$=8.0 Hz, J=8.0 Hz), 7.90 (d, 1H, J=8.8 Hz), 8.06 (dd, 1H, J=1.8, 8.8 Hz), 8.34 (se, 1H), 8.58 (d, 1H, J=1.8 Hz), 9.61 (s, 1H); ESI-MS m/z 508.9 [M+H]$^+$.

N-[2-[N-ethyl-N-[2-[(6-fluoropyridin-2-yl)amino]ethyl]amino]ethyl]-6-iodoquinoxaline-2-carboxamide dihydrochloride salt (17)

This compound was prepared, starting from compound 16 (251 mg, 0.49 mmol), according to the procedure developed for compound 11 to give compound 17 (231 mg, 0.40 mmol) as a very hygroscopic yellow solid. Yield 80%; mp 99-101° C. (dec.); IR (KBr) ν 1163, 1225, 1421, 1474, 1522, 1622, 1670, 2500-2800, 2850-3000, 3100-3600 cm$^{-1}$; $^1$H NMR (400 MHz, DMSO-d$_6$) δ 1.28 (t, 3H, J=7.0 Hz), 3.33 (q, 2H, J=6.6 Hz), 3.62 (m, 2H), 3.80 (m, 6H), 6.12 (dd, 1H, J=2.0, 8.0 Hz), 6.40 (dd, 1H, J=2.0, 8.0 Hz), 7.30 (se, 1H), 7.50 (q, 1H, $^4J_{H-F}$=8.0 Hz, J=8.0 Hz), 7.92 (d, 1H, J=8.8 Hz), 8.25 (dd, 1H, J=1.8, 8.8 Hz), 8.64 (d, 1H, J=1.6 Hz), 9.38 (t, 1H, J=6.0 Hz), 9.44 (s, 1H), 10.28 (se, 1H); ESI-MS m/z 509.1 [M+H]$^+$; Anal. Calcd for $C_{20}H_{22}OIN_6F$, 2HCl: C, 41.33; H, 4.16; N, 14.46. Found: C, 43.19; H, 4.31; N, 14.74.

EXAMPLE 3

N-[2-[[N-ethyl-N-(6-fluoropyridin-2-yl)]amino]ethyl]-6-iodoquinoxaline-2-carboxamide (20)

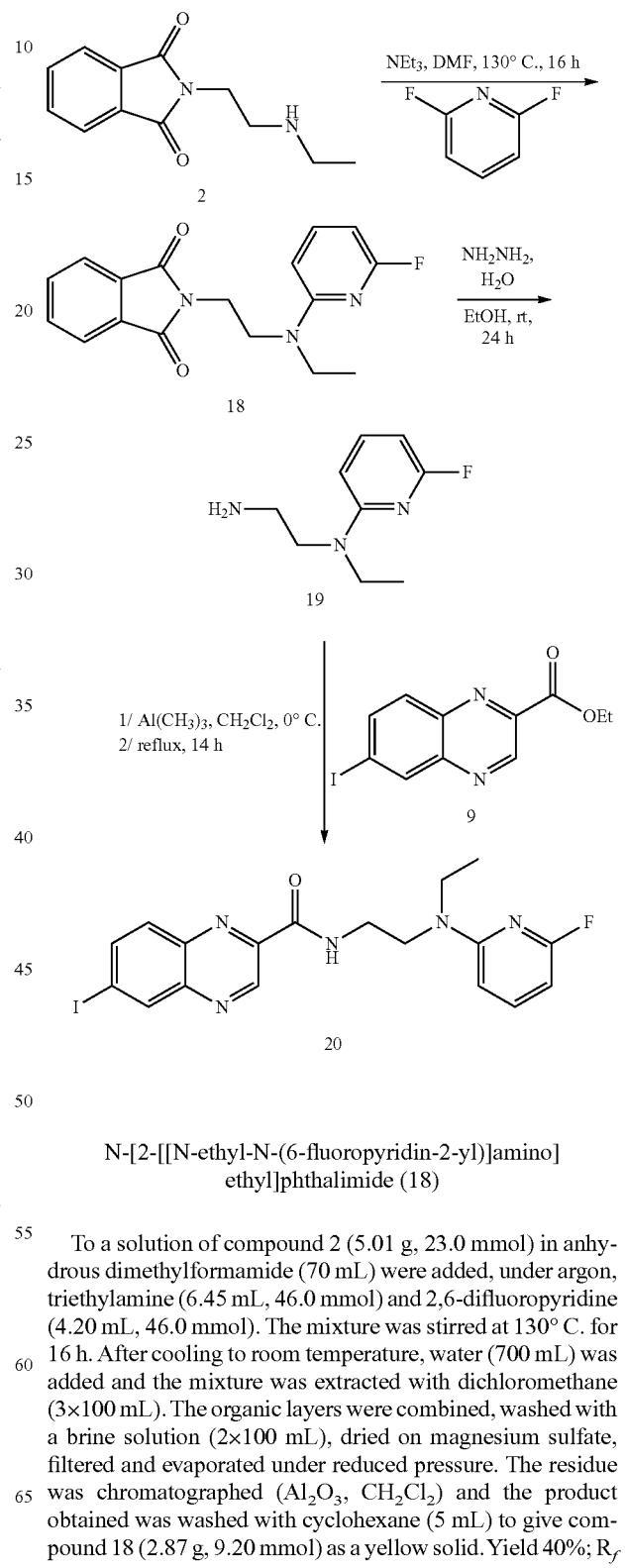

N-[2-[[N-ethyl-N-(6-fluoropyridin-2-yl)]amino]ethyl]phthalimide (18)

To a solution of compound 2 (5.01 g, 23.0 mmol) in anhydrous dimethylformamide (70 mL) were added, under argon, triethylamine (6.45 mL, 46.0 mmol) and 2,6-difluoropyridine (4.20 mL, 46.0 mmol). The mixture was stirred at 130° C. for 16 h. After cooling to room temperature, water (700 mL) was added and the mixture was extracted with dichloromethane (3×100 mL). The organic layers were combined, washed with a brine solution (2×100 mL), dried on magnesium sulfate, filtered and evaporated under reduced pressure. The residue was chromatographed ($Al_2O_3$, $CH_2Cl_2$) and the product obtained was washed with cyclohexane (5 mL) to give compound 18 (2.87 g, 9.20 mmol) as a yellow solid. Yield 40%; $R_f$ ($Al_2O_3$, $CH_2Cl_2$) 0.86; mp 115-117° C.; IR (KBr) ν 1399, 1438, 1498, 1612, 1706 cm$^{-1}$; $^1$H NMR (200 MHz, CDCl$_3$) δ 1.17 (t, 3H, J=7.1 Hz), 3.49 (q, 2H, J=7.1 Hz), 3.74 (t, 2H, J=6.2 Hz), 3.93 (t, 2H, J=6.2 Hz), 5.97 (dd, 1H, J=2.7, 8.0 Hz), 6.36 (dd, 1H, J=2.7, 8.0 Hz), 7.44 (q, 1H, $^4J_{H-F}$=8.0 Hz, J=8.0 Hz), 7.70 (m, 2H), 7.81 (m, 2H); MS m/z 313 (M$^+$, 8), 153 (100), 125 (50), 96 (22), 76 (15).

N-(2-aminoethyl)-N-ethyl-N-(6-fluoropyridin-2-yl) amine (19)

This compound was prepared, starting from compound 18 (0.60 g, 1.92 mmol), according to the procedure developed for compound 5. Reaction time at room temperature: 24 h to give compound 19 (0.28 g, 1.52 mmol) as brown oil. Yield 79%; $R_f$(Al$_2$O$_3$, CH$_2$Cl$_2$/EtOH, 9/1, v/v) 0.35; IR (CCl$_4$) ν 1240, 1440, 1501, 1617, 2800-3000 cm$^{-1}$; $^1$H NMR (200 MHz, CDCl$_3$) δ 1.16 (t, 3H, J=7.0 Hz), 1.59 (se, 2H), 2.92 (t, 2H, J=6.6 Hz), 3.49 (m, 4H), 6.04 (dd, 1H, J=2.6, 8.0 Hz), 6.28 (dd, 1H, J=2.6, 8.0 Hz), 7.43 (q, 1H, $^4J_{H-F}$=8.0 Hz, J=8.0 Hz); ESI-MS m/z 183.8 [M+H]$^+$.

N-[2-[[N-ethyl-N-(6-fluoropyridin-2-yl)]amino] ethyl]-6-iodoquinoxaline-2-carboxamide (20)

This compound was prepared, starting from compound 19 (0.21 g, 1.13 mmol), according to the procedure developed for compound 10. Reaction time under reflux: 14 h; the purification was performed using column chromatography (Al$_2$O$_3$, CH$_2$Cl$_2$) to give compound 20 (0.23 g, 0.49 mmol) as a yellow solid. Yield 61%; $R_f$ (Al$_2$O$_3$, CH$_2$Cl$_2$) 0.67; mp 133-135° C.; IR (KBr) ν 1162, 1505, 1618, 1677, 2800-3000, 3305 cm$^{-1}$; $^1$H NMR (200 MHz, DMSO-d$_6$) δ 1.11 (t, 3H, J=6.9 Hz), 3.56 (m, 6H), 6.15 (dd, 1H, J=2.7, 8.0 Hz), 6.61 (dd, 1H, J=2.7, 8.0 Hz), 7.60 (q, 1H, $^4J_{H-F}$=8.0 Hz, J=8.0 Hz), 7.89 (d, 1H, J=8.8 Hz), 8.25 (dd, 1H, J=1.9, 8.8 Hz), 8.62 (d, 1H, J=1.9 Hz), 9.24 (m, 1H), 9.44 (s, 1H); MS m/z 465 (M$^+$, 4), 166 (29), 153 (100), 125 (54), 96 (16).

EXAMPLE 4

N-[2-[[N-ethyl-N-(2-fluoroethyl)]amino]ethyl]-6-iodoquinoxaline-2-carboxamide dihydrochloride salt (26)

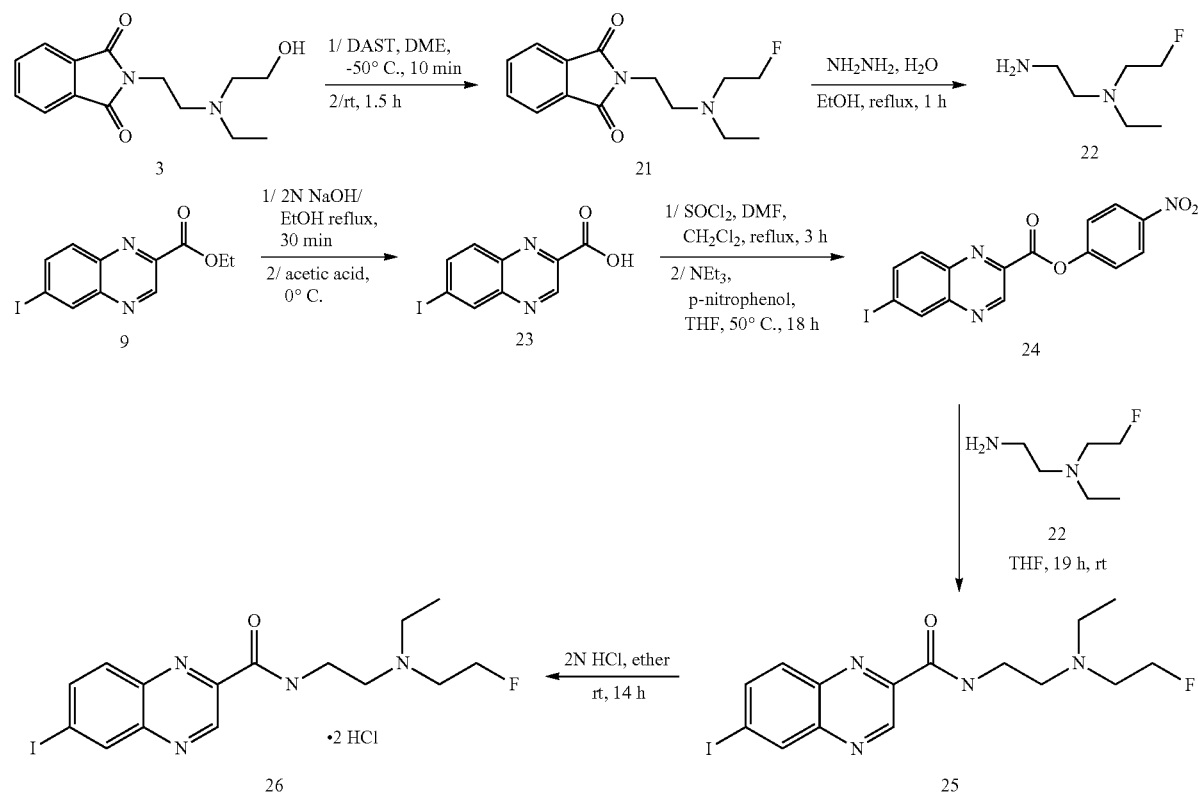

N-[2-[N-ethyl-N-(2-fluoroethyl)amino]ethyl]phthalimide (21)

To a solution of compound 3 (100 mg, 0.38 mmol) in dimethoxyethane (DME, 7 mL) was added at −50° C., under argon, (diethylamino)sulfur trifluoride (DAST, 100 μL, 0.76 mmol). The mixture was stirred at −50° C. for 10 min and then at room temperature for 1.5 h. Dichloromethane (5 mL) and a saturated aqueous sodium carbonate solution (5 mL) were then successively added. The organic layer was dried on magnesium sulfate, filtered and evaporated under vacuum. The residue was chromatographed (SiO$_2$, AcOEt/pentane, 1/1, v/v) to give compound 21 (51 mg, 0.19 mmol) as a white solid. Yield 50%; $R_f$(SiO$_2$, AcOEt/pentane, 1/1, v/v) 0.53; mp 57-59° C.; IR (KBr) ν 1023, 1403, 1715, 1769, 2700-3000 cm$^{-1}$; $^1$H NMR (200 MHz, CDCl$_3$) δ 1.00 (t, 3H, J=7.1 Hz), 2.68 (q, 2H, J=7.1 Hz), 2.86 (m, 4H), 3.78 (t, 2H, J=6.6 Hz), 4.47 (td, 2H, $^2J_{H\text{-}F}$=47.5 Hz, J=5.1 Hz), 7.70 (m, 2H), 7.83 (m, 2H); MS m/z 264 (M$^+$, 1), 104 (100), 76 (38), 56 (18).

N-(2-aminoethyl)-N-ethyl-N-(2-fluoroethyl)amine (22)

To a stirred solution of compound 21 (752 mg, 2.85 mmol) in anhydrous ethanol (30 mL) was added, under argon, hydrazine monohydrate (324 µL, 6.68 mmol). The mixture was refluxed for 1 h. After cooling to room temperature, the white precipitate was filtered and washed with ethanol (10 mL). The filtrate was evaporated under vacuum and the residue was chromatographed (Al$_2$O$_3$, CH$_2$Cl$_2$/EtOH/NH$_4$OH, 80/19/1, v/v/v) to give compound 22 (213 mg, 1.59 mmol) as an orange-coloured oil. Yield 56%; R$_f$ (Al$_2$O$_3$, CH$_2$Cl$_2$/EtOH/NH$_4$OH, 80/19/1, v/v/) 0.41; IR (CCl$_4$) ν 1034, 1453, 1684, 2700-3000 cm$^{-1}$; $^1$H NMR (400 MHz, CDCl$_3$) δ 1.01 (t, 3H, J=7.1 Hz), 2.59 (m, 4H), 2.74 (td, 2H, $^3J_{H\text{-}F}$=26.5 Hz, J=5.3 Hz), 2.78 (t, 2H, J=5.3 Hz), 4.30 (se, 2H), 4.46 (td, 2H, $^2J_{H\text{-}F}$=47.5 Hz, J=5.0 Hz).

6-iodoquinoxaline-2-carboxylic acid (23)

A solution of compound 9 (1.30 g, 3.96 mmol) in a 2.0 N sodium hydroxide/ethanol solution (1/1, v/v, 6 mL) was refluxed for 30 min. After cooling to room temperature, the reaction mixture was acidified (pH=4-5) with acetic acid and cooled to 0° C. The resulting precipitate was removed by filtration and dried in a vacuum oven to afford acid 23 (1.08 g, 3.29 mmol) as a white solid. Yield 91%; mp 242-244° C.; $^1$H NMR (200 MHz, DMSO-d$_6$) δ 7.97 (d, 1H, J=8 Hz), 8.15 (d, 1H, J=8 Hz), 8.52 (s, 1H), 9.36 (s, 1H); ESI-MS m/z 298.6 [M−H]$^-$.

p-nitrophenyl 6-iodoquinoxaline-2-carboxylate (24)

To a solution of compound 23 (200 mg, 0.67 mmol) in dry dichloromethane (10 mL), under argon and at 0° C., was added dropwise dry N,N-dimethylformamide (100 µL) and thionyl chloride (200 µL, 2.74 mmol). The reaction mixture was stirred at reflux for 3 h. After cooling to room temperature, the solvent was removed under reduced pressure to afford crude 6-iodoquinoxaline-2-carbonyl chloride. This was suspended in dry tetrahydrofuran (10 mL) and were successively added, under argon, p-nitrophenol (93 mg, 0.67 mmol) and dropwise a solution of triethylamine (95 µL, 0.68 mmol) in dry tetrahydrofuran (5 mL). The solution was stirred at 50° C. for 18 h. After cooling to room temperature, dichloromethane (30 mL) was added and the resulting solution was washed with a 5% aqueous sodium carbonate solution (20 mL). The aqueous layer was extracted with dichloromethane (5×15 mL) and the organic layers were combined, dried on magnesium sulfate and evaporated under reduced pressure. The resulting precipitate was triturated with ether (5 mL) and collected by filtration to afford ester 24 (225 mg, 0.53 mmol) as a beige solid. Yield 80%; mp 228-230° C.; $^1$H NMR (400 MHz, DMSO-d$_6$) δ 7.71 (d, 2H, J=7 Hz), 8.09 (d, 1H, J=9 Hz), 8.30 (dd, 1H, J=2, 9 Hz), 8.41 (d, 2H, J=7 Hz), 8.72 (d, 1H, J=2 Hz), 9.60 (s, 1H).

N-[2-[[N-ethyl-N-(2-fluoroethyl)]amino]ethyl]-6-iodoquinoxaline-2-carboxamide (25)

To a solution of compound 22 (110 mg, 0.80 mmol) in anhydrous tetrahydrofuran (15 mL) was added, under argon, ester 24 (200 mg, 0.48 mmol). The mixture was stirred at room temperature for 19 h. The solvent was then evaporated under vacuum and the residue was chromatographed (Al$_2$O$_3$, CH$_2$Cl$_2$/EtOH, 98/2, v/v) to give compound 25 (190 mg, 0.46 mmol) as an orange-coloured oil. Yield 96%; R$_f$ (Al$_2$O$_3$, CH$_2$Cl$_2$/EtOH, 98/2, v/v) 0.72; IR (CCl$_4$) ν 1474, 1522, 1685, 2855, 2927 cm$^{-1}$; $^1$H NMR (400 MHz, CDCl$_3$) δ 1.12 (t, 3H, J=7.1 Hz), 2.75 (q, 2H, J=7.1 Hz), 2.87 (t, 1H, J=6.0 Hz), 2.92 (td, 2H, $^3J_{H\text{-}F}$=26.8 Hz, J=5.0 Hz), 3.62 (q, 2H, J=6.0 Hz), 4.58 (td, 2H, $^2J_{H\text{-}F}$=47.7 Hz, J=5.0 Hz), 7.81 (d, 1H, J=8.8 Hz), 8.05 (dd, 1H, J=1.8, 8.8 Hz), 8.45 (se, 1H), 8.58 (d, 1H, J=1.8 Hz), 9.62 (s, 1H); MS m/z 416 (M$^+$, 1), 104 (100), 76 (12), 56 (8).

N-[2-[[N-ethyl-N-(2-fluoroethyl)]amino]ethyl]-6-iodoquinoxaline-2-carboxamide dihydrochloride salt (26)

This compound was prepared, starting from compound 25 (180 mg, 0.43 mmol), according to the procedure developed for compound 11. Reaction time at room temperature: 14 h to give compound 26 (166 mg, 0.34 mmol) as a very hygroscopic yellow solid. Yield 78%; mp 184-186° C.; IR (KBr) ν 1178, 1351, 1466, 1516, 1676, 2200-2800, 2946, 3049, 3200-3400 cm$^{-1}$; $^1$H NMR (200 MHz, DMSO-d$_6$) δ 1.27 (t, 3H, J=7.1 Hz), 3.33 (m, 4H), 3.61 (qd, 2H, $^3J_{H\text{-}F}$=28.6 Hz, J=4.2 Hz), 3.78 (q, 2H, J=6.0 Hz), 4.69 (se, 5H), 4.92 (td, 2H, $^2J_{H\text{-}F}$=47.5 Hz, J=4.0 Hz), 7.93 (d, 1H, J=8.8 Hz), 8.26 (dd, 1H, J=1.9, 8.8 Hz), 8.64 (d, 1H, J=1.9 Hz), 9.40 (t, 1H, J=6.0 Hz), 9.46 (s, 1H), 10.89 (se, 1H); ESI-MS m/z 417.0 [M+H]$^+$; Anal. Calcd for C$_{15}$H$_{18}$OIN$_4$F, 2HCl: C, 36.83; H, 4.12; N, 11.45. Found: C, 36.59; H, 4.29; N, 11.07.

EXAMPLE 5

N-[2-[[N-ethyl-N-(2-fluoropyridin-4-yl)methyl]amino]ethyl]-6-iodoquinoxaline-2-carboxamide dihydrochloride salt (34)

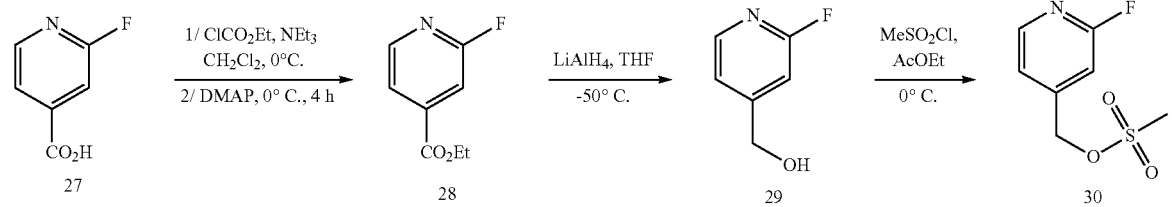

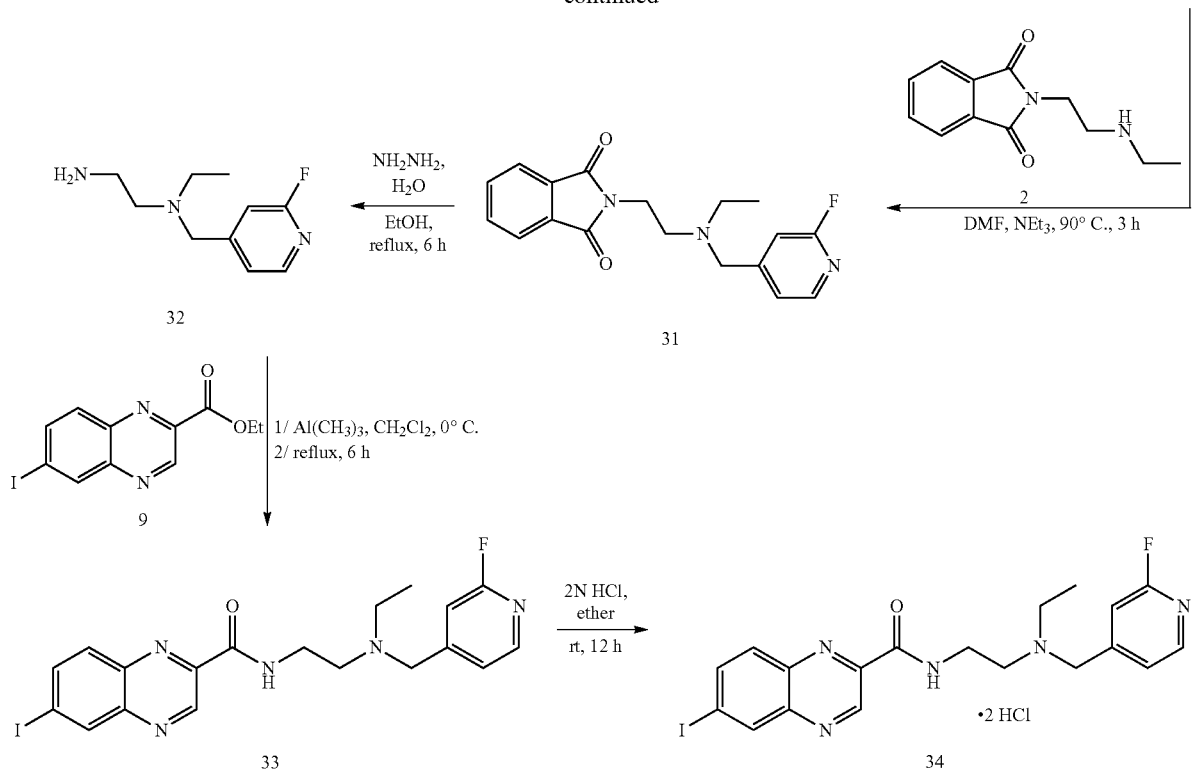

Ethyl 2-fluoroisonicotinate (28)

To a stirred solution of 2-fluoroisonicotinic acid (27) (1.00 g, 7.09 mmol) in anhydrous dichloromethane (30 mL) was added at 0° C., under argon, triethylamine (991 μL, 7.09 mmol). After 5 min, ethyl chloroformate (681 μL, 7.09 mmol) was added and the mixture was stirred at 0° C. for 5 min before addition of N-dimethyl-4-aminopyridine (DMAP, 86 mg, 0.71 mmol). The mixture was stirred at 0° C. for 4 h. After return back to room temperature, the solvent was evaporated under vacuum and the residue was chromatographed ($Al_2O_3$, $CH_2Cl_2$) to give ester 28 (0.98 g, 5.79 mmol) as a yellow liquid. Yield 82%; $R_f$ ($Al_2O_3$, $CH_2Cl_2$) 0.90; IR ($CCl_4$) ν 1096, 1210, 1299, 1409, 1572, 1735 cm$^{-1}$; $^1$H NMR (200 MHz, $CDCl_3$) δ 1.39 (t, 3H, J=7.1 Hz), 4.40 (q, 2H, J=7.1 Hz), 7.47 (ddd, 1H, $^3J_{H-F}$=2.4 Hz, J=0.8, 1.3 Hz), 7.72 (ddd, 1H, $^5J_{H-F}$=1.8 Hz, J=1.3, 5.1 Hz), 8.33 (td, 1H, $^4J_{H-F}$=0.8 Hz, J=0.8, 5.1 Hz).

2-Fluoro-4-hydroxymethylpyridine (29)

To a stirred solution of 1.0 M lithium aluminium hydride in anhydrous tetrahydrofuran (7.00 mL, 7.00 mmol) was added at −50° C., under argon, a solution of compound 28 (1.19 g, 7.00 mmol) in anhydrous tetrahydrofuran (10 mL). After 15 min, water (7 mL), a 3.0 N aqueous sodium hydroxide solution (7 mL) and water (7 mL) were added successively to the mixture until no more gas evolution was observed. After return back to room temperature, a brine solution (10 mL) was added. The mixture was extracted with dichloromethane (3×10 mL). The organic layers were combined, dried on magnesium sulfate, filtered and evaporated under reduced pressure. The residue was chromatographed ($Al_2O_3$, $CH_2Cl_2$) to give compound 29 (0.45 g, 3.50 mmol) as a beige solid. Yield 51%; $R_f$ ($Al_2O_3$, $CH_2Cl_2$) 0.32; mp 61-63° C.; IR (KBr) ν 1074, 1273, 1420, 1618, 3100-3400 cm$^{-1}$; $^1$H NMR (200 MHz, $CDCl_3$) δ 3.81 (se, 1H), 4.75 (s, 2H), 6.96 (s, 1H), 7.14 (m, 1H), 8.07 (d, 1H, J=5.1 Hz).

N-[2-[[N-ethyl-N-(2-fluoropyridin-4-yl)methyl]amino]ethyl]phthalimide (31)

To a stirred solution of compound 2 (320 mg, 1.46 mmol) in anhydrous N,N-dimethylformamide (10 mL) were added successively, under argon, triethylamine (208 μL, 1.50 mmol) and (2-fluoropyridin-4-yl)methyl methylsulfonate (30) (300 mg, 1.46 mmol) obtained from compound 29 according to the procedure developed by Pesti, J. A.; Huhn, G. F.; Yin, J.; Xing, Y.; Fortunak, J. M.; Earl, R. A. Efficient Pyridinylmethyl Functionalization: Synthesis of 10,10-Bis[(2-fluoro-4-pyridinyl)methyl]-9(10H)-anthracenone (DMP 543), an Acetylcholine Release Enhancing Agent. *J. Org. Chem.* 2000, 65, 7718-7722. The mixture was heated at 90° C. for 3 h. After cooling to room temperature, the solvent was evaporated under vacuum and the residue was chromatographed ($SiO_2$, AcOEt/cyclohexane, 6/4, v/v) to give compound 31 (309 mg, 0.94 mmol) as a beige solid. Yield 64%; $R_f$ ($SiO_2$, AcOEt/cyclohexane, 6/4, v/v) 0.78; mp 68-70° C.; IR (KBr) ν 1413, 1611, 1708 cm$^{-1}$; $^1$H NMR (200 MHz, $CDCl_3$) δ 0.94 (t, 3H, J=7.1 Hz), 2.51 (q, 2H, J=7.1 Hz), 2.68 (t, 2H, J=6.2 Hz), 3.57 (s, 2H), 3.72 (t, 2H, J=6.2 Hz), 6.70 (se, 1H), 6.95 (m, 1H), 7.68 (m, 2H), 7.76 (m, 2H), 7.85 (d, 1H, J=5.1 Hz); MS m/z 327 (M$^+$, 2), 167 (100), 110 (37), 83 (12), 77 (10), 56 (13).

N-(2-aminoethyl)-N-ethyl-N-[(2-fluoropyridin-4-l)methyl]amine (32)

This compound was prepared, starting from compound 31 (0.30 g, 0.91 mmol), according to the procedure developed for compound 22. Reaction time under reflux: 6 h; the purification was performed using column chromatography (Al$_2$O$_3$, CH$_2$Cl$_2$/EtOH, 98/2, v/v) to give compound 32 (129 mg, 0.66 mmol) as a yellow oil. Yield: 72%; R$_f$ (Al$_2$O$_3$, CH$_2$Cl$_2$/EtOH, 98/2, v/v) 0.29; IR (CCl$_4$) ν 1278, 1410, 1569, 1613, 2816, 2969, 3360 cm$^{-1}$; $^1$H NMR (400 MHz, CDCl$_3$) δ 1.04 (t, 3H, J=7.1 Hz), 2.53 (q, 2H, J=7.1 Hz), 2.56 (t, 2H, J=6.2 Hz), 2.63 (se, 2H), 2.78 (t, 2H, J=6.2 Hz), 3.61 (s, 2H), 6.96 (s, 1H), 7.16 (d, 1H, J=5.1 Hz), 8.11 (d, 1H, J=5.1 Hz); ESI-MS m/z 197.9 [M+H]$^+$.

N-[2-[[N-ethyl-N-(2-fluoropyridin-4-yl)methyl]amino]ethyl]-6-iodoquinoxaline-2-carboxamide (33)

This compound was prepared, starting from compound 32 (125 mg, 0.63 mmol), according to the procedure developed for compound 10. Reaction time under reflux: 6 h; the purification was performed using column chromatography (Al$_2$O$_3$, CH$_2$CL$_2$/EtOH, 99/1, v/v) to give compound 33 (0.12 g, 0.24 mmol) as a brown oil. Yield 38%; R$_f$ (Al$_2$O$_3$, CH$_2$Cl$_2$/EtOH, 99/1, v/v) 0.49; IR (CCl$_4$) ν 1394, 1413, 1613, 1720 cm$^{-1}$; $^1$H NMR (200 MHz, CDCl$_3$) δ 1.09 (t, 3H, J=7.1 Hz), 2.65 (q, 2H, J=7.1 Hz), 2.75 (t, 2H, J=5.8 Hz), 3.58 (q, 2H, J=5.8 Hz), 3.69 (s, 2H), 7.06 (s, 1H), 7.19 (m, 1H), 7.81 (d, 1H, J=8.9 Hz), 8.04 (m, 2H), 8.33 (se, 1H), 8.55 (d, 1H, J=1.8 Hz), 9.57 (s, 1H); MS m/z 479 (M$^+$, 3), 167 (100), 128 (9), 110 (36), 101 (10), 56 (11).

N-[2-[[N-ethyl-N-(2-fluoropyridin-4-yl)methyl]amino]ethyl]-6-iodoquinoxaline-2-carboxamide dihydrochloride salt (34)

This compound was prepared, starting from compound 33 (117 mg, 0.24 mmol), according to the procedure developed for compound 11. Reaction time at room temperature: 12 h to give compound 34 (83 mg, 0.15 mmol) as a very hygroscopic beige solid. Yield 64%; mp 139-141° C.; IR (KBr) ν 1164, 1415, 1533, 1616, 1670, 2250-2660, 2945, 3100-3600 cm$^{-1}$; $^1$H NMR (200 MHz, DMSO-d$_6$) δ 1.34 (t, 3H, J=6.9 Hz), 3.26 (m, 4H), 3.60 (m, 2H), 3.77 (m, 2H), 4.52 (m, 2H), 7.60 (s, 1H), 7.70 (m, 1H), 7.91 (d, 1H, J=8.8 Hz), 8.26 (m, 2H), 8.63 (d, 1H, J=1.8 Hz), 9.38 (m, 1H), 9.42 (s, 1H), 11.36 (se, 1H); ESI-MS m/z 480.1 [M+H]$^+$; Anal. Calcd for C$_{19}$H$_{19}$OIN$_5$F, 2HCl: C, 41.33; H, 3.83; N, 12.68. Found: C, 42.19; H, 3.59; N, 12.98.

EXAMPLE 6

N-[2-[N-ethyl-N-[2-[[(2-fluoropyridin-4-yl)carbonyl]amino]ethyl]amino]ethyl]-6-iodoquinoxaline-2-carboxamide dihydrochloride salt (40)

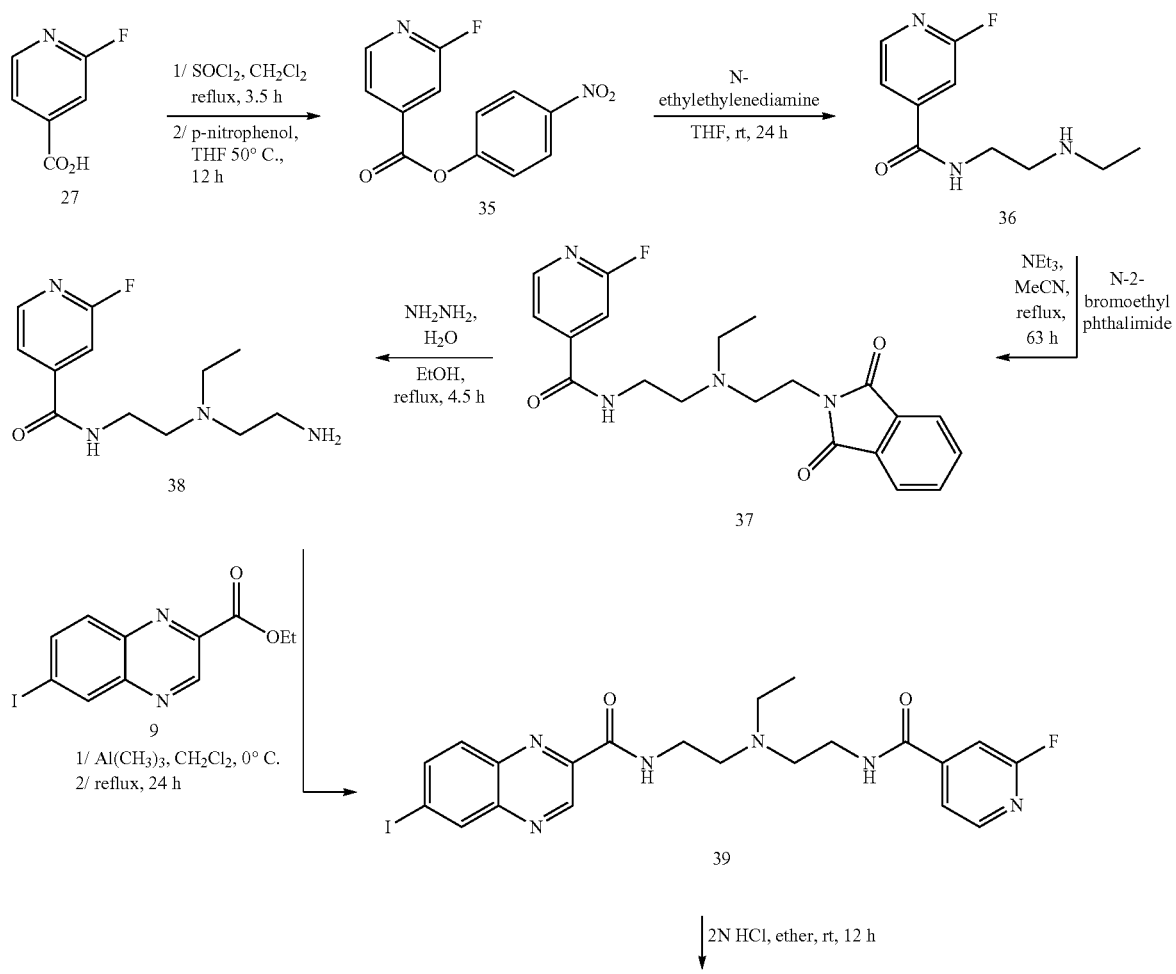

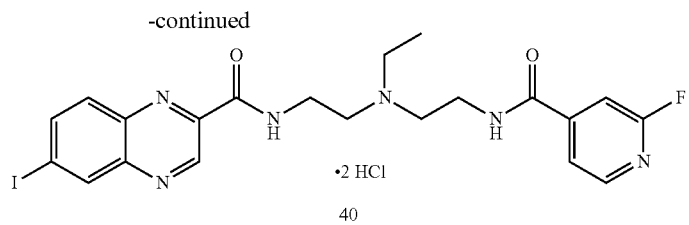

40 p-Nitrophenyl 2-fluoroisonicotinate (35)

This compound was prepared starting from compound 27 (1.00 g, 7.09 mmol), according to the procedure developed for compound 24. Reaction time at reflux: 3.5 h, reaction time at 50° C.: 12 h to give compound 35 (1.14 g, 4.35 mmol) as a white solid. Yield 61%; mp 148-150° C.; IR (KBr) ν 1220, 1283, 1406, 1525, 1742 cm$^{-1}$; $^1$H NMR (200 MHz, CDCl$_3$) δ 7.44 (d, 2H, J=9.3 Hz), 7.66 (m, 1H), 7.91 (td, 1H, $^5J_{H-F}$=1.5 Hz, J=1.5, 5.1 Hz), 8.36 (d, 2H, J=9.3 Hz), 8.50 (d, 1H, J=5.1 Hz); MS m/z 262 (M$^+$, 4), 124 (100), 96 (59), 76 (18), 69 (16), 63 (12), 51 (10).

N-[2-(N-ethylamino)ethyl]-2-fluoroisonicotinamide (36)

To a solution of compound 35 (4.60 g, 17.5 mmol) in anhydrous tetrahydrofuran (185 mL) was added, under argon, N-ethylethylenediamine (1.80 mL, 17.5 mmol). The mixture was stirred at room temperature for 24 h. The solvent was evaporated under vacuum and the residue was suspended in dichloromethane (95 mL). A 1.0 N aqueous sodium hydroxide solution (140 mL) was added to the mixture. The solution was decanted and the aqueous layer was extracted with dichloromethane (6×120 mL). The organic layers were combined, dried on magnesium sulfate, filtered and evaporated under reduced pressure. The residue was chromatographed (Al$_2$O$_3$, CH$_2$Cl$_2$/EtOH, 98/2, v/v) to give compound 36 (3.37 g, 15.9 mmol) as a yellow solid. Yield 91%; R$_f$ (Al$_2$O$_3$, CH$_2$Cl$_2$/EtOH, 98/2, v/v) 0.16; mp 51-52° C.; IR (KBr) ν 1300, 1416, 1554, 1675, 2700-3050, 3100-3600 cm$^{-1}$; $^1$H NMR (200 MHz, CDCl$_3$) δ 1.07 (t, 3H, J=7.1 Hz), 2.63 (q, 2H, J=7.1 Hz), 2.76 (se, 1H), 2.83 (t, 2H, J=5.8 Hz), 3.50 (m, 2H), 7.33 (s, 1H), 7.54 (m, 1H), 7.74 (se, 1H), 8.24 (d, 1H, J=5.1 Hz); MS m/z 212 (M+H$^+$, 1), 124 (8), 96 (15), 71 (19), 58 (100).

N-[2-[N-ethyl-N-[2-(1,3-dioxo-1,3-dihydroindol-2-yl)ethyl]amino]ethyl]-2-fluoroisonicotinamide (37)

To a stirred solution of compound 36 (100 mg, 0.47 mmol) in anhydrous acetonitrile (7 mL) were added successively, under argon, triethylamine (197 μL, 1.42 mmol) and N-(2-bromoethyl)phthalimide (361 mg, 1.42 mmol). The mixture was refluxed for 63 h. After cooling to room temperature, the solvent was evaporated under vacuum. The brown oily residue was chromatographed (SiO$_2$, CH$_2$Cl$_2$/EtOH, 98/2, v/v) to give compound 37 (99 mg, 0.26 mmol) as a yellow solid. Yield 55%; R$_f$ (SiO$_2$, CH$_2$Cl$_2$/EtOH, 98/2, v/v) 0.14; mp 74-76° C.; IR (KBr) ν 1400, 1526, 1654, 1703, 3321 cm$^{-1}$; $^1$H NMR (200 MHz, CDCl$_3$) δ 0.88 (t, 3H, J=7.1 Hz), 2.55 (q, 2H, J=7.1 Hz), 2.79 (m, 4H), 3.52 (q, 2H, J=4.8 Hz), 3.78 (m, 2H), 7.41 (m, 1H), 7.48 (se, 1H), 7.60 (td, 1H, $^5J_{h-F}$=1.4 Hz, J=5.2, 1.4 Hz), 7.66 (m, 2H), 7.72 (m, 2H), 8.29 (d, 1H, J=5.2 Hz); MS m/z 384 (M$^+$, 1), 231 (100), 224 (18), 174 (67), 167 (41), 147 (16), 124 (46), 96 (29), 58 (45).

N-(2-aminoethyl-N-ethyl-N-[2-[[(2-fluoropyridin-4-yl)carbonyl]amino]ethyl]amine (38)

This compound was prepared, starting from compound 37 (1.00 g, 2.60 mmol), according to the procedure developed for compound 22. Reaction time under reflux: 4.5 h; the purification was performed using column chromatography (Al$_2$O$_3$, CH$_2$Cl$_2$/EtOH, 93/7, v/v) to give compound 38 (0.65 g, 2.56 mmol) as a yellow oil. Yield 98%; R$_f$(Al$_2$O$_3$, CH$_2$Cl$_2$/EtOH, 93/7, v/v) 0.41; IR (CCl$_4$) ν 1304, 1397, 1567, 1673, 2750-3000 cm$^{-1}$; $^1$H NMR (200 MHz, CDCl$_3$) δ 1.08 (t, 3H, J=7.0 Hz), 2.64 (m, 4H), 2.75 (t, 2H, J=5.7 Hz), 2.86 (t, 2H, J=5.7 Hz), 2.91 (se, 2H), 3.56 (m, 2H), 7.50 (s, 1H), 7.72 (d, 1H, J=4.6 Hz), 8.34 (d, 1H, J=5.1 Hz), 8.75 (se, 1H); ESI-MS m/z 255.0 [M+H]$^+$.

N-[2-[N-ethyl-N-[2-[[(2-fluoropyridin-4-yl)carbonyl]amino]ethyl]amino]ethyl]-6-iodoquinoxaline-2-carboxamide (39)

This compound was prepared, starting from compound 38 (0.26 g, 1.02 mmol), according to the procedure developed for compound 10. Reaction time under reflux: 24 h; the purification was performed using column chromatography (Al$_2$O$_3$, CH$_2$Cl$_2$/EtOH, 98/2, v/v) to give compound 39 (236 mg, 0.45 mmol) as a beige solid. Yield 63%; R$_f$ (Al$_2$O$_3$, CH$_2$Cl$_2$/EtOH, 98/2, v/v) 0.50; mp 146-148° C.; IR (KBr) ν 1524, 1542, 1662, 2800-3000, 3335, 3388 cm$^{-1}$; $^1$H NMR (200 MHz, CDCl$_3$) δ 1.02 (t, 3H, J=7.1 Hz), 2.65 (q, 2H, J=7.1 Hz), 2.79 (m, 4H), 3.59 (m, 4H), 7.33 (s, 1H), 7.52 (d, 1H, J=5.1 Hz), 7.64 (d, 2H, J=8.8 Hz), 8.01 (dd, 1H, J=1.7, 8.8 Hz), 8.14 (d, 1H, J=5.1 Hz), 8.22 (m, 1H), 8.55 (d, 1H, J=1.7 Hz), 9.48 (s, 1H); ESI-MS m/z 537.0 [M+H]$^+$.

N-[2-[N-ethyl-N-[2-[[(2-fluoropyridin-4-yl)carbonyl]amino]ethyl]amino]ethyl]-6-iodoquinoxaline-2-carboxamide dihydrochloride salt (40)

This compound was prepared, starting from compound 39 (158 mg, 0.30 mmol), according to the procedure developed for compound 11. Reaction time at room temperature: 12 h to give compound 40 (152 mg, 0.25 mmol) as a very hygroscopic beige solid. Yield 84%; mp 157-159° C.; IR (KBr) ν 1163, 1228, 1308, 1402, 1475, 1535, 1690, 2400-2700, 2800-3100, 3200-3500 cm$^{-1}$; $^1$H NMR (200 MHz, DMSO-d$_6$) δ 1.28 (t, 3H, J=6.7 Hz), 3.37 (m, 6H, J=7.1 Hz), 3.77 (m, 4H), 7.57 (s, 1H), 7.75 (d, 1H, J=5.0 Hz), 7.86 (d, 1H, J=8.8 Hz), 8.21 (dd, 1H, J=1.7, 8.8 Hz), 8.32 (d, 1H, J=5.0 Hz), 8.59 (d, 1H, J=1.7 Hz), 9.39 (s, 1H), 9.42 (m, 2H), 10.58 (se, 1H); ESI-MS m/z 537.0 [M+H]$^+$; Anal. Calcd for C$_{21}$H$_{22}$O$_2$IN$_6$F, 2HCl: C, 41.40; H, 3.97; N, 13.79. Found: C, 42.67; H, 4.39; N, 13.66.

EXAMPLE 7

N-[2-[[N-ethyl-N-2-(2-fluoropyridin-4-yl)ethyl]amino]ethyl]-6-iodoquinoxaline-2-carboxamide dihydrochloride salt (47)

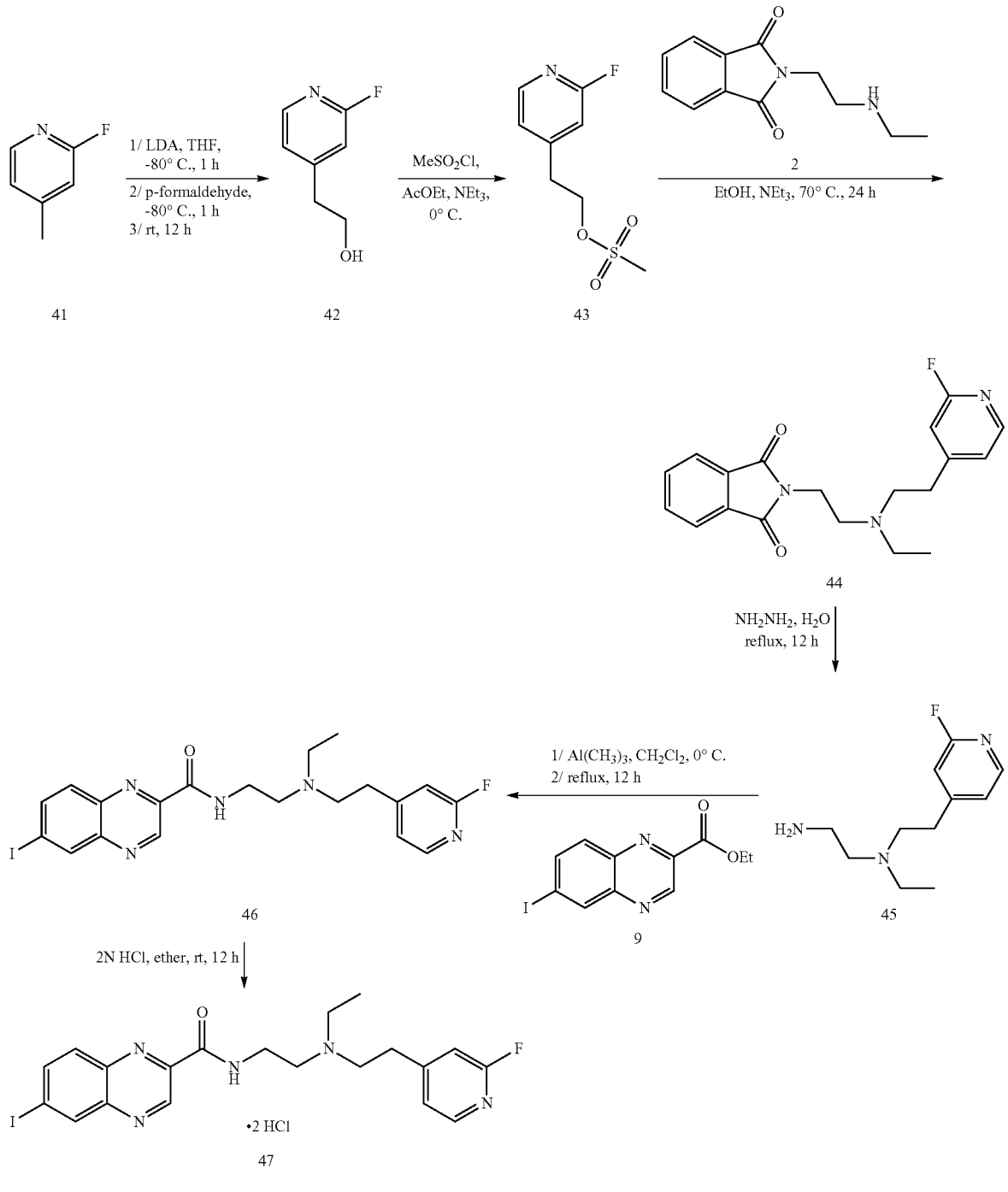

2-Fluoro-4-(2-hydroxyethyl)pyridine (42)

To a solution of anhydrous diisopropylamine (18.5 mL, 0.13 mol) in anhydrous tetrahydrofuran (160 mL) was added dropwise at −80° C., under argon, a 1.3 M n-butyllithium solution in hexane (100 mL, 0.13 mol). The mixture was stirred at −80° C. for 1 h before addition dropwise of a solution of 2-fluoro-4-picoline (41) (9.00 g, 6.30 mmol) in anhydrous tetrahydrofuran (60 mL). The mixture was stirred at −80° C. for 1 h once again before addition dropwise of a p-formaldehyde (16.6 g, 0.55 mol) suspension in anhydrous tetrahydrofuran (100 mL). The mixture was stirred at −80° C. for 1 h and then at room temperature for 12 h. A saturated aqueous ammonium chloride solution (450 mL) was added to the mixture. The solution was decanted and the aqueous layer was extracted with dichloromethane (4×200 mL). The organic layers were combined, dried on magnesium sulfate, filtered and evaporated under vacuum. The residue obtained was chromatographed (Al$_2$O$_3$, CH$_2$Cl$_2$/EtOH, 99/1, v/v) to give compound 42 (7.25 g, 51.4 mmol) as an orange-coloured oil. Yield 57%; R$_f$(Al$_2$O$_3$, CH$_2$Cl$_2$/EtOH, 99/1, v/v) 0.32; IR (CCl$_4$) ν 1046, 1149, 1278, 1413, 1613, 2800-3000, 3100-3600, 3634 cm$^{-1}$; $^1$H NMR (200 MHz, CDCl$_3$) δ 2.87 (t, 2H, J=6.3 Hz), 3.87 (t, 2H, J=6.3 Hz), 6.82 (s, 1H), 7.07 (d, 1H, J=5.2 Hz), 8.01 (d, 1H, J=5.2 Hz); MS m/z 141 (M$^+$, 23), 111 (100), 91 (34), 83 (14), 64 (10), 57 (12).

2-(2-fluoropyridin-4-yl)ethyl methylsulfonate (43)

To a solution of compound 42 (6.50 g, 46.1 mmol) in anhydrous ethyl acetate (250 mL) were added successively at 0° C., under argon, triethylamine (6.40 mL, 46.0 mmol) and dropwise methanesulfonyl chloride (3.60 mL, 46.5 mmol). The mixture was stirred at 0° C. for 10 min before addition of water (200 mL) at room temperature. The mixture was extracted with ethyl acetate (3×200 mL). The organic layers were combined, dried on magnesium sulfate, filtered and evaporated under vacuum. The residue was chromatographed (Al$_2$O$_3$, CH$_2$Cl$_2$) to give sulfonate 43 (7.56 g, 34.5 mmol) as a yellow oil. Yield 75%; R$_f$(Al$_2$O$_3$, CH$_2$Cl$_2$) 0.52; IR (CCl$_4$) ν 1179, 1352, 1414, 1613 cm$^{-1}$; $^1$H NMR (200 MHz, CDCl$_3$) δ 2.95 (s, 3H), 3.09 (t, 2H, J=6.4 Hz), 4.45 (t, 2H, J=6.4 Hz), 6.82 (s, 1H), 7.07 (d, 1H, J=5.1 Hz), 8.15 (d, 1H, J=5.1 Hz); MS m/z 219 (M$^+$, 3), 123 (100), 111 (30), 83 (14), 79 (53), 57 (11).

N-[2-[[N-ethyl-N-2-(2-fluoropyridin-4-yl)ethyl]amino]ethyl]phthalimide (44)

To a stirred solution of compound 43 (4.00 g, 18.2 mmol) in anhydrous ethanol (105 mL) were added, under argon, N-[2-(ethylamino)ethyl]phthalimide (2) (8.00 g, 36.5 mmol) and anhydrous triethylamine (5.10 mL, 36.5 mmol). The mixture was heated at 70° C. for 24 h. After cooling to room temperature, water (90 mL), a 1.0 N aqueous sodium hydroxide solution (10 mL) and a brine solution (20 mL) were added successively. The mixture was decanted and the aqueous layer was extracted with dichloromethane (3×100 mL). The organic layers were combined, dried on magnesium sulfate, filtered and evaporated under vacuum. The residue was chromatographed (SiO$_2$, AcOEt/cyclohexane, 7/3, v/v) to give in order of elution: 2-fluoro-4-vinylpyridine (0.79 g, 6.42 mmol) (Li, Q.; Li, T.; Zhu, G. D.; Gong, J.; Claibone, A.; Dalton, C.; Luo, Y.; Johnson, E. F.; Shi, Y.; Liu, X.; Klinghofer, V.; Bauch, J. L.; Marsh, K. C.; Bouska, J. J.; Arries, S.; De Jong, R.; Oltersdorf, T.; Stoll, V. S.; Jakob, C. G.; Rosenberg, S. H.; Giranda, V. L. Discovery of trans-3,4'-bispyridinylethylenes as potent and novel inhibitors of protein kinase B (PKB/Akt) for the treatment of cancer: Synthesis and biological evaluation. *Bioorg. Med. Chem. Lett.* 2006, 16, 1679-85) as an orange-coloured oil. Yield 35%; R$_f$(SiO$_2$, AcOEt/cyclohexane, 7/3, v/v) 0.80; IR (CCl$_4$) ν 1152, 1290, 1392, 1414, 1551, 1608 cm$^{-1}$; $^1$H NMR (200 MHz, CDCl$_3$) δ 5.52 (d, 1H, J=10.8 Hz), 5.95 (d, 1H, J=17.6 Hz), 6.64 (dd, 1H, J=10.8, 17.6 Hz), 6.85 (s, 1H), 7.14 (dt, 1H, $^5J_{H-F}$=1.5 Hz, J=1.5, 5.2 Hz), 8.12 (d, 1H, J=5.2 Hz); ESI-MS m/z 123.7 [M+H]$^+$; Compound 44 (0.98 g, 2.87 mmol) as a yellow oil. Yield 16%; R$_f$(SiO$_2$, AcOEt/cyclohexane, 7/3, v/v) 0.54; IR (CCl$_4$) ν 1397, 1613, 1715 cm$^{-1}$; $^1$H NMR (200 MHz, CDCl$_3$) δ 0.95 (t, 3H, J=7.1 Hz), 2.59 (q, 2H, J=7.1 Hz), 2.72 (m, 6H), 3.71 (t, 2H, J=6.6 Hz), 6.68 (s, 1H), 6.93 (dt, 1H, $^5J_{H-F}$=1.5 Hz, J=1.5, 5.2 Hz), 7.69 (m, 2H), 7.77 (m, 2H), 7.91 (d, 1H, J=5.2 Hz); ESI-MS m/z 341.9 [M+H]$^+$.

N-(2-aminoethyl)-N-ethyl-N-[2-(2-fluoropyridin-4-yl)ethyl]amine (45)

This compound was prepared, starting from compound 44 (600 mg, 1.76 mmol), according to the procedure developed for compound 22. Reaction time under reflux: 12 h; the purification was performed using column chromatography (Al$_2$O$_3$, CH$_2$Cl$_2$/EtOH/NH$_4$OH, 97/2.5/0.5, v/v/v) to give compound 45 (361 mg, 1.71 mmol) as a brown oil. Yield 97%; R$_f$(Al$_2$O$_3$, CH$_2$Cl$_2$/EtOH/NH$_4$OH, 97/2.5/0.5, v/v/v) 0.34; IR (CCl$_4$) ν 1149, 1264, 1412, 1555, 1613, 2814, 2970 cm$^{-1}$; $^1$H NMR (200 MHz, CDCl$_3$) δ 0.72 (t, 3H, J=7.1 Hz), 1.16 (se, 2H), 2.27 (m, 4H), 2.44 (m, 4H), 6.50 (s, 1H), 6.76 (m, 1H), 7.79 (d, 1H, J=5.1 Hz).

N-[2-[[N-ethyl-N-2-(2-fluoropyridin-4-yl)ethyl]amino]ethyl]-6-iodoquinoxaline-2-carboxamide (46)

This compound was prepared, starting from compound 45 (200 mg, 0.95 mmol), according to the procedure developed for compound 10. Reaction time under reflux: 12 h; the purification was performed using colomm chromatography (Al$_2$O$_3$, CH$_2$Cl$_2$/EtOH, 99/1, v/v) to give compound 46 (318 mg, 0.64 mmol) as a brown oil. Yield 68%; R$_f$ (Al$_2$O$_3$, CH$_2$Cl$_2$/EtOH, 99/1, v/v) 0.36; IR (CCl$_4$) ν 1412, 1522, 1613, 1684, 2800-3000 cm$^{-1}$; $^1$H NMR (200 MHz, CDCl$_3$) δ 1.07 (t, 3H, J=7.0 Hz), 2.67 (q, 2H, J=7.0 Hz), 2.75 (t, 2H, J=6.0 Hz), 2.82 (s, 4H), 3.53 (q, 2H, J=6.0 Hz), 6.79 (s, 1H), 7.03 (m, 1H), 7.73 (d, 1H, J=8.8 Hz), 7.98 (d, 1H, J=5.3 Hz), 8.03 (dd, 1H, J=1.8, 8.8 Hz), 8.16 (m, 1H), 8.53 (d, 1H, J=1.8 Hz), 9.59 (s, 1H); ESI-MS m/z 493.9 [M+H]$^+$.

N-[2-[[N-ethyl-N-2-(2-fluoropyridin-4-yl)ethyl]amino]ethyl]-6-iodoquinoxaline-2-carboxamide dihydrochloride salt (47)

This compound was prepared, starting from compound 46 (100 mg, 0.20 mmol), according to the procedure developed for compound 11. Reaction time at room temperature: 12 h to give compound 47 (88 mg, 0.16 mmol) as a very hygroscopic beige solid. Yield 84%; mp 208-210° C.; IR (KBr) ν 1171, 1413, 1477, 1522, 1617, 1679, 2250-2750, 3200-3600 cm$^{-1}$; $^1$H NMR (200 MHz, DMSO-d$_6$) δ 1.30 (t, 3H, J=7.1 Hz), 3.32 (m, 8H), 3.82 (q, 2H, J=6.1 Hz), 7.18 (s, 1H), 7.34 (td, 1H, $^4J_{H-F}$=1.5 Hz, J=1.5, 5.0 Hz), 7.91 (d, 1H, J=8.8 Hz), 8.17 (d, 1H, J=5.0 Hz), 8.25 (dd, 1H, J=1.8, 8.8 Hz), 8.63 (d, 1H, J=1.8 Hz), 9.45 (m, 1H), 11.04 (se, 1H); ESI-MS m/z 493.9 [M+H]$^+$.

EXAMPLE 8

N-[2-[[N-ethyl-N-3-(2-fluoropyridin-4-yl)propyl]amino]ethyl]-6-iodoquinoxaline-2-carboxamide dihydrochloride salt (53)

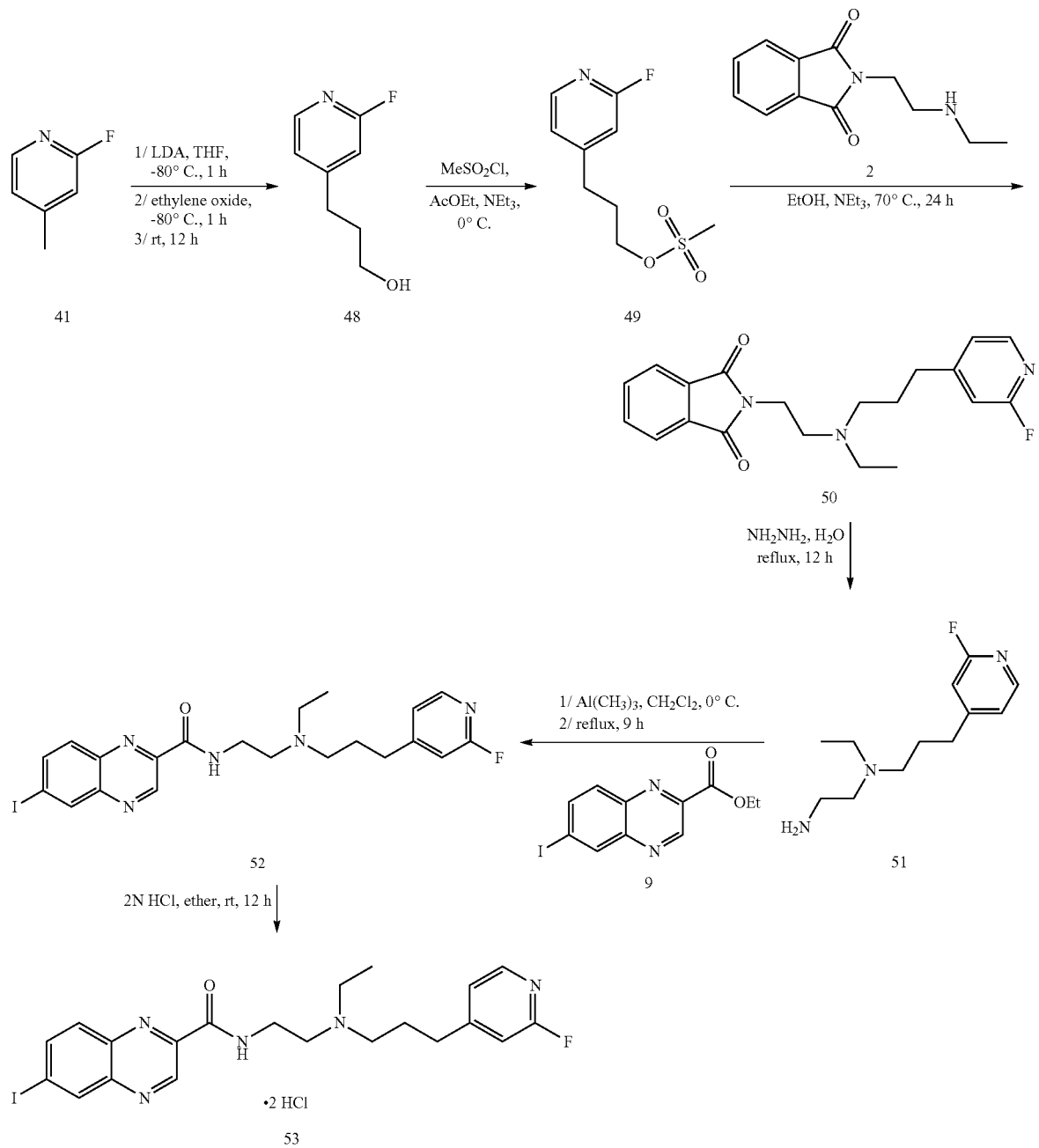

2-fluoro-4-(3-hydroxypropyl)pyridine (48)

This compound was prepared, starting from compound 41 (7.00 g, 6.30 mmol) and ethylene oxide (4.20 mL, 84.1 mmol), according to the procedure developed for compound 42. The purification was performed using colomm chromatography (SiO$_2$, AcOEt/pentane, 6/4, v/v) to give alcohol 48 (5.16 g, 33.3 mmol) as a yellow oil. Yield 53%; R$_f$ (SiO$_2$, AcOEt/pentane 6/4, v/v) 0.52; IR (CCl$_4$) ν 1412, 1613, 2939, 3639 cm$^{-1}$; $^1$H NMR (200 MHz, CDCl$_3$) δ 1.84 (m, 2H), 2.72 (t, 2H, J=7.4 Hz), 3.14 (se, 1H), 3.62 (t, 2H, J=6.2 Hz), 6.72 (s, 1H), 6.98 (m, 1H), 8.01 (d, 1H, J=5.1 Hz); MS m/z 155 (M$^+$, 6), 137 (25), 124 (12), 111 (100), 91 (21), 77 (14), 57 (14), 51 (16).

3-(2-fluoropyridin-4-yl)propyl methylsulfonate (49)

This compound was prepared, starting from compound 48 (5.00 g, 32.2 mmol), according to the procedure developed for compound 43. Reaction time at 0° C.: 30 min; the purification was performed using column chromatography (SiO$_2$, AcOEt/pentane, 8/2, v/v) to give compound 49 (4.82 g, 20.7 mmol) as a yellow oil. Yield 69%; R$_f$ (SiO$_2$, AcOEt/pentane, 8/2, v/v) 0.58; IR (CCl$_4$) ν 1179, 1351, 1371, 1413, 1613 cm$^{-1}$; $^1$H NMR (200 MHz, CDCl$_3$) δ 2.12 (m, 2H), 2.83 (t, 2H, J=7.3 Hz), 3.05 (s, 3H), 4.28 (t, 2H, J=6.1 Hz), 6.80 (s, 1H), 7.07 (m, 1H), 8.15 (d, 1H, J=5.1 Hz).

N-[2-[[N-ethyl-N-3-(2-fluoropyridin-4-yl)propyl]amino]ethyl]phthalimide

To a stirred solution of compound 49 (7.00 g, 30.0 mmol) in anhydrous ethanol (210 mL) were added, under argon, compound 2 (19.65 g, 90.1 mmol) and anhydrous triethylamine (12.5 mL, 89.9 mmol). The mixture was heated at 70° C., under argon, for 24 h. After cooling to room temperature, water (150 mL) and a 1.0 N aqueous sodium hydroxide solution (60 mL) were added. The mixture was decanted and the aqueous layer was extracted with dichloromethane (3×50 mL). The organic layers were combined, dried on magnesium sulfate, filtered and evaporated under vacuum. The residue was chromatographed (SiO$_2$, AcOEt/cyclohexane, 7/3, v/v) to give compound 50 (3.70 g, 10.4 mmol) as a yellow oil. Yield 35%; RJ (SiO$_2$, AcOEt/cyclohexane, 7/3, v/v) 0.38; IR (CCl$_4$) ν 1396, 1411, 1613, 1716, 1774, 2809, 2948, 2970 cm$^{-1}$; $^1$H NMR (200 MHz, CDCl$_3$) δ 0.97 (t, 3H, J=7.1 Hz), 1.69 (m, 2H), 2.54 (m, 6H), 2.72 (t, 2H, J=6.6 Hz), 3.77 (t, 2H, J=6.6 Hz), 6.61 (m, 1H), 6.90 (m, 1H), 7.71 (m, 2H), 7.81 (m, 2H), 8.04 (d, 1H, J=5.2 Hz); ESI-MS m/z 356.0 [M+H]$^-$.

N-(2-aminoethyl)-N-ethyl-N-[3-(2-fluoropyridin-4-yl)propyl]amine (51)

This compound was prepared, starting from compound 50 (1.00 g, 2.81 mmol), according to the procedure developed for compound 22. Reaction time under reflux: 12 h; the purification was performed using column chromatography (Al$_2$O$_3$, CH$_2$Cl$_2$/EtOH, 97/3, v/v) to give compound 51 (0.55 g, 2.42 mmol) as a brown oil. Yield 86%; R$_f$ (Al$_2$O$_3$, CH$_2$Cl$_2$/EtOH, 97/3, v/v) 0.27; IR (CCl$_4$) ν 1412, 1613, 2336, 2810, 2850-3000 cm$^{-1}$; $^1$H NMR (200 MHz, CDCl$_3$) δ 0.90 (t, 3H, J=7.1 Hz), 1.31 (se, 2H), 1.70 (m, 2H), 2.39 (m, 6H), 2.60 (m, 4H), 6.66 (s, 1H), 6.92 (m, 1H), 7.99 (d, 1H, J=5.1 Hz); ESI-MS m/z 225.9 [M+H]$^+$.

N-[2-[[N-ethyl-N-3-(2-fluoropyridin-4-yl)propyl]amino]ethyl]-6-iodoquinoxaline-2-carboxamide (52)

This compound was prepared, starting from compound 51 (200 mg, 0.89 mmol), according to the procedure developed for compound 10. Reaction time under reflux: 9 h; the purification was performed using column chromatography (Al$_2$O$_3$, CH$_2$Cl$_2$/EtOH, 99/1, v/v) to give compound 52 (345 mg, 0.68 mmol) as a brown solid. Yield 76%; R$_f$ (Al$_2$O$_3$, CH$_2$Cl$_2$/EtOH, 99/1, v/v) 0.43; mp 70-72° C.; IR (KBr) ν 1148, 1273, 1405, 1518, 1612, 1659, 1685, 2808, 2966, 3397 cm$^{-1}$; $^1$H NMR (200 MHz, CDCl$_3$) δ 1.07 (t, 3H, J=7.0 Hz), 1.83 (m, 2H), 2.56 (t, 2H, J=7.0 Hz), 2.64 (q, 2H, J=7.0 Hz), 2.73 (m, 4H), 3.58 (q, 2H, J=5.9 Hz), 6.73 (s, 1H), 6.97 (m, 1H), 7.65 (d, 1H, J=8.8 Hz), 7.99 (dd, 1H, J=1.9, 8.8 Hz), 8.01 (d, 1H, J=5.1 Hz), 8.38 (m, 1H), 8.54 (d, 1H, J=1.9 Hz), 9.62 (s, 1H); ESI-MS m/z 508.0 [M+H]$^+$.

N-[2-[[N-ethyl-N-3-(2-fluoropyridin-4-yl)propyl]amino]ethyl]-6-iodoquinoxaline-2-carboxamide dihydrochloride salt (53)

This compound was prepared, starting from compound 52 (100 mg, 0.20 mmol), according to the procedure developed for compound 11. Reaction time at room temperature: 12 h to give compound 53 (97 mg, 0.17 mmol) as a very hygroscopic yellow solid. Yield 84%; mp 89-91° C. (dec.); IR (KBr) ν 1163, 1413, 1474, 1529, 1614, 1669, 2250-2800, 2944, 3100-3600 cm$^{-1}$; $^1$H NMR (200 MHz, DMSO-d$_6$) δ 1.25 (t, 3H, J=7.1 Hz), 2.05 (m, 2H), 2.74 (t, 2H, J=7.7 Hz), 3.21 (m, 6H), 3.76 (q, 2H, J=5.9 Hz), 7.06 (s, 1H), 7.23 (td, 1H, $^5J_{H-F}$=1.8 Hz, J=1.8, 5.1 Hz), 7.91 (d, 1H, J=8.8 Hz), 8.11 (d, 1H, J=5.1 Hz), 8.26 (dd, 1H, J=1.8, 8.8 Hz), 8.64 (d, 1H, J=1.8 Hz), 9.39 (t, 1H, J=5.9 Hz), 9.45 (s, 1H), 10.56 (se, 1H); ESI-MS m/z 508.0 [M+H]$^+$; Anal. Calcd for C$_{21}$H$_{23}$OIN$_5$F, 2HCl: C, 42.16; H, 4.55; N, 11.71. Found: C, 42.45; H, 4.49; N, 11.88.

EXAMPLE 9

N-[2-[N-ethyl-N-((E)-4-fluorobut-2-enyl)]amino]ethyl]-6-iodoquinoxaline-2-carboxamide dihydrochloride salt (57)

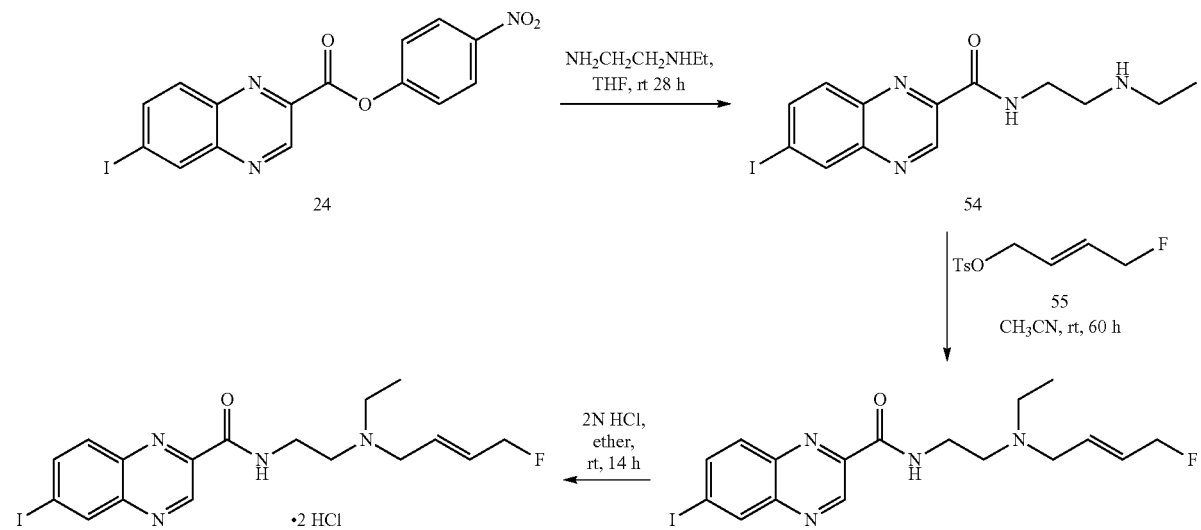

N-[2-[(N-ethyl)amino]ethyl]-6-iodoquinoxaline-2-carboxamide (54)

This compound was prepared, starting from compound 24 (0.35 g, 0.83 mmol), according to the procedure developed for compound 36. Reaction time at room temperature: 28 h; the purification was performed using column chromatography (Al$_2$O$_3$, CH$_2$Cl$_2$/EtOH, 98/2, v/v) to give compound 54 (0.27 g, 0.76 mmol) as a beige solid. Yield 92%; R$_f$ (Al$_2$O$_3$, CH$_2$Cl$_2$/EtOH, 98/2, v/v) 0.28; $^1$H NMR (200 MHz, CDCl$_3$) δ 1.18 (t, 3H, J=7.1 Hz), 1.57 (se, 1H), 2.76 (q, 2H, J=7.1 Hz), 2.97 (t, 2H, J=6.1 Hz), 3.68 (q, 2H, J=6.0 Hz), 7.83 (d, 1H, J=8.8 Hz), 8.08 (dd, 1H, J=1.9, 8.8 Hz), 8.34 (m, 1H), 8.60 (d, 1H, J=1.9 Hz), 9.65 (s, 1H).

(E)-4-Fluoro-but-2-enyl toluene-4-sulfonate (55)

This compound was prepared, starting from (E)-but-2-enediol ditosylate (0.50 g, 1.26 mmol), according to the procedure described by Dollé, F.; Emond, P.; Mavel, S.; Demphel, S.; Hinnen, F.; Mincheva, Z.; Saba, W.; Valette, H.; Chalon, S.; Halldin, C.; Helfenbein, J.; Legaillard, J.; Madelmont, J. C.; Deloye, J. B.; Bottlaender, M.; Guilloteau, D. Synthesis, radiosynthesis and in vivo preliminary evaluation of [$^{11}$C] LBT-999, a selective radioligand for the visualisation of the dopamine transporter with PET *Bioorg. Med. Chem.* 2006, 14, 1115-1125. Reaction time under reflux: 1 h; the purification was performed using column chromatography (SiO$_2$, CH$_2$Cl$_2$/pentane, 8/2, v/v) to give compound 55 (87 mg, 0.36 mmol) as a colourless oil. Yield 28%; R$_f$ (SiO$_2$, CH$_2$Cl$_2$/pentane, 8/2, v/v) 0.42; IR (CCl$_4$) ν 1179, 1190, 1375, 1599 cm$^{-1}$; $^1$H NMR (200 MHz, CDCl$_3$) δ 2.45 (s, 3H), 4.57 (m, 2H), 4.82 (dd, 2H, $^2$J$_{H-F}$=46.7 Hz, J=4.7 Hz), 5.85 (m, 2H), 7.36 (d, 2H, J=8.2 Hz), 7.79 (d, 2H, J=8.2 Hz).

N-[2-[N-ethyl-N-((E)-4-fluorobut-2-enyl)]amino]ethyl]-6-iodoquinoxaline-2-carboxamide (56)

To a solution of compound 55 (380 mg, 1.56 mmol) in acetonitrile (16 mL) was added, dropwise, a solution of compound 54 (464 mg, 1.13 mmol) in acetonitrile (17 mL). The mixture was stirred at room temperature for 60 h. The solvent was then evaporated under vacuum and the residue was chromatographed (Al$_2$O$_3$, CH$_2$Cl$_2$/EtOH, 99/1, v/v) to give compound 56 (235 mg, 0.53 mmol) as a yellow solid. Yield 47%; R$_f$ (Al$_2$O$_3$, CH$_2$Cl$_2$/EtOH, 99/1, v/v) 0.36; mp 50-52° C. (dec.); IR (CCl$_4$) ν 1160, 1353, 1475, 1520, 1682, 2817, 2850-3000, 3409 cm$^{-1}$; $^1$H NMR (200 MHz, CDCl$_3$) δ 1.08 (t, 3H, J=7.1 Hz), 2.63 (q, 2H, J=7.1 Hz), 2.72 (t, 2H, J=6.2 Hz), 3.21 (m, 2H), 3.57 (q, 2H, J=5.9 Hz), 4.81 (dd, 2H, $^2$J$_{H-F}$=47.0 Hz, J=4.3 Hz), 5.90 (m, 2H), 7.81 (d, 1H, J=8.8 Hz), 8.07 (dd, 1H, J=1.8, 8.8 Hz), 8.32 (m, 1H), 8.59 (d, 1H, J=1.8 Hz), 9.63 (s, 1H); ESI-MS m/z 442.9 [M+H]$^+$.

N-[2-[N-ethyl-N-((E)-4-fluorobut-2-enyl)]amino]ethyl]-6-iodoquinoxaline-2-carboxamide dihydrochloride salt (57)

This compound was prepared, starting from compound 56 (200 mg, 0.45 mmol), according to the procedure developed for compound 11. Reaction time at room temperature: 14 h to give compound 57 (206 mg, 0.40 mmol) as a very hygroscopic beige solid. Yield 89%; mp 139-141° C. (dec.); IR (KBr) ν 1166, 1522, 1676, 2300-2600, 3200-3500 cm$^{-1}$; $^1$H NMR (200 MHz, DMSO-d$_6$) δ 1.27 (t, 3H, J=7.1 Hz), 3.24 (m, 4H), 3.75 (q, 2H, J=5.9 Hz), 3.88 (m, 2H), 4.94 (m, 1H), 4.95 (dd, 2H, $^2$J$_{H-F}$=46.6 Hz, J=4.6 Hz), 5.96 (m, 1H), 6.23 (tt, 1H, $^4$J$_{H-F}$=15.8 Hz, J=4.6, 15.8 Hz), 7.93 (d, 1H, J=8.8 Hz), 8.26 (dd, 1H, J=1.5, 8.8 Hz), 8.64 (d, 1H, J=1.5 Hz), 9.39 (t, 1H, J=5.6 Hz), 9.46 (s, 1H), 10.66 (se, 1H); ESI-MS m/z 442.9 [M+H]f.

EXAMPLE 10

N-[2-[N-ethyl-N-[2-(2-nitropyridin-3-yloxy)ethyl]amino]ethyl]-6-iodoquinoxaline-2-carboxamide (60)

Compound of formula (60) as follows is a precursor of the corresponding compound 10 comprising F instead of the NO$_2$ group.

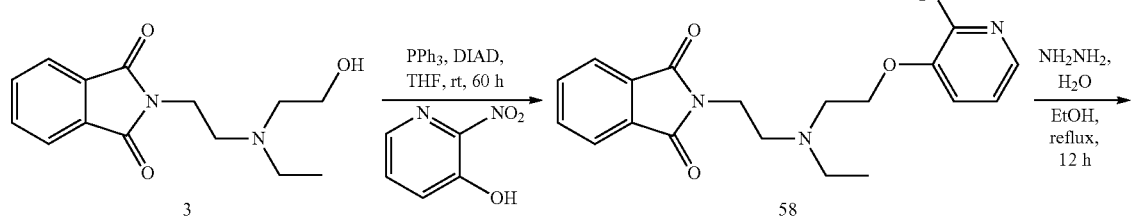

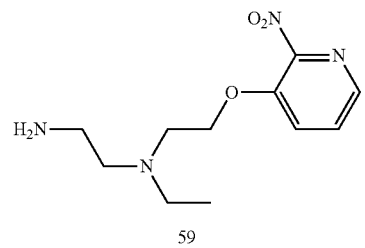

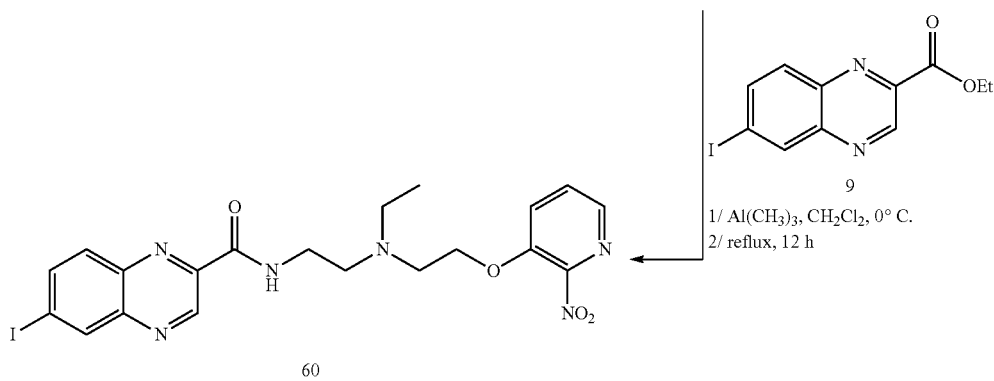

N-[2-[N-ethyl-N-[2-(2-nitropyridin-3-yloxy)ethyl]amino]ethyl]phthalimide (58)

To a solution of compound 3 (11.3 g, 43.1 mmol) in anhydrous tetrahydrofuran (400 mL) were added successively, under argon, triphenylphosphine (11.3 g, 43.1 mmol), 2-nitro-3-hydroxypyridine (6.02 g, 43.0 mmol) and dropwise diisopropyl azodicarboxylate (8.70 mL, 44.2 mmol). The mixture was stirred at room temperature for 60 h and the solvent was evaporated under vacuum. Unreacted 2-nitro-3-hydroxypyridine was removed by chromatography ($Al_2O_3$., AcOEt/cyclohexane, 9/1, v/v). The residue containing the desired product was dissolved in dichloromethane (200 mL) and pentane (600 mL) was added. The mixture was stirred at room temperature for 5 min and the precipitate was filtered and dried under vacuum to give compound 58 (12.7 g, 33.0 mmol) as a yellow solid. Yield 77%; $R_f$ ($Al_2O_3$, AcOEt/cyclohexane, 9/1, v/v) 0.76; mp 124-126° C.; IR (KBr) ν 1274, 1397, 1536, 1702, 1767, 2830 cm$^{-1}$; $^1$H NMR (200 MHz, CDCl$_3$) δ 0.96 (t, 3H, J=7.1 Hz), 2.63 (q, 2H, J=7.1 Hz), 2.81 (t, 2H, J=6.4 Hz), 2.94 (t, 2H, J=5.8 Hz), 3.76 (t, 2H, J=6.4 Hz), 4.10 (t, 2H, J=5.8 Hz), 7.50 (m, 2H), 7.60 (m, 2H), 7.75 (m, 2H), 8.05 (dd, 1H, J=2.5, 3.4 Hz); ESI-MS m/z 385.0 [M+H]$^+$.

N-(2-aminoethyl)-N-ethyl-N-[2-(2-nitropyridin-3-yloxy)ethyl]amine (59)

This compound was prepared, starting from compound 58 (2.00 g, 5.20 mmol), according to the procedure developed for compound 22. Reaction time under reflux: 12 h; the purification was performed using column chromatography ($Al_2O_3$, CH$_2$Cl$_2$/EtOH, 95/5, v/v) to give compound 59 (1.01 g, 3.97 mmol) as a yellow oil. Yield 77%; $R_f$ ($Al_2O_3$, CH$_2$Cl$_2$/EtOH, 95/5, v/v) 0.36; $^1$H NMR (200 MHz, CDCl$_3$) δ 1.11 (t, 3H, J=7.1 Hz), 2.72 (m, 8H), 2.99 (t, 2H, J=5.6 Hz), 4.28 (t, 2H, J=5.6 Hz), 7.63 (dd, 1H, J=4.3, 8.4 Hz), 7.71 (dd, 1H, J=1.5, 8.4 Hz), 8.13 (dd, 1H, J=1.5, 4.3 Hz); ESI-MS m/z 255.0 [M+H]$^+$.

N-[2-[N-ethyl-N-[2-(2-nitropyridin-3-yloxy)ethyl]amino]ethyl]-6-iodoquinoxaline-2-carboxamide (60)

This compound was prepared, starting from compound 59 (600 mg, 2.36 mmol), according to the procedure developed for compound 10. Reaction time under reflux: 12 h; the purification was performed using column chromatography ($Al_2O_3$, CH$_2$C$_2$/EtOH, 99/1, v/v) to give compound 60 (902 mg, 1.68 mmol) as a light sensitive brown oil. Yield 71%; $R_f$ ($Al_2O_3$, CH$_2$Cl$_2$/EtOH, 99/1, v/v) 0.46; IR (CCl$_4$) ν 1117, 1289, 1526, 1549, 1683, 2800-3000, 3410 cm$^{-1}$; $^1$H NMR (200 MHz, CDCl$_3$) δ 1.08 (t, 3H, J=7.1 Hz), 2.70 (q, 2H, J=7.1 Hz), 2.83 (t, 2H, J=6.1 Hz), 2.99 (t, 2H, J=5.3 Hz), 3.57 (q, 2H, J=6.1 Hz), 4.17 (t, 2H, J=5.3 Hz), 7.36 (dd, 1H, J=4.2, 8.4 Hz), 7.43 (dd, 1H, J=1.7, 8.4 Hz), 7.61 (d, 1H, J=8.8 Hz), 7.94 (dd, 1H, J=1.7, 4.2 Hz), 7.99 (dd, 1H, J=1.8, 8.8 Hz), 8.29 (m, 1H), 8.53 (d, 1H, J=1.8 Hz), 9.57 (s, 1H); ESI-MS m/z 536.9 [M+H]$^+$.

EXAMPLE 11

N-[2-[N-[2-[(6-bromopyridin-2-yl)amino]ethyl]-N-(ethyl)amino]ethyl]-6-iodoquinoxaline-2-carboxamide (63)

Compound of formula 63 as follows is a precursor of the corresponding compound 16 comprising F instead of the Br atom.

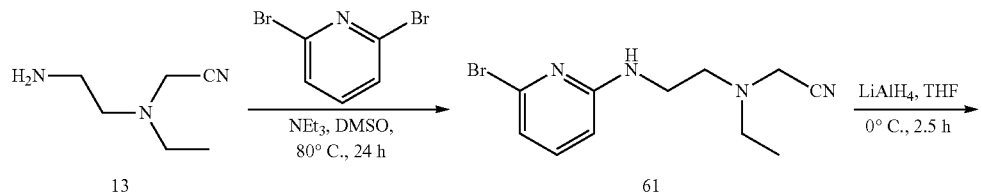

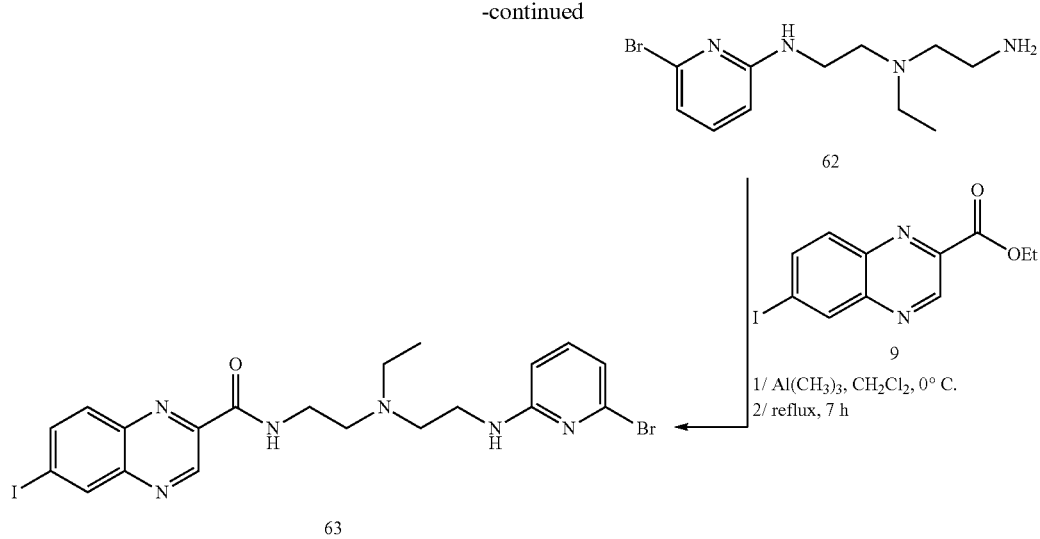

N-[2-[(6-bromopyridin-2-yl)amino]ethyl]-N-ethylaminoacetonitrile (61)

This compound was prepared, starting from compound 13 (0.80 g, 6.29 mmol), according to the procedure developed for compound 14. Reaction time at 80° C.: 24 h; the purification was performed using column chromatography (SiO$_2$, AcOEt/cyclohexane, 8/2, v/v) to give compound 61 (431 mg, 1.52 mmol) as a yellow oil. Yield 24%; R$_f$ (SiO$_2$, AcOEt/cyclohexane, 8/2, v/v) 0.68; IR (CCl$_4$) ν 1159, 1436, 1490, 1557, 1594, 2750-3000 cm$^{-1}$; $^1$H NMR (200 MHz, CDCl$_3$) δ 1.10 (t, 3H, J=7.1 Hz), 2.63 (q, 2H, J=7.1 Hz), 2.78 (t, 2H, J=6.2 Hz), 3.33 (q, 2H, J=6.2 Hz), 3.60 (s, 2H), 5.06 (m, 1H), 6.29 (d, 1H, J=8.3 Hz), 6.72 (d, 1H, J=7.5 Hz), 7.24 (t, 1H, J=7.9 Hz); ESI-MS m/z 282.9 [M+H]$^+$.

N-(2-aminoethyl)-N-[2-[N-(6-bromopyridin-2-yl)amino]ethyl]-N-ethylamine (62)

To a stirred 1.0 M solution of lithium aluminium hydride in anhydrous tetrahydrofuran (1.22 mL, 1.22 mol) diluted in anhydrous tetrahydrofuran (3 mL), was added at −15° C., under argon, a solution of compound 61 (0.23 g, 0.81 mmol) in anhydrous tetrahydrofuran (5 mL). The mixture was stirred at −15° C. for 2.5 h. Water (100 μL), a 3.0 N aqueous sodium hydroxide solution (100 μL) and water (100 μL) were added successively until no more gas evolution was observed. The mixture was filtered and the filtrate was dried on magnesium sulfate, filtered and evaporated under vacuum. The residue was chromatographed (Al$_2$O$_3$, CH$_2$Cl$_2$/EtOH/NH$_4$OH, 90/9/1, v/v/v) to give compound 62 (120 mg, 0.42 mmol) as a yellow oil. Yield 52%; R$_f$ (Al$_2$O$_3$, CH$_2$Cl$_2$/EtOH/NH$_4$OH, 90/9/1, v/v/v) 0.31: $^1$H NMR (200 MHz, CDCl$_3$) 0.99 (t, 3H, J=7.1 Hz), 1.80 (se, 2H), 2.61 (m, 8H), 3.26 (q, 2H, J=5.6 Hz), 5.37 (se, 1H), 6.27 (d, 1H, J=8.2 Hz), 6.66 (d, 1H, J=7.4 Hz), 7.19 (t, 1H, J=7.8 Hz).

N-[2-[N-[2-[(6-bromopyridin-2-yl)amino]ethyl]-N-(ethyl)amino]ethyl]-6-iodoquinoxaline-2-carboxamide (63)

This compound was prepared, starting from compound 62 (120 mg, 0.42 mmol), according to the procedure developed for compound 10. Reaction time under reflux: 7 h; the purification was performed using column chromatography (Al$_2$O$_3$, CH$_2$Cl$_2$/EtOH, 99/1, v/v) to give compound 63 (166 mg, 0.33 mmol) as a yellow solid. Yield 70%; R$_f$ (Al$_2$O$_3$, CH$_2$Cl$_2$/EtOH, 99/1, v/v) 0.34; mp 49-51° C.; IR (KBr) ν 1160, 1594, 1671, 2750-3000, 3200-3400 cm$^{-1}$; $^1$H NMR (400 MHz, CDCl$_3$) δ 1.04 (t, 3H, J=7.1 Hz), 2.64 (q, 2H, J=7.1 Hz), 2.74 (m, 4H), 3.27 (q, 2H, J=5.3 Hz), 3.57 (q, 2H, J=5.8 Hz), 5.32 (m, 1H), 6.16 (d, 1H, J=8.1 Hz), 6.56 (d, 1H, J=7.4 Hz), 7.05 (t, 1H, J=7.8 Hz), 7.81 (d, 1H, J=8.8 Hz), 8.05 (dd, 1H, J=1.9, 8.8 Hz), 8.25 (m, 1H), 8.55 (d, 1H, J=1.9 Hz), 9.58 (s, 1H); ESI-MS m/z 568.9 [M+H]$^+$.

EXAMPLE 12 tert-butyl N-[2-[N-ethyl-N-[2-(2-fluoropyridin-3-yloxy)ethyl]amino]ethyl]carbamate (64)

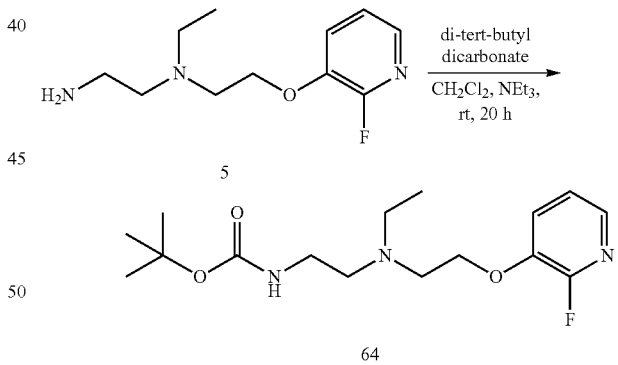

Tert-butyl N-[2-[N-ethyl-N-[2-(2-fluoropyridin-3-yloxy)ethyl]amino]ethyl]carbamate (64)

To a solution of compound 5 (500 mg, 2.20 mmol) in anhydrous dichloromethane (15 mL) were successively added triethylamine (306 μL, 2.20 mmol) and di-tert-butyl dicarbonate (480 mg, 2.20 mmol). The mixture was stirred at room temperature for 20 h. A 1 N aqueous hydrochloric acid solution (10 mL) was added. The mixture was decanted and the organic layer was washed successively with a saturated aqueous sodium hydrogenocarbonate solution (2×5 mL) and water (2×5 mL). The organic layer was then dried on magnesium sulfate, filtered and evaporated under reduce pressure to give compound 64 (506 mg, 1.55 mmol) as an orange oil. Yield 70%; IR (CCl$_4$) ν 1172, 1250, 1453, 1466, 1498, 1580, 1716, 2978 cm$^{-1}$; $^1$H NMR (200 MHz, CDCl$_3$) δ 1.01 (t, 3H, J=7.1 Hz), 1.38 (s, 9H), 2.61 (m, 4H), 2.88 (t, 2H, J=5.7 Hz), 3.16 (q, 2H, J=5.9 Hz), 4.04 (t, 2H, J=5.7 Hz), 5.05 (m, 1H, NH), 7.07 (ddd, 1H, $^5J_{H-F}$=0.8 Hz, J=4.8, 7.8 Hz), 7.27 (m, 1H), 7.70 (td, 1H, $^4J_{H-F}$=1.6 Hz, J=1.6, 4.8 Hz); MS m/z 327 (M$^+$, 1), 254 (5), 197 (100), 85 (13), 72 (7), 57 (29).

EXAMPLE 13 tert-butyl N-[2-[N-ethyl-N-[2-(2-nitropyridin-3-yloxy)ethyl]amino]ethyl]carbamate (65)

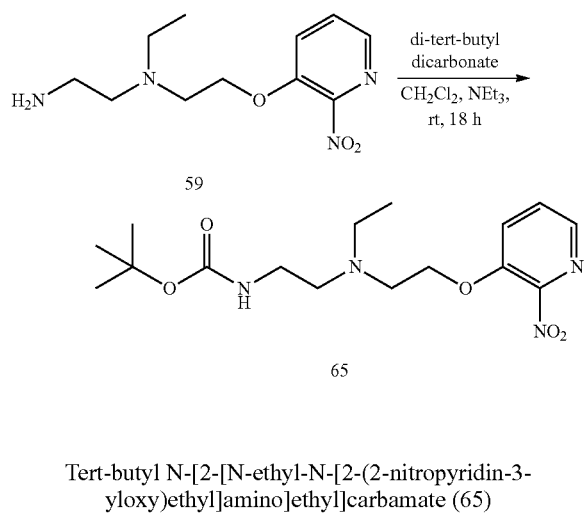

Tert-butyl N-[2-[N-ethyl-N-[2-(2-nitropyridin-3-yloxy)ethyl]amino]ethyl]carbamate (65)

This compound was prepared, starting from compound 59 (500 mg, 1.97 mmol), according to the procedure developed for compound 64. Reaction time at room temperature: 18 h to give compound 65 (444 mg, 1.25 mmol) as a yellow oil. Yield 64%; IR (CCl$_4$) ν 1172, 1289, 1367, 1500, 1549, 1716, 2977 cm$^{-1}$; $^1$H NMR (200 MHz, CDCl$_3$) δ 1.00 (t, 3H, J=7.1 Hz), 1.36 (s, 9H), 2.60 (m, 4H), 2.89 (t, 2H, J=5.6 Hz), 3.13 (q, 2H, J=5.9 Hz), 4.13 (t, 2H, J=5.6 Hz), 7.51 (m, 2H), 8.05 (dd, 1H, J=2.4, 3.4 Hz); ESI-MS m/z 355.1 [M+H]$^+$.

EXAMPLE 14

N-[2-[N-ethyl-N-[2-(2-fluoropyridin-3-yloxy)ethyl]amino]ethyl]-6-iodoquinoline-2-carboxamide dihydrochloride salt (68)

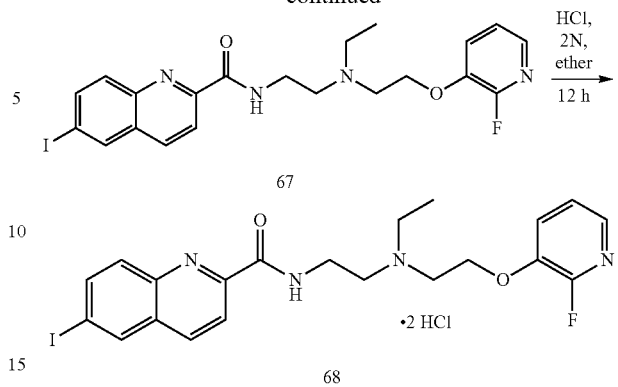

N-[2-[N-ethyl-N-[2-(2-fluoropyridin-3-yloxy)ethyl]amino]ethyl]-6-iodoquinoline-2-carboxamide (67)

This compound was prepared, starting from compound 5 (200 mg, 0.88 mmol) and ethyl 6-iodoquinoline-2-carboxylate (66) (203 mg, 0.62 mmol), according to the procedure developed for compound 10. Reaction time under reflux: 12 h; the purification was performed using column chromatography (Al$_2$O$_3$, CH$_2$Cl$_2$/EtOH, 98/2, v/v) to give compound 67 (302 mg, 0.59 mmol) as a brown oil. Yield 96%; R$_f$ (Al$_2$O$_3$, CH$_2$Cl$_2$/EtOH, 98/2, v/v) 0.68; IR (CCl$_4$) ν 1190, 1466, 1522, 1683, 2960 cm$^{-1}$; $^1$H NMR (200 MHz, CDCl$_3$) δ 1.13 (t, 3H, J=7.1 Hz), 2.76 (q, 2H, J=7.1 Hz), 2.87 (t, 2H, J=6.0 Hz), 3.02 (t, 2H, J=5.8 Hz), 3.62 (q, 2H, J=6.0 Hz), 4.14 (t, 2H, J=5.8 Hz), 6.95 (ddd, 1H, $^5J_{H-F}$=0.7 Hz, J=4.8, 7.8 Hz), 7.21 (ddd, 1H, $^4J_{H-F}$=10.0 Hz, J=1.5, 7.8 Hz), 7.65 (m, 1H), 7.66 (d, 1H, J=8.9 Hz), 7.94 (dd, 1H, J=1.9, 8.9 Hz), 8.16 (d, 1H, J=8.6 Hz), 8.26 (s, 1H), 8.29 (d, 1H, J=8.6 Hz), 8.57 (m, 1H): ESI-MS m/z 508.9 [M+H]$^+$.

N-[2-[N-ethyl-N-[2-(2-fluoropyridin-3-yloxy)ethyl]amino]ethyl]-6-iodoquinoline-2-carboxamide dihydrochloride salt (68)

This compound was prepared, starting from compound 67 (0.20 g, 0.39 mmol), according to the procedure developed for compound 11. Reaction time at room temperature: 12 h to give compound 68 (184 mg, 0.32 mmol) as a very hygroscopic beige solid. Yield 81%; mp 99-101° C. (dec.); IR (KBr) ν 1255, 1385, 1465, 1559, 1645, 2500-3500 cm$^{-1}$.

EXAMPLE 15

N-[2-[N-ethyl-N-[2-(2-fluoropyridin-3-yloxy)ethyl]amino]ethyl]-6-iodonaphthalene-2-carboxamide hydrochloride salt (71)

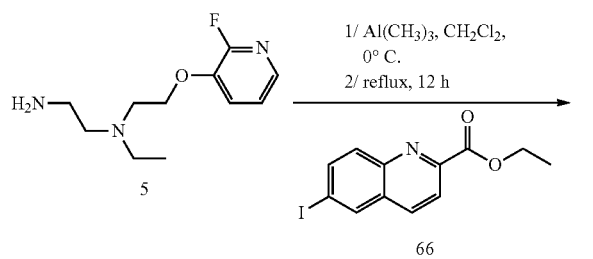

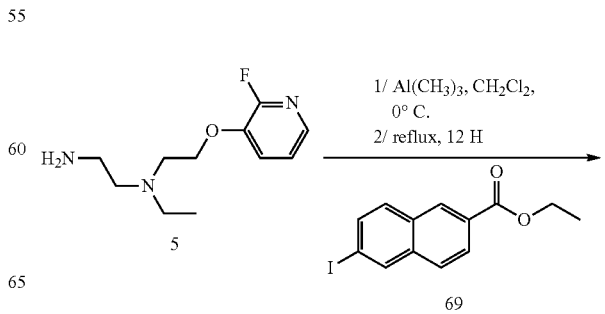

-continued

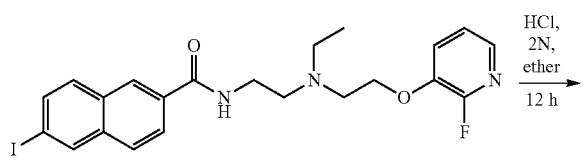

70

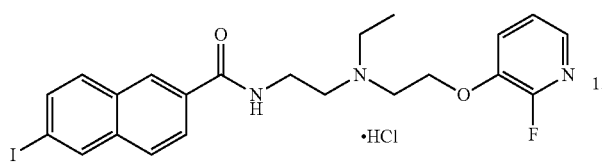

71

N-[2-[N-ethyl-N-[2-(2-fluoropyridin-3-yloxy)ethyl]amino]ethyl]-6-iodonaphthalene-2-carboxamide (70)

This compound was prepared, starting from compound 5 (200 mg, 0.88 mmol) and ethyl 6-iodonaphthalene-2-carboxylate (69) (194 mg, 0.62 mmol), according to the procedure developed for compound 10. Reaction time under reflux: 12 h; the purification was performed using column chromatography (Al$_2$O$_3$, CH$_2$C$_2$/EtOH, 99.5/0.5, v/v) to give compound 70 (188 mg, 0.37 mmol) as a brown oil. Yield 60%; R$_f$ (Al$_2$O$_3$, CH$_2$Cl$_2$/EtOH, 99.5/0.5, v/v) 0.47; IR (CCl$_4$) ν 1121, 1188, 1246, 1283, 1465, 1515, 1662, 2700-3000, 3250-3400 cm$^{-1}$; $^1$H NMR (200 MHz, CDCl$_3$) δ 1.10 (t, 3H, J=7.1 Hz), 2.73 (q, 2H, J=7.1 Hz), 2.84 (t, 2H, J=5.7 Hz), 2.99 (t, 2H, J=5.2 Hz), 3.60 (q, 2H, J=5.7 Hz), 4.11 (t, 2H, J=5.2 Hz), 7.00 (ddd, 1H, $^5J_{H-F}$=0.7 Hz, J=4.9, 7.9 Hz), 7.14 (m, 1H), 7.19 (ddd, 1H, $^4J_{H-F}$=10.0 Hz, J=1.7, 7.9 Hz), 7.55 (d, 1H, J=8.6 Hz), 7.65 (m, 1H), 7.66 (d, 1H, J=8.9 Hz), 7.73 (dd, 1H, J=1.9, 8.9 Hz), 7.94 (dd, 1H, J=1.9, 8.9 Hz), 8.23 (se, 2H); ESI-MS m/z 507.9 [M+H]$^+$.

N-[2-[N-ethyl-N-[2-(2-fluoropyridin-3-yloxy)ethyl]amino]ethyl]-6-iodonaphthalene-2-carboxamide hydrochloride salt (71)

This compound was prepared, starting from compound 70 (150 mg, 0.30 mmol), according to the procedure developed for compound 11. Reaction time at room temperature: 12 h to give compound 71 (127 mg, 0.23 mmol) as a very hygroscopic beige solid. Yield 77%; mp 157-159° C.; IR (KBr) ν 1124, 1186, 1241, 1312, 1457, 1545, 1653, 2612, 3221 cm$^{-1}$; $^1$H NMR (200 MHz, DMSO-d) δ 1.32 (t, 3H, J=7.0 Hz), 3.44 (m, 4H), 3.74 (m, 4H), 4.58 (t, 2H, J=4.5 Hz), 7.29 (ddd, 1H, $^5J_{H-F}$=0.6 Hz, J=5.1, 7.7 Hz), 7.82 (m, 6H), 8.47 (s, 1H), 8.52 (s, 1H), 9.16 (te, 1H, J=4.9 Hz), 10.82 (se, 1H).

EXAMPLE 16

N-[2-[N-ethyl-N-[2-(2-fluoropyridin-3-yloxy)ethyl]amino]ethyl]-8-iodo-[1,6]naphthyridine-2-carboxamide dihydrochloride salt (74)

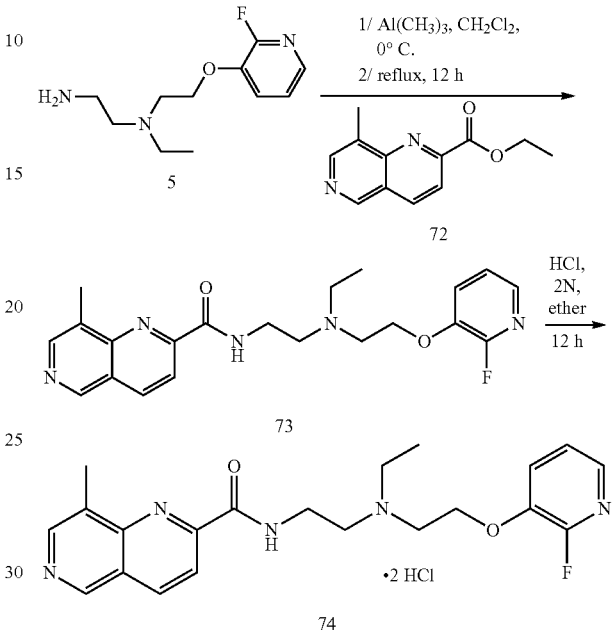

N-[2-[N-ethyl-N-[2-(2-fluoropyridin-3-yloxy)ethyl]amino]ethyl]-8-iodo-[1,6]naphthyridine-2-carboxamide (73)

This compound was prepared, starting from compound 5 (100 mg, 0.44 mmol) and ethyl 8-iodo-[1,6]naphthyridine-2-carboxylate (72) (102 mg, 0.31 mmol), according to the procedure developed for compound 10. Reaction time under reflux: 12 h; the purification was performed using column chromatography (Al$_2$O$_3$, CH$_2$Cl$_2$/EtOH, 99/1, v/v) to give compound 73 (151 mg, 0.30 mmol) as a yellow oil. Yield 96%; R$_f$(Al$_2$O$_3$, CH$_2$Cl$_2$/EtOH, 99/1, v/v) 0.65; IR (CCl$_4$) ν 1467, 1518, 1685, 2700-3000 cm$^{-}$: $^1$H NMR (200 MHz, CDCl$_3$) δ 1.10 (t, 3H, J=7.1 Hz), 2.71 (q, 2H, J=7.1 Hz), 2.83 (t, 2H, J=6.0 Hz), 2.97 (t, 2H, J=5.6 Hz), 3.59 (q, 2H, J=6.0 Hz), 4.12 (t, 2H, J=5.6 Hz), 6.82 (ddd, 1H, $^5J_{H-F}$=0.5 Hz, J=4.8, 7.9 Hz), 7.12 (ddd, 1H, $^4J_{H-F}$=10.1 Hz, J=1.6, 7.9 Hz), 7.43 (td, 1H, $^4J_{H-F}$=1.6 Hz, J=1.6, 4.8 Hz), 8.32 (d, 1H, J=8.4 Hz), 8.40 (d, 1H, J=8.4 Hz), 8.79 (m, 1H), 9.10 (s, 1H), 9.13 (s, 1H); ESI-MS m/z 509.9 [M+H]$^+$.

N-[2-[N-ethyl-N-[2-(2-fluoropyridin-3-yloxy)ethyl]amino]ethyl]-8-iodo-[1,6]naphthyridine-2-carboxamide dihydrochloride salt (74)

This compound was prepared, starting from compound 73 (100 mg, 0.20 mmol), according to the procedure developed for compound 11. Reaction time at room temperature: 12 h to give compound 74 (99 mg, 0.17 mmol) as a very hygroscopic yellow solid. Yield 87%; mp 131-133° C. (dec.); IR (KBr) ν 1287, 1455, 1521, 1606, 1678, 2300-2750, 2800-3100, 3200-3500 cm$^{-1}$; $^1$H NMR (200 MHz, DMSO-d$_6$) δ 1.34 (t, 3H, J=7.1 Hz), 3.38 (m, 2H), 3.48 (m, 2H), 3.71 (m, 2H), 3.91 (q, 2H, J=6.1 Hz), 4.60 (t, 2H, J=4.6 Hz), 7.27 (dd, 1H, J=4.5, 8.2 Hz), 7.70 (m, 1H), 7.73 (d, 1H, J=4.5 Hz), 8.31 (d, 1H, J=8.4 Hz), 8.80 (d, 1H, J=8.4 Hz), 8.96 (t, 1H, J=6.0 Hz), 9.28 (s, 1H), 9.48 (s, 1H), 11.2 (se, 1H); ESI-MS m/z 509.9 [M+H]$^+$.

EXAMPLE 17

N-[2-[N-ethyl-N-[2-(2-fluoropyridin-3-yloxy)ethyl]amino]ethyl]-6-iodoimidazo[1,2-a]pyridine-2-carboxamide dihydrochloride salt (77)

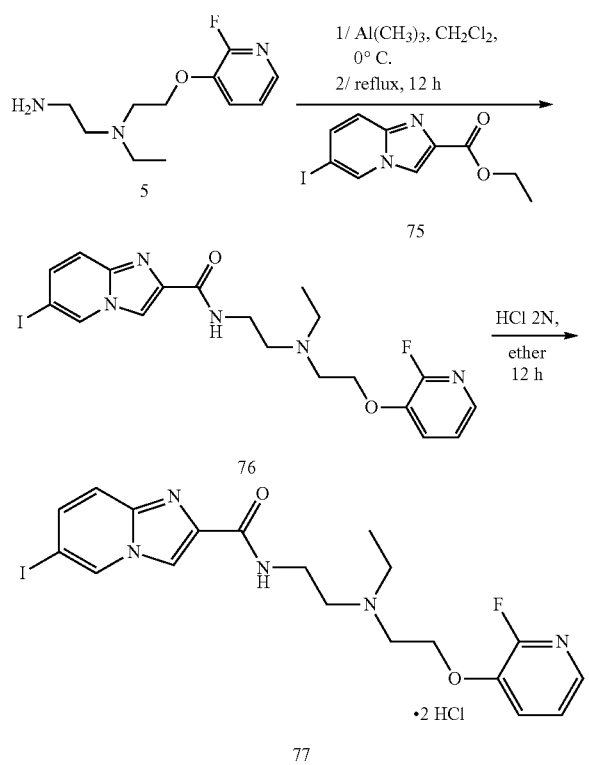

N-[2-[N-ethyl-N-[2-(2-fluoropyridin-3-yloxy)ethyl]amino]ethyl]-6-iodoimidazo[1,2-a]pyridine-2-carboxamide (76)

This compound was prepared, starting from compound 5 (100 mg, 0.44 mmol) and ethyl 6-iodoimidazo[1,2-a]pyridine-2-carboxylate (75) (197 mg, 0.62 mmol) (Sunberg, R. J.; Biswas, S.; Murthi, K. K.; Rowe D.; McCall, J. W.; Dzimianski, M. T. Bis-cationic heteroaromatics as macrofilaricides: synthesis of bis-amidine and bis-guanylhydrazone derivatives of substituted imidazo[1,2-a]pyridines. *J. Med. Chem.* 1998, 41, 4317-4328.), according to the procedure developed for compound 10. Reaction time under reflux: 12 h; the purification was performed using column chromatography (Al$_2$O$_3$, CH$_2$Cl$_2$/EtOH, 98/2, v/v) to give compound 76 (180 mg, 0.36 mmol) as a yellow oil. Yield 58%; R$_f$ (Al$_2$O$_3$, CH$_2$Cl$_2$/EtOH, 98/2, v/v) 0.61; IR (CCl$_4$) v 1249, 1283, 1466, 1564, 1669, 2800-3000, 3411 cm$^{-1}$; $^1$H NMR (200 MHz, CDCl$_3$) δ 1.08 (t, 3H, J=7.1 Hz), 2.71 (q, 2H, J=7.1 Hz), 2.81 (t, 2H, J=6.0 Hz), 2.97 (t, 2H, J=5.9 Hz), 3.55 (q, 2H, J=6.0 Hz), 4.11 (t, 2H, J=5.9 Hz), 6.98 (dd, 1H, J=4.8, 7.8 Hz), 7.23 (d, 1H, J=9.6 Hz), 7.31 (m, 1H), 7.34 (dd, 1H, J=1.6, 9.6 Hz), 7.64 (td, 1H, $^4$J$_{H-F}$=1.5 Hz, J=1.5, 4.8 Hz), 7.77 (m, 1H), 8.09 (s, 1H), 8.43 (se, 1H); ESI-MS m/z 497.9 [M+H]$^+$.

N-[2-[N-ethyl-N-[2-(2-fluoropyridin-3-yloxy)ethyl]amino]ethyl]-6-iodoimidazo[1,2-a]pyridine-2-carboxamide dihydrochloride salt (77)

This compound was prepared, starting from compound 76 (0.15 g, 0.30 mmol), according to the procedure developed for compound 11. Reaction time at room temperature: 12 h to give compound 77 (157 mg, 0.28 mmol) as a very hygroscopic beige solid. Yield 91%; mp 143-145° C.; IR (KBr) v 1291, 1456, 1559, 1675, 2500-3600 cm$^{-1}$; ESI-MS m/z 497.9 [M+H]$^+$.

EXAMPLE 18

N-[2-[N-ethyl-N-[2-(2-fluoropyridin-3-yloxy)ethyl]amino]ethyl]-7-iodoacridone-4-carboxamide hydrochloride salt (80)

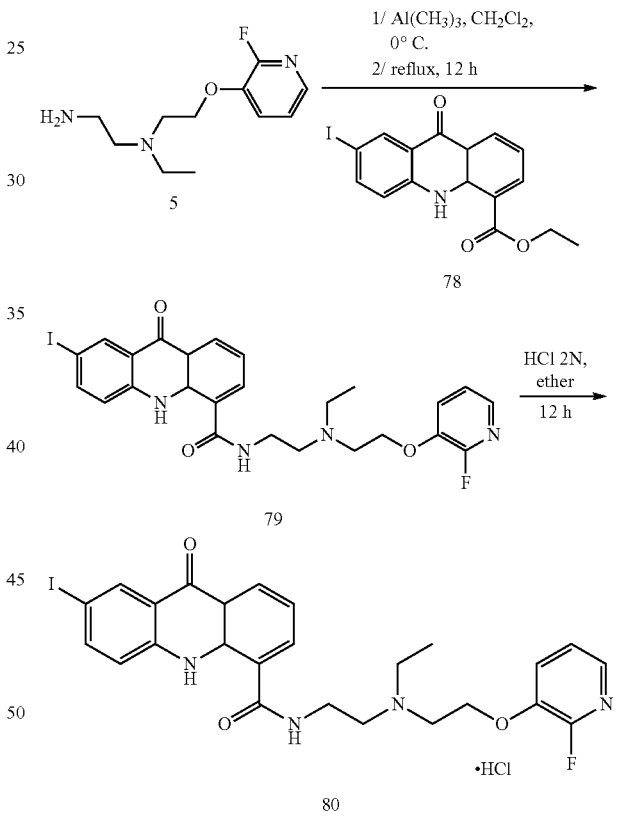

N-[2-[N-ethyl-N-[2-(2-fluoropyridin-3-yloxy)ethyl]amino]ethyl]-7-iodoacridone-4-carboxamide dihydrochloride (79)

This compound was prepared, starting from compound 5 (200 mg, 0.88 mmol) and ethyl 7-iodoacridone-4-carboxylate (78) (244 mg, 0.62 mmol), according to the procedure developed for compound 10. Reaction time under reflux: 12 h; the purification was performed using column chromatography (Al$_2$O$_3$, CH$_2$Cl$_2$/EtOH, 99/1, v/v) to give compound 79 (316 mg, 0.55 mmol) as a yellow oil. Yield 89° %; R$_f$ (Al$_2$O$_3$, CH$_2$Cl$_2$/EtOH, 99/1, v/v) 0.46; IR (CCl$_4$) ν 1283, 1452, 1514, 1593, 1611, 1652, 2930 cm$^{-1}$; $^1$H NMR (200 MHz, CDCl$_3$) δ 1.09 (t, 3H, J=7.1 Hz), 2.73 (q, 2H, J=7.1 Hz), 2.87 (t, 2H, J=5.9 Hz), 2.99 (t, 2H, J=5.1 Hz), 3.58 (q, 2H, J=5.9 Hz), 4.12 (t, 2H, J=5.1 Hz), 7.01 (m, 1H), 7.03 (t, 1H, J=7.9 Hz), 7.10 (d, 1H, J=8.7 Hz), 7.23 (ddd, 1H, $^4$J$_{H-F}$=10.1 Hz, J=1.6, 8.0 Hz), 7.63 (m, 1H), 7.67 (td, 1H, $^4$J$_{H-F}$=1.6 Hz, J=1.6, 4.9 Hz), 7.82 (m, 2H), 8.42 (dd, 1H, J=1.1, 7.9 Hz), 8.62 (d, 1H, J=2.0 Hz), 12.47 (s, 1H); ESI-MS m/z 575.0 [M+H]$^+$.

N-[2-[N-ethyl-N-[2-(2-fluoropyridin-3-yloxy)ethyl]amino]ethyl]-7-iodoacridone-4-carboxamide hydrochloride salt (80)

This compound was prepared, starting from compound 79 (100 mg, 0.17 mmol), according to the procedure developed for compound 11. Reaction time at room temperature: 12 h to give compound 80 (87 mg, 0.14 mmol) as a very hygroscopic yellow solid. Yield 82%; mp 205-207° C.; IR (KBr) ν 1123, 1187, 1299, 1449, 1517, 1587, 1613, 1649, 2400-2800, 2850-3300 cm$^{-1}$; $^1$H NMR (200 MHz, DMSO-d$_6$) δ 1.34 (t, 3H, J=7.0 Hz), 3.40-3.51 (m, 4H), 3.73 (m, 2H), 3.81 (m, 2H), 4.59 (m, 2H), 7.27 (m, 1H), 7.37 (d, 1H, J=7.8 Hz), 7.58 (d, 1H, J=8.7 Hz), 7.71 (m, 2H), 8.00 (dd, 1H, J=2.0, 8.7 Hz), 8.43 (m, 2H), 9.44 (se, 1H), 10.74 (se, 1H), 12.36 (s, 1H); ESI-MS m/z 575.0 [M+H]$^+$.

EXAMPLE 19

N-[2-[N-ethyl-N-[2-(2-fluoropyridin-3-yloxy)ethyl]amino]ethyl]-7-iodophenazine-1-carboxamide dihydrochloride salt (85)

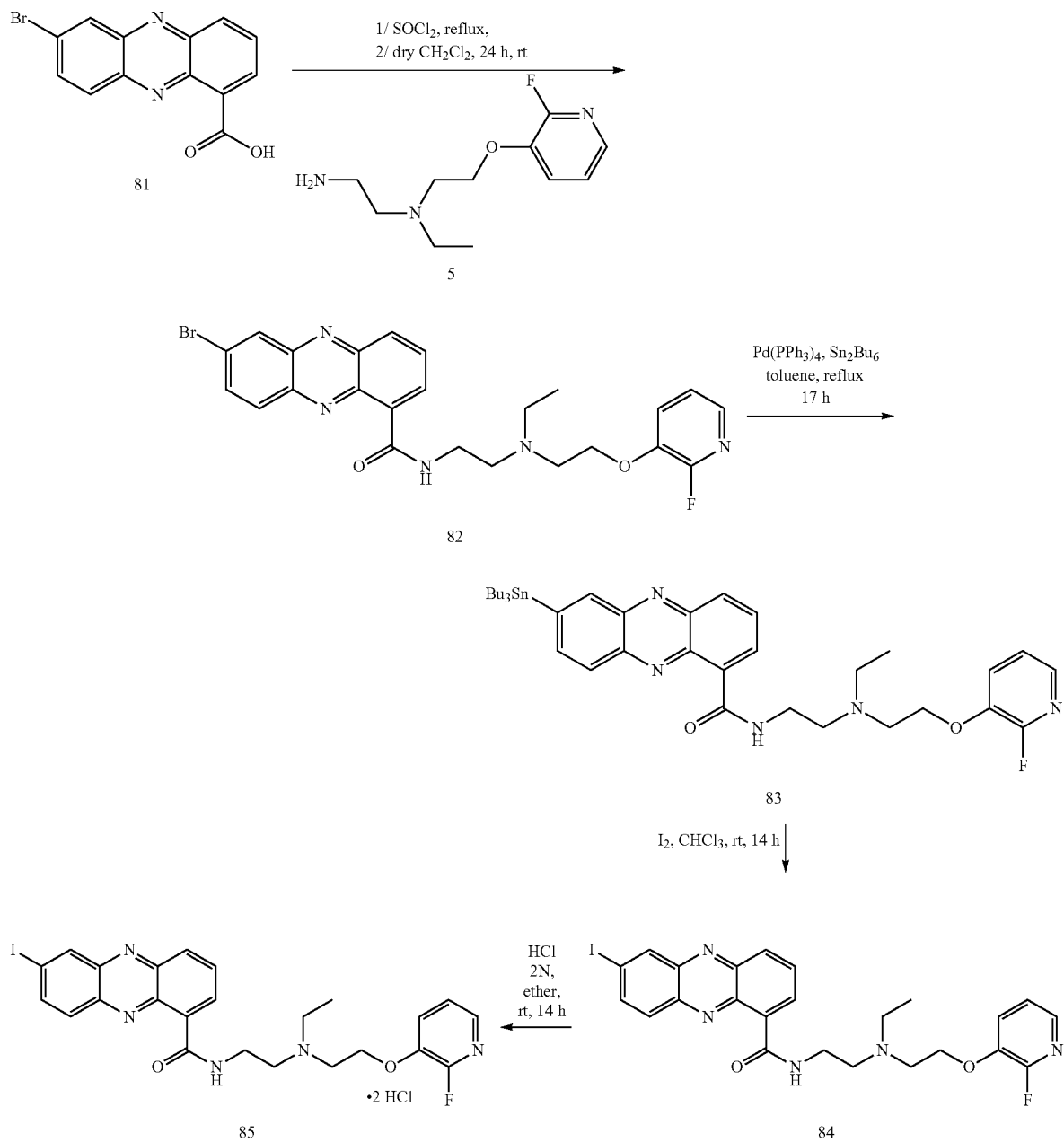

N-[2-[N-ethyl-N-[2-(2-fluoropyridin-3-yloxy)ethyl]amino]ethyl]-7-bromo phenazine-1-carboxamide (82)

A solution of 7-bromophenazine-1-carboxylic acid (81) (333 mg, 1.10 mmol) (Madelmont, J. C.; Chezal, J. M.: Moins, N.; Teulade, J. C.; Chavignon, O. Labelled analogues of halobenzamides as radiopharmaceuticals, WO 2008/012782A3) in thionyl chloride (8 mL) was refluxed, under argon, for 1 h. After cooling to room temperature, the solvent was evaporated under reduce pressure and the residue was dissolved in anhydrous toluene (5 mL). The solvent was evaporated under vacuum and the residue was dissolved in anhydrous dichloromethane (11 mL). A solution of compound 5 (300 mg, 1.32 mmol) in anhydrous dichloromethane (5 mL) was added, at 0° C. and the mixture was then stirred at room temperature for 24 h. The solvent was evaporated under reduce pressure and the residue was chromatographed ($Al_2O_3$, AcOEt) to give compound 82 (537 mg, 1.05 mmol) as a yellow oil. Yield 95%; $R_f$ ($Al_2O_3$, AcOEt) 0.69; IR ($CCl_4$) ν 1190, 1249, 1283, 1466, 1517, 1663, 2800-3000, 3250-3350 $cm^{-1}$; $^1$H NMR (200 MHz, $CDCl_3$) δ 1.09 (t, 3H, J=7.1 Hz), 2.80 (q, 2H, J=7.1 Hz), 2.86 (t, 2H, J=6.0 Hz), 3.00 (t, 2H, J=5.5 Hz), 3.70 (q, 2H, J=6.0 Hz), 4.04 (t, 2H, J=5.5 Hz), 6.75 (ddd, 1H, $^5J_{H-F}$=0.8 Hz, J=4.8, 7.9 Hz), 6.93 (ddd, 1H, $^4J_{H-F}$=10.1 Hz, J=1.5, 7.9 Hz), 7.45 (td, 1H, $^4J_{H-F}$=1.5 Hz, J=1.5, 4.8 Hz), 7.71 (dd, 1H, J=2.0, 9.2 Hz), 7.82 (dd, 1H, J=7.1, 8.7 Hz), 7.89 (d, 1H, J=9.2 Hz), 8.15 (dd, 1H, J=1.5, 8.7 Hz), 8.23 (d, 1H, J=2.0 Hz), 8.84 (dd, 1H, J=1.5, 7.1 Hz), 10.79 (m, 1H); ESI-MS m/z 512.0 $[M+H]^+$.

N-[2-[N-ethyl-N-[2-(2-fluoropyridin-3-yloxy)ethyl]amino]ethyl]-7-(tributylstannyl)phenazine-1-carboxamide (83)

To a solution of compound 82 (0.60 g, 1.17 mmol) in anhydrous toluene (20 mL), beforehand degassed under argon, were successively added, hexabutylditin (587 µL, 1.56 mmol) and freshly prepared tetrakis(triphenylphosphine)palladium(0) (20 mg) (Coulson, D. R.; Satek, L. C.; Grim, S. O. Tetrakis (Triphenylphosphine) Palladium (0) Inorg. Synth. 1971, 13, 121-124). The resulting solution was refluxed for 17 h under argon. After cooling to room temperature, the mixture was filtered through Celite® 521, washed with toluene (3×100 mL) and the filtrate was evaporated under vacuum. The residue obtained was then chromatographed ($Al_2O_3$, AcOEt/cyclohexane, 7/3, v/v) to give compound 83 (381 mg, 0.53 mmol) as a yellow oil. Yield 45%; $R_f$ ($Al_2O_3$, AcOEt/cyclohexane, 7/3, v/v) 0.72; IR ($CCl_4$) ν 1377, 1465, 1661, 2870, 2927, 2959 $cm^{-1}$;

$^1$H NMR (200 MHz, $CDCl_3$) δ 0.81 (t, 9H, J=7.2 Hz), 1.11 (m, 9H), 1.29 (m, 6H), 1.50 (m, 6H), 2.82 (m, 4H), 2.99 (t, 2H, J=5.7 Hz), 3.71 (q, 2H, J=5.6 Hz), 4.05 (t, 2H, J=5.7 Hz), 6.69 (dd, 1H, J=4.8, 7.8 Hz), 6.89 (m, 1H), 7.44 (m, 1H), 7.80 (m, 2H), 8.04 (d, 1H, J=8.5 Hz), 8.25 (dd, 1H, J=1.5, 8.7 Hz), 8.29 (s, 1H), 8.86 (dd, 1H, J=1.4, 7.2 Hz), 11.13 (m, 1H); ESI-MS m/z 724.3 $[M+H]^+$.

N-[2-[N-ethyl-N-[2-(2-fluoropyridin-3-yloxy)ethyl]amino]ethyl]-7-iodophenazine-1-carboxamide (84)

To a stirred solution of compound 83 (270 mg, 0.37 mmol) in chloroform (7 mL), was added during 4 h, a solution of diiodine (192 mg, 0.76 mmol) in chloroform (14 mL), dropwise. The mixture was then stirred 14 h at room temperature before addition of an aqueous saturated sodium carbonate solution (40 mL). The solution was decanted and the organic layer was washed with a 5% aqueous sodium hydrogenosulfite solution (2×15 mL), dried on magnesium sulfate, filtered and evaporated under vacuum. The residue was chromatographed ($Al_2O_3$, AcOEt/cyclohexane, 7/3, v/v) to give compound 84 (112 mg, 0.20 mmol) as a yellow oil. Yield 54%; $R_f$ ($Al_2O_3$, AcOEt/cyclohexane, 7/3, v/v) 0.68; IR ($CCl_4$) ν 1119, 1189, 1246, 1286, 1458, 1509, 1649, 2800-3000, 3246 $cm^{-1}$; $^1$H NMR (200 MHz, $CDCl_3$) δ 1.14 (t, 3H, J=7.1 Hz), 2.86 (m, 4H), 3.05 (t, 2H, J=5.5 Hz), 3.76 (q, 2H, J=5.5 Hz), 4.10 (t, 2H, J=5.5 Hz), 6.80 (dd, 1H, J=4.9, 7.9 Hz), 6.97 (m, 1H), 7.53 (m, 1H), 7.83 (dd, 1H, J=1.4, 9.2 Hz), 7.93 (m, 2H), 8.25 (dd, 1H, J=1.5, 8.7 Hz), 8.60 (se, 1H), 8.92 (dd, 1H, J=1.5, 7.2 Hz), 10.92 (m, 1H); ESI-MS m/z 560.0 $[M+H]^+$.

N-[2-[N-ethyl-N-[2-(2-fluoropyridin-3-yloxy)ethyl]amino]ethyl]-7-iodophenazine-1-carboxamide dihydrochloride salt (85)

This compound was prepared, starting from compound 84 (100 mg, 0.18 mmol), according to the procedure developed for compound 11. Reaction time at room temperature: 14 h to give compound 85 (78 mg, 0.12 mmol) as a very hygroscopic orange solid. Yield 69%; mp 127-129° C. (dec.); IR (KBr) ν 1123, 1285, 1342, 1466, 1654, 2000-2750, 3100-3500 $cm^{-1}$; $^1$H NMR (200 MHz, DMSO-$d_6$) δ 1.35 (t, 3H, J=6.9 Hz), 3.42 (m, 2H), 3.58 (m, 2H), 3.73 (m, 2H), 4.00 (m, 2H), 4.59 (m, 2H), 7.18 (dd, 1H, J=4.9, 7.8 Hz), 7.63 (m, 2H), 8.06 (t, 1H, J=8.2 Hz), 8.23 (d, 1H, J=9.2 Hz), 8.39 (m, 2H), 8.65 (d, 1H, J=7.0 Hz), 8.73 (s, 1H), 10.51 (m, 1H), 11.14 (se, 1H); ESI-MS m/z 560.0 $[M+H]^+$.

EXAMPLE 20

N-[[4-N,N-diethylaminomethyl)-2-fluoropyridin-3-yl]methyl]-6-iodoquinoxaline-2-carboxamide dihydrochloride salt (92)

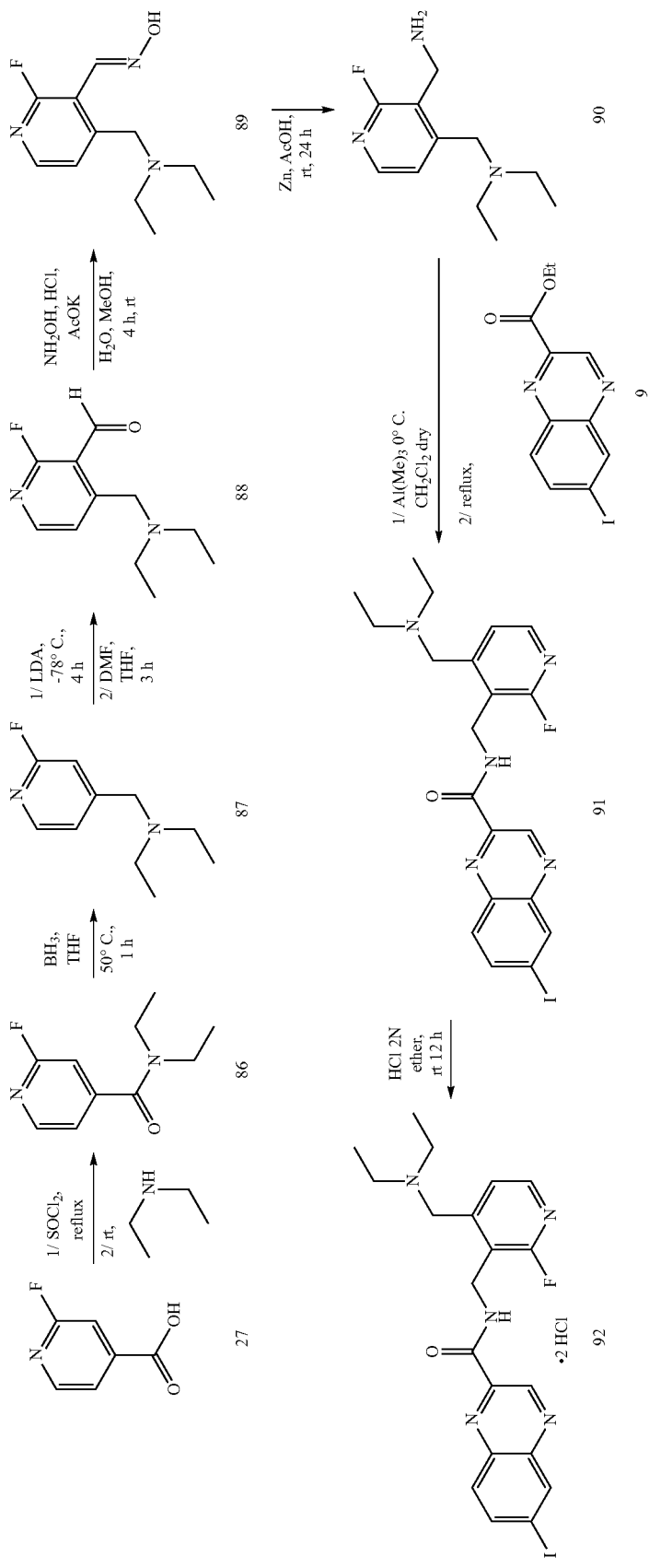

N,N-diethyl-2-fluoroisonicotinamide (86)

To a stirred suspension of compound 27 (6.00 g, 42.5 mmol) in anhydrous dichloromethane (200 mL) were successively added, under argon, anhydrous N,N-dimethylformamide (2 mL) and thionyl chloride (12.4 mL, 0.17 mol). The mixture was refluxed for 3 h. After cooling to room temperature, the solvent was evaporated under reduce pressure and the residue was dissolved in anhydrous toluene (40 mL). The solvent was evaporated under vacuum and the residue was dissolved in anhydrous tetrahydrofuran (40 mL). A solution of diethylamine (8.79 mL, 85.0 mmol) in anhydrous tetrahydrofuran (10 mL) was added dropwise, at 0° C. The mixture was then stirred at room temperature for 12 h. The solvent was evaporated under reduce pressure and the residue was dissolved in water (80 mL) before addition of a 5% aqueous sodium carbonate solution (10 mL). The mixture was extracted with dichloromethane (4×80 mL). The organic layers were combined, dried on magnesium sulfate, filtered and evaporated under vacuum. The residue was chromatographed ($Al_2O_3$, AcOEt) to give compound 86 (5.66 g, 28.8 mmol) as a yellow liquid. Yield 68%; $R_f$ ($Al_2O_3$, AcOEt) 0.78; IR ($CCl_4$) ν 1298, 1401, 1433, 1562, 1612, 1647, 2936, 2978 $cm^{-1}$; $^1H$ NMR (200 MHz, $CDCl_3$) δ 1.00 (t, 3H, J=7.1 Hz), 1.12 (t, 3H, J=7.1 Hz), 3.09 (q, 2H, J=7.1 Hz), 3.42 (q, 2H, J=7.1 Hz), 6.80 (m, 1H), 7.05 (ddd, 1H, $^5J_{H-F}$=1.9 Hz, J=1.3, 5.1 Hz), 8.15 (d, 1H, J=5.1 Hz); MS m/z 196 ($M^+$, 22), 195 (26), 124(100), 96 (36), 76 (11), 69 (12).

N,N-diethyl-N-[(2-fluoropyridin-4-1)methyl]amine (87)

To a solution of compound 86 (0.50 g, 2.55 mmol) in anhydrous tetrahydrofuran (6 mL) was added, under argon, at 0° C., a 1 M borane solution in anhydrous tetrahydrofuran (7.65 mL, 7.65 mmol). The mixture was heated at 50° C. for 1 h. After cooling to room temperature, were added dropwise successively at 0° C., methanol (5 mL) and a 1 M aqueous sodium hydroxide solution (5 mL). The mixture was heated at 50° C. for 5 h. After cooling to room temperature, the mixture was extracted with dichloromethane (3×10 mL). The organic layers were combined, dried on magnesium sulfate, filtered and evaporated under reduce pressure. The residue was chromatographed ($Al_2O_3$, $CH_2Cl_2$) to give compound 87 (0.42 g, 2.30 mmol) as a colourless liquid. Yield 91%; $R_f$ ($Al_2O_3$, $CH_2Cl_2$) 0.51; IR ($CCl_4$) ν 1167, 1278, 1410, 1571, 1612, 2300, 2805, 2973 $cm^{-1}$; $^1H$ NMR (200 MHz, $CDCl_3$) δ 1.27 (t, 6H, J=7.1 Hz), 2.76 (q, 4H, J=7.1 Hz), 3.82 (s, 2H), 7.21 (s, 1H), 7.41 (m, 1H), 8.35 (d, 1H, J=5.1 Hz); MS m/z 182 ($M^+$, 12), 167 (100), 110 (46), 86 (12), 83 (12), 56 (15).

4-(N,N-diethylaminomethyl)-2-fluoropyridine-3-carbaldehyde (88)

To a solution of anhydrous diisopropylamine (3.39 mL, 24.0 mmol) in anhydrous tetrahydrofuran (130 mL) was added dropwise under argon and at −78° C., a 2.5 M n-butyllithium solution in hexane (9.60 mL, 24.0 mmol). The mixture was stirred at −78° C. for 1 h before addition of a solution of compound 87 (4.00 g, 21.9 mmol) in anhydrous tetrahydrofuran (65 mL) dropwise. The mixture was stirred at −78° C. for 7 h before addition of anhydrous N,N-dimethylformamide (1.86 mL, 24.0 mmol). The mixture was stirred 5 min at −78° C. before rapid return back to a temperature comprised between and 10° C. An aqueous saturated ammonium chloride solution (300 mL) was added, the solution was decanted and the aqueous layer was extracted with dichloromethane (4×100 mL). The organic layers were combined, dried on magnesium sulfate, filtered and evaporated under vacuum. The residue was chromatographed ($Al_2O_3$, AcOEt/cyclohexane, 6/4, v/v) to give compound 88 (2.83 g, 13.5 mmol) as a colourless liquid. Yield 61%; $R_f$ ($Al_2O_3$, AcOEt/cyclohexane, 6/4, v/v) 0.56; IR ($CCl_4$) ν 1269, 1393, 1465, 1553, 1604, 1705, 1741, 2700-3000 $cm^{-1}$; $^1H$ NMR (200 MHz, $CDCl_3$) δ 1.01 (t, 6H, J=7.1 Hz), 2.54 (q, 4H, J=7.1 Hz), 3.96 (s, 2H), 7.71 (d, 1H, J=5.1 Hz), 8.29 (d, 1H, J=5.1 Hz), 10.41 (s, 1H); MS m/z 210 ($M^+$, 24), 195 (13), 181 (49), 167 (38), 153 (46), 138 (100), 133 (28), 110 (37), 83 (27), 72 (79), 58 (34).

4-(N,N-diethylaminomethyl)-2-fluoropyridine-3-carbaldehyde oxime (89)

To a solution of compound 88 (150 mg, 0.71 mmol) in methanol (2 mL) was added a solution of hydroxylamine hydrochloride (74 mg, 1.07 mmol) and potassium acetate (105 mg, 1.07 mmol) in water (7 mL). The mixture was stirred at room temperature for 4 h and the methanol was then evaporated under reduce pressure. A saturated aqueous sodium chloride solution (10 mL) was added and the mixture was extracted with dichloromethane (4×20 mL). The organic layers were combined, dried on magnesium sulfate, filtered and evaporated under vacuum. The residue was chromatographed ($Al_2O_3$, AcOEt→AcOEt/EtOH, 85/15, vi/v) to give compound 89 (131 mg, 0.58 mmol) as a white solid. Yield 81%; $R_f$ ($Al_2O_3$, AcOEt/EtOH, 85/15, v/v) 0.89; mp 97-99° C.; IR (KBr) ν 1264, 1331, 1392, 1605, 2750-2980, 3100, 3191 $cm^{-1}$; $^1H$ NMR (200 MHz, $CDCl_3$) δ 1.05 (t, 6H, J=7.1 Hz), 2.57 (q, 4H, J=7.1 Hz), 3.83 (s, 2H), 7.56 (d, 1H, J=5.1 Hz), 8.13 (d, 1H, J=5.1 Hz), 8.43 (s, 1H); ESI-MS m/z 225.8 $[M+H]^+$.

N,N-diethyl-N-[(3-aminomethyl-2-fluoropyridin-4-yl)methyl]amine (90)

To a stirred solution of compound 89 (1.30 g, 0.58 mmol) in acetic acid (34 mL), protected against light exposure, was added dropwise during 24 h, at room temperature, zinc dust (1.63 g, 24.9 mmol). The mixture was then cooled to 0° C. before addition of a 3 N aqueous sodium hydroxide solution (130 mL). After return back to room temperature, the mixture was extracted with dichloromethane (3×200 mL). The organic layers were combined, dried on magnesium sulfate, filtered and evaporated under reduce pressure. The residue was chromatographed ($Al_2O_3$, $CH_2Cl_2$/EtOH, 97/3, v/v) to give compound 90 (778 mg, 3.68 mmol) as a yellow oil. Yield 64%; $R_f$ ($Al_2O_3$, $CH_2Cl_2$/EtOH, 97/3, v/v) 0.54; IR ($CCl_4$) ν 1264, 1413, 1608, 2972 $cm^{-1}$; $^1H$ NMR (400 MHz, $CDCl_3$) δ 0.98 (t, 6H, J=7.3 Hz), 2.44 (q, 6H, J=7.1 Hz), 3.55 (s, 2H), 3.81 (s, 2H), 7.05 (d, 1H, J=4.9 Hz), 7.95 (d, 1H, J=4.9 Hz).

N-[[4-(N,N-diethylaminomethyl)-2-fluoropyridin-3-yl]methyl]-6-iodoquinoxaline-2-carboxamide (91)

This compound was prepared, starting from compounds 90 (0.70 g, 3.31 mmol) and 9 (1.09 g, 3.31 mmol), according to the procedure developed for compound 10. Reaction time under reflux: 12 h; the purification was performed using column chromatography ($Al_2O_3$, $CH_2Cl_2$/EtOH, 99/1, v/v) to give compound 91 (926 mg, 1.88 mmol) as a beige solid. Yield 57%; $R_f$ ($Al_2O_3$, $CH_2Cl_2$/EtOH, 99/1, v/v) 0.38; mp 147-149° C.; IR (KBr) ν 1160, 1413, 1477, 1508, 1679, 1679, 2967 $cm^{-1}$; $^1H$ NMR (400 MHz, $CDCl_3$) δ 1.13 (t, 6H, J=7.1 Hz), 2.66 (m, 4H), 3.80 (se, 2H), 4.82 (d, 2H, J=6.0 Hz), 7.19 (m, 1H), 7.71 (d, 1H, J=8.8 Hz), 8.02 (dd, 1H, J=1.8, 8.8 Hz), 8.08

(d, 1H, J=4.8 Hz), 8.55 (d, 1H, J=1.8 Hz), 9.14 (m, 1H), 9.61 (s, 1H); ESI-MS m/z 493.9 [M+H]$^+$.

N-[[4-N,N-diethylaminomethyl)-2-fluoropyridin-3-yl]methyl]-6-iodoquinoxaline-2-carboxamide dihydrochloride salt (92)

This compound was prepared, starting from compound 91 (0.30 g, 0.61 mmol) according to the procedure developed for compound 11. Reaction time at room temperature: 14 h to give compound 92 (311 mg, 0.55 mmol) as a very hygroscopic yellow solid. Yield 90%; mp 197-199° C.; IR (KBr) ν 1155, 1413, 1474, 1529, 1670, 2300-2600, 3027, 3261 cm$^{-1}$; $^1$H NMR (200 MHz, DMSO-d$_6$) δ 1.30 (t, 6H, J=7.0 Hz), 3.19 (m, 4H), 3.43 (s, 2H), 4.69 (t, 2H, J=5.3 Hz), 7.90 (m, 2H), 8.22 (dd, 1H, J=1.7, 8.9 Hz), 8.26 (d, 1H, J=5.2 Hz), 8.58 (d, 1H, J=1.7 Hz), 9.40 (s, 1H), 9.73 (m, 1H), 11.23 (m, 1H): ESI-MS m/z 493.9 [M+H]$^+$.

EXAMPLE 21

N-[2-(diethylamino)ethyl]-4-fluoro-6-iodoquinoline-3-carboxamide (96)

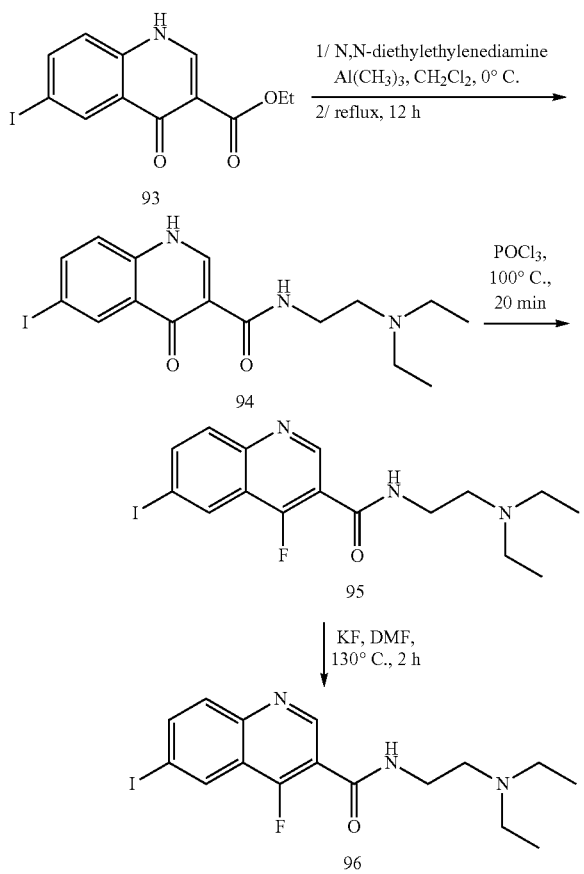

N-[2-(diethylamino)ethyl]-6-iodo-4-oxo-1,4-dihydroquinoline-3-carboxamide (94)

To a stirred solution of a 2.0 M trimethylaluminium solution in heptane (20.8 mL, 41.6 mmol) in anhydrous dichloromethane (350 mL) was added at 0° C., under argon, N,N-diethylethylenediamine (5.78 mL, 41.1 mmol) dropwise. After 10 min, ethyl 6-iodo-4-oxo-1,4-dihydroquinoline-3-carboxylate (93) (10.0 g, 31.4 mmol) (Edlin, C.; Eldred, C. D.; Lunniss, C. J.; Redgrave, A. J.; Robinson, J. E.; Woodrow, M. Preparation of aminocarbonylquinoline derivatives as phosphodiesterase type IV (PDE4) inhibitors. Patent WO2005030725, 2005) was added. The mixture was refluxed for 12 h. After cooling to room temperature, water (500 mL) was added and the precipitate was filtered and washed with ethanol (2×100 mL). The filtrate was evaporated under vacuum. The residue was chromatographed (Al$_2$O$_3$, CH$_2$Cl$_2$/EtOH, 94/6, v/v) to give amide 94 (9.70 g, 23.5 mmol) as a beige solid. Yield 81%; R$_f$(Al$_2$O$_3$, CH$_2$Cl$_2$/EtOH, 94/6, v/v) 0.32; mp 243-245° C.; IR (KBr) ν 1466, 1507, 1551, 1633, 2800-3000, 3062 cm$^{-1}$; $^1$H NMR (200 MHz, DMSO-d$_6$) δ 1.23 (t, 6H, J=7.1 Hz), 3.17 (q, 4H, J=7.1 Hz), 3.23 (t, 2H, J=6.8 Hz), 3.71 (q, 2H, J=6.4 Hz), 7.59 (d, 1H, J=8.6 Hz), 8.05 (dd, 1H, J=2.0, 8.6 Hz), 8.51 (d, 1H, J=2.0 Hz), 8.72 (s, 1H), 10.04 (t, 1H, J=5.8 Hz), 10.13 (se, 1H); ESI-MS m/z 413.8 [M+H]$^+$.

4-chloro-N-[2-(diethylamino)ethyl]-6-iodoquinoline-3-carboxamide (95)

A stirred solution of compound 94 (9.00 g, 21.8 mmol) in phosphorus oxychloride (50 mL) was heated at 100° C. for 20 min. After cooling to room temperature, the solvent was evaporated under vacuum. The residue was poured into crushed ice (100 g). A 10% aqueous sodium hydrogenocarbonate solution (100 mL) and dichloromethane (100 mL) were added successively at 0° C. The mixture was stirred until the brown oil was totally dissolved. The solution was decanted and the aqueous layer was then extracted with dichloromethane (3×200 mL). The organic layers were combined, dried on magnesium sulfate, filtered and evaporated under reduced pressure. The residue was chromatographed (Al$_2$O$_3$, AcOEt/cyclohexane, 9/1, v/v) to give compound 95 (7.12 g, 16.5 mmol) as a yellow solid. Yield 76%; R$_f$(Al$_2$O$_3$, AcOEt/cyclohexane, 9/1, v/v) 0.34; mp 76-78° C.: IR (KBr) ν 1329, 1477, 1558, 1636, 2798, 2966, 3300 cm$^{-1}$; $^1$H NMR (400 MHz, CDCl$_3$) δ 1.01 (t, 6H, J=7.1 Hz), 2.58 (q, 4H, J=7.1 Hz), 2.70 (t, 2H, J=5.8 Hz), 3.55 (q, 2H, J=5.8 Hz), 7.39 (se, 1H), 7.73 (d, 1H, J=8.8 Hz), 7.96 (dd, 1H, J=1.8, 8.8 Hz), 8.55 (d, 1H, J=1.8 Hz), 8.93 (s, 1H); MS m/z 433 (M+2, 2), 431 (M$^+$, 6), 417 (3), 415 (8), 317 (6), 315 (20), 289 (2), 287 (6), 189 (6), 161 (9), 128 (5), 99 (6), 86 (100), 72 (6), 56 (13).

N-[2-(diethylamino)ethyl]-4-fluoro-6-iodoquinoline-3-carboxamide (96)

Potassium fluoride (674 mg, 11.6 mmol) was dried under vacuum and stirring, at 200° C. for 3 h. After cooling to room temperature, a solution of compound 95 (1.00 g, 2.32 mmol) in anhydrous N,N-dimethylformamide (20 mL) was added. The mixture was then heated at 130° C., under argon, for 2 h. After cooling to room temperature, the solvent was evaporated under vacuum and the residue was chromatographed (Al$_2$O$_3$, AcOEt/cyclohexane, 9/1, v/v) to give compound 96 (0.50 g, 1.20 mmol) as a yellow solid. Yield 52%; R$_f$(Al$_2$O$_3$, AcOEt/cyclohexane, 9/1, v/v) 0.46; mp 88-90° C.; IR (KBr) ν 1105, 1342, 1518, 1656, 2830, 2966, 3405 cm$^{-1}$; $^1$H NMR (400 MHz, CDCl$_3$) δ 1.07 (t, 6H, J=7.1 Hz), 2.59 (q, 4H, J=7.1 Hz), 2.69 (t, 2H, J=5.9 Hz), 3.57 (q, 2H, J=5.9 Hz), 7.58 (se, 1H), 7.86 (d, 1H, J=9.0 Hz), 8.06 (dd, 1H, J=1.8, 9.0 Hz), 8.54 (d, 1H, J=1.8 Hz), 9.44 (d, 1H, $^4$J$_{H-F}$=10.6 Hz); MS m/z 415 (M$^+$, 1), 299 (3), 145 (1), 118 (3), 86 (100), 58 (9).

EXAMPLE 22

N-[2-(diethylamino)ethyl]-4-fluoro-6-iodoquinoline-8-carboxamide (102)

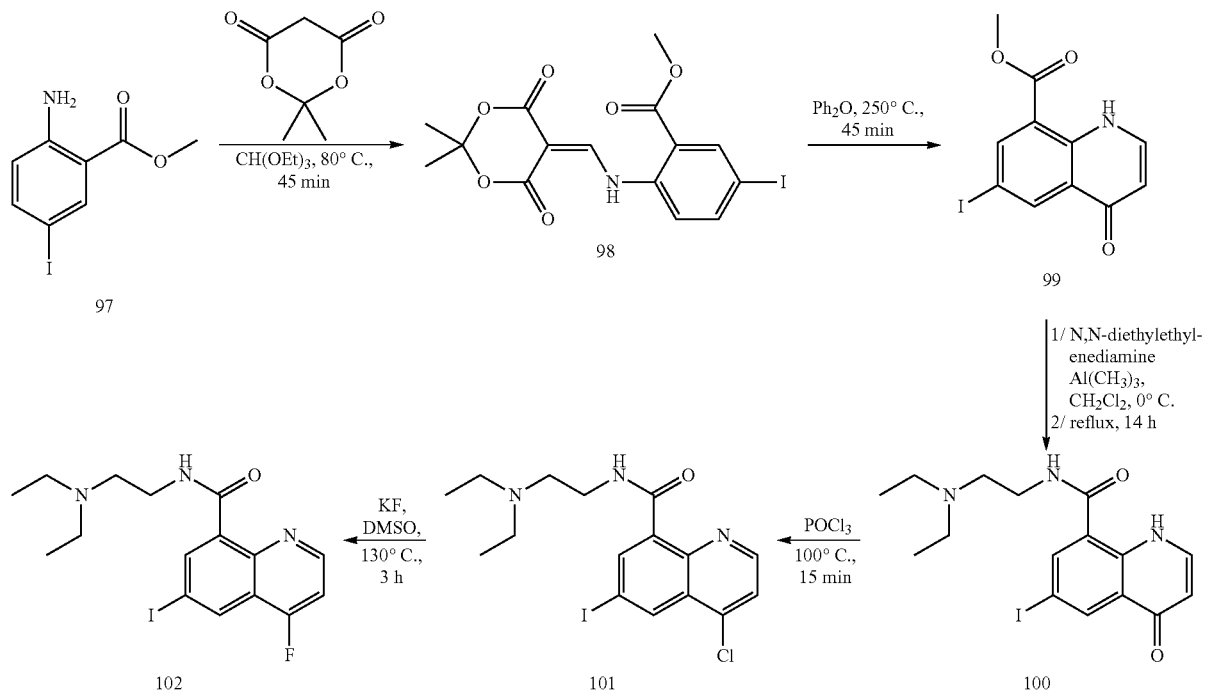

Methyl 2-[(2,2-dimethyl-4,6-dioxo-[1,3]dioxan-5-ylidenemethyl)amino]-5-iodobenzoate (98)

To a stirred solution of methyl 6-iodoanthranilate (97) (4.46 g, 16.1 mmol) in ethyl orthoformate (8.92 mL, 53.5 mmol) was added 2,2-dimethyl-1,3-dioxane-4,6-dione (1.16 g, 8.05 mmol). The mixture was stirred at 80° C. for 45 min. After cooling to room temperature, the yellow precipitate was filtered and washed with ethanol (2×10 mL) to give compound 98 (3.31 g, 7.68 mmol) as a yellow solid. Yield 95%; mp 206-208° C.; IR (KBr) ν 1198, 1227, 1251, 1284, 1429, 1585, 1607, 1685, 3100-3250 cm$^{-1}$; $^1$H NMR (200 MHz, CDCl$_3$) δ 1.07 (s, 6H), 3.98 (s, 3H), 7.23 (d, 1H, J=8.8 Hz), 7.86 (dd, 1H, J=2.0, 8.8 Hz), 8.38 (d, 1H, J=2.0 Hz), 8.65 (d, 1H, J=14.0 Hz), 13.1 (d, 1H, J=14.0 Hz).

Methyl 6-iodo-4-oxo-1,4-dihydroquinoline-8-carboxylate (99)

Compound 98 (3.00 g, 6.96 mmol) was added under argon to refluxing diphenylether (20 mL). The mixture was stirred at 250° C. for 45 min. After cooling to room temperature, the crude mixture was chromatographed (SiO$_2$). Diphenylether was first eliminated by elution with dichloromethane and the desired product was recovered using elution by gradient (CH$_2$Cl$_2$→CH$_2$C$_2$/EtOH (95/5, v/v)) to give compound 99 (2.01 g, 6.11 mmol) as a green solid. Yield 88%; R$_f$ (SiO$_2$, CH$_2$Cl$_2$/EtOH, 95/5, v/v) 0.31; mp 75-77° C.; IR (KBr) ν 1213, 1271, 1303, 1491, 1560, 1577, 1628, 1701, 3100-3300 cm$^{-1}$; $^1$H NMR (200 MHz, CDCl$_3$) δ 4.02 (s, 3H), 6.36 (dd, 1H, J=1.4, 7.6 Hz), 7.72 (dd, 1H, J=6.0, 7.6 Hz), 8.59 (d, 1H, J=2.2 Hz), 8.92 (d, 1H, J=2.2 Hz), 11.61 (se, 1H); ESI-MS m/z 329.7 [M+H]$^+$.

N-[2-(diethylamino)ethyl]-6-iodo-4-oxo-1,4-dihydroquinoline-8-carboxamide (100)

This compound was prepared, starting from compound 99 (2.00 g, 6.08 mmol) and N,N-diethylethylenediamine (1.21 mL, 8.56 mmol), according to the procedure developed for compound 10. Reaction time under reflux: 14 h; the purification was performed using column chromatography (Al$_2$O$_3$, CH$_2$Cl$_2$/EtOH, 96/4, v/v) to give compound 100 (2.17 g, 5.25 mmol) as a beige solid. Yield 86%; R$_f$ (Al$_2$O$_3$, CH$_2$Cl$_2$/EtOH, 96/4, v/v) 0.51; mp 141-143° C.; IR (KBr) ν 1392, 1491, 1560, 1617, 1641, 2800-3000, 3293 cm$^{-1}$; $^1$H NMR (200 MHz, CDCl$_3$) δ 1.07 (t, 6H, J=7.1 Hz), 2.62 (q, 4H, J=7.1 Hz), 2.71 (t, 2H, J=6.3 Hz), 3.50 (m, 2H), 6.30 (d, 1H, J=7.5 Hz), 7.64 (m, 2H), 8.07 (d, 1H, J=1.9 Hz), 8.79 (d, 1H, J=1.9 Hz); ESI-MS m/z 413.8 [M+H]$^+$.

4-chloro-N-[2-(diethylamino)ethyl]-6-iodoquinoline-8-carboxamide (101)

This compound was prepared, starting from compound 100 (2.00 g, 4.84 mmol), according to the procedure developed for compound 95. Reaction time at 100° C.: 15 min; the purification was performed using column chromatography (Al$_2$O$_3$, AcOEt/cyclohexane, 9/1, v/v) to give compound 101 (1.52 g, 3.52 mmol) as a beige solid. Yield 73%; R$_f$ (Al$_2$O$_3$, AcOEt/cyclohexane, 9/1, v/v) 0.49; mp 76-78° C.; IR (KBr) ν 1555, 1654, 2962 cm$^{-1}$; $^1$H NMR (200 MHz, CDCl$_3$) δ 1.09 (t, 6H, J=7.1 Hz), 2.64 (q, 4H, J=7.1 Hz), 2.75 (t, 2H, J=6.4 Hz), 3.66 (q, 2H, J=6.4 Hz), 7.54 (d. 1H, J=4.7 Hz), 8.68 (d, 1H, J=2.1 Hz), 8.76 (d, 1H, J=4.7 Hz), 9.07 (d, 1H, J=2.1 Hz), 11.01 (m, 1H); MS m/z 433 (M+2, 1), 431 (M$^+$, 1), 360 (1), 358 (1), 317 (1), 315 (3), 289 (1), 287 (1), 191 (1), 189 (2), 161 (3), 126 (2), 99 (9), 86 (100), 71 (2), 58 (9).

N-[2-(diethylamino)ethyl]-4-fluoro-6-iodoquinoline-8-carboxamide (102)

Potassium fluoride (725 mg, 12.5 mmol) was dried under vacuum and stirring, at 200° C. for 3 h. After cooling to room temperature, a solution of compound 101 (1.00 g, 2.32 mmol) in anhydrous dimethylsulfoxide (20 mL) was added. The mixture was then heated at 130° C., under argon, for 3 h. After cooling to room temperature, the solvent was evaporated under vacuum and the residue was chromatographed ($Al_2O_3$, AcOEt/cyclohexane, 9/1, v/v) to give compound 102 (821 mg, 1.98 mmol) as a yellow solid. Yield 85%; $R_f$ ($Al_2O_3$, AcOEt/cyclohexane, 9/1, v/v) 0.42; mp 79-81° C.; IR (KBr) ν 1529, 1667, 2798, 2966, 3200-3300 cm$^{-1}$; $^1$H NMR (200 MHz, CDCl$_3$) δ 1.04 (t, 6H, J=7.1 Hz), 2.59 (q, 4H, J=7.1 Hz), 2.70 (t, 2H, J=6.4 Hz), 3.61 (q, 2H, J=6.4 Hz), 7.15 (dd, 1H, $^3J_{H-F}$=9.2 Hz, J=5.1 Hz), 8.53 (d, 1H, J=2.1 Hz), 8.83 (dd, 1H, $^4J_{H-F}$=8.4 Hz, J=5.1 Hz), 9.05 (d, 1H, J=2.1 Hz), 11.04 (m, 1H); MS m/z 415 (M$^+$, 1), 342 (1), 299 (4), 271 (1), 173 (2), 145 (6), 118 (2), 99 (8), 86 (100), 58 (9).

EXAMPLE 23

N-[2-(diethylamino)ethyl]-4-fluoro-6-iodoquinoline-2-carboxamide (106)

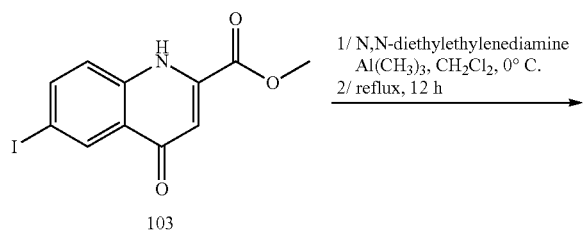

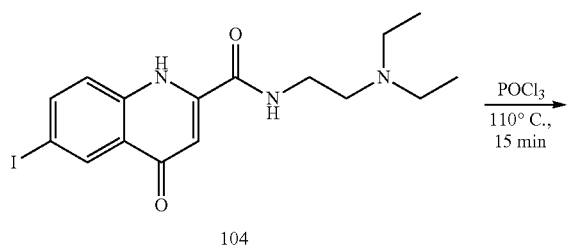

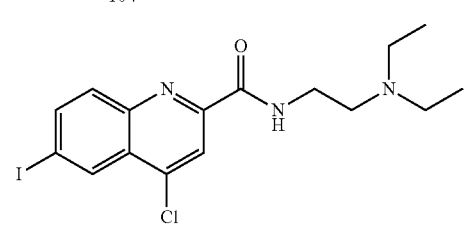

N-[2-(diethylamino)ethyl]-6-iodo-4-oxo-1,4-dihydroquinoline-2-carboxamide (104)

To a stirred solution of N,N-diethylethylenediamine (483 µL, 3.42 mmol) in anhydrous dichloromethane (50 mL) was added, at 0° C., under argon, a 2.0 M trimethylaluminium solution in heptane (1.71 mL, 3.42 mmol). After 10 min, methyl 6-iodo-4-oxo-1,4-dihydroquinoline-2-carboxylate (103) (800 mg, 2.43 mmol) (Deng, Y.; Curran, P. J.; Shipps, G. W. Jr.; Zhao, L.; Siddiqui, M. A.: Popovici-Muller, J.; Duca, J. S.; Kruza, A. W.; Fischmann, T. O.; Madison, V. S.; Zhang, R.; Mcnemar, C. W.; Mayhood, T. W.; Windsor, W. T.; Lees, E. M.; Parry, D. Novel high affinity quinoline-based kinase ligands. Patent WO2007/022241, 2007) was added and the mixture was refluxed for 12 h. After cooling to room temperature, water (40 mL) and ethanol (100 mL) were added. The precipitate was then filtered and washed with ethanol (5×10 mL). The filtrate volume was reduced to 20 mL by evaporation under reduce pressure and the precipitate formed was filtered and washed with diethylether (10 mL) to give compound 104 (784 mg, 1.90 mmol) as a beige solid. Yield 78%; mp 345-347° C. (dec.); IR (KBr) ν 1507, 1594, 1622, 1665, 2963, 3241 cm$^{-1}$; $^1$H NMR (200 MHz, DMSO-d$_6$) δ 0.96 (t, 6H, J=7.0 Hz), 2.53 (m, 6H), 3.34 (q, 2H, J=6.3 Hz), 6.83 (s, 1H), 7.72 (d, 1H, J=8.8 Hz), 7.94 (dd, 1H, J=2.0, 8.8 Hz), 8.36 (d, 1H, J=2.0 Hz), 8.91 (t, 1H, J=5.3 Hz); ESI-MS m/z 413.8 [M+H]$^+$.

4-chloro-N-[2-(diethylamino)ethyl]-6-iodoquinoline-2-carboxamide (105)

This compound was prepared, starting from compound 104 (0.34 g, 0.82 mmol), according to the procedure developed for compound 95. Reaction time at 100° C.: 15 min; the purification was performed using column chromatography ($Al_2O_3$, $CH_2Cl_2$/EtOH, 99/1, v/v) to give compound 105 (323 mg, 0.75 mmol) as a beige solid. Yield 91%; $R_f$ ($Al_2O_3$, $CH_2Cl_2$/EtOH, 99/1, v/v) 0.42; mp 64-66° C.: IR (KBr) ν 1182, 1297, 1386, 1479, 1518, 1691, 2811, 2965, 3354 cm$^{-1}$; $^1$H NMR (200 MHz, CDCl$_3$) δ 1.11 (t, 6H, J=7.1 Hz), 2.66 (q, 4H, J=7.1 Hz), 2.75 (t, 2H, J=6.2 Hz), 3.60 (q, 2H, J=6.1 Hz), 7.82 (d, 1H, J=8.9 Hz), 8.03 (dd, 1H, J=1.8, 8.9 Hz), 8.36 (s, 1H), 8.56 (m, 1H), 8.64 (d, 1H, J=1.8 Hz); ESI-MS m/z 431.8 [M+H]$^+$.

N-[2-(diethylamino)ethyl]-4-fluoro-6-iodoquinoline-2-carboxamide (106)

This compound was prepared, starting from compound 105 (1.00 g, 2.32 mmol), according to the procedure developed for compound 102. Reaction time at 200° C.: 2 h, reaction time at 140° C.: 5 h; the purification was performed using column chromagraphie ($Al_2O_3$, $CH_2Cl_2$/EtOH, 99/1, v/v) to give compound 106 (458 mg, 1.10 mmol) as a yellow solid.

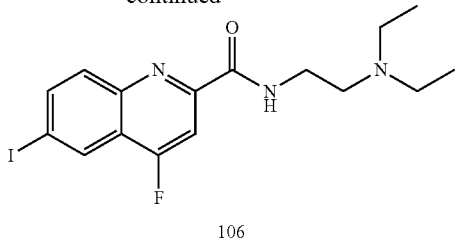

Yield 48%; $R_f$ (Al$_2$O$_3$, CH$_2$Cl$_2$/EtOH, 99/1, v/v) 0.42; mp 58-60° C.; IR (KBr) ν 1342, 1486, 1518, 1555, 1681, 2760, 2966, 3385 cm$^{-1}$; $^1$H NMR (200 MHz, CDCl$_3$) δ 1.06 (t, 6H, J=7.1 Hz), 2.56 (q, 4H, J=7.1 Hz), 2.69 (t, 2H, J=6.1 Hz), 3.54 (q, 2H, J=6.1 Hz), 7.76 (dd, 1H, $^5J_{H-F}$=1.2 Hz, J=8.9 Hz), 7.96 (m, 2H), 8.42 (d, 1H, J=1.7 Hz), 8.50 (m, 1H); ESI-MS m/z 415.9 [M+H]$^+$.

EXAMPLE 24

N-[2-(diethylamino)ethyl]-2-fluoro-6-iodoquinoline-4-carboxamide (110)

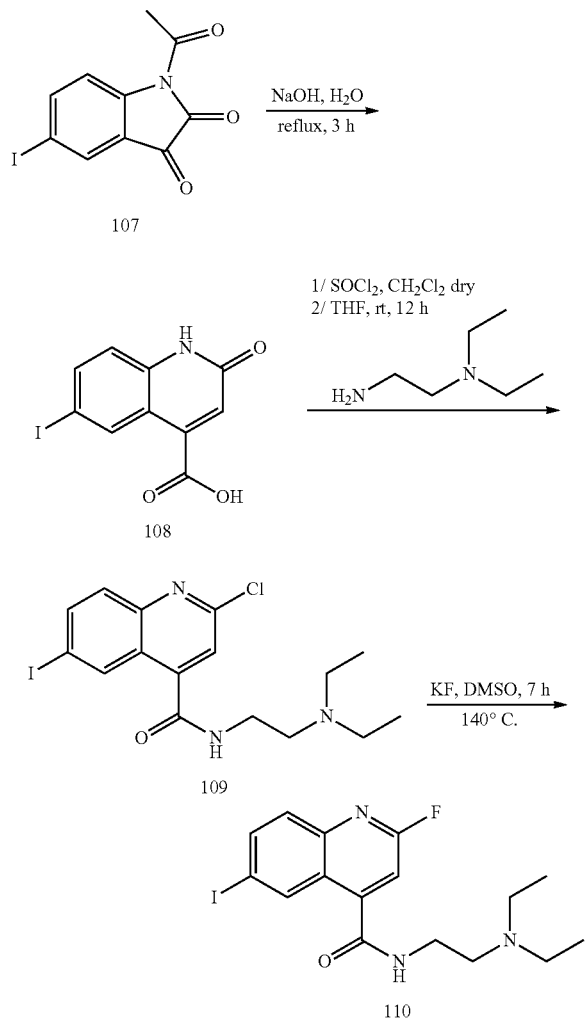

6-iodo-2-oxo-1,2-dihydroquinoline-4-carboxylic acid (108)

To a solution of sodium hydroxide (0.77 g, 19.3 mmol) in water (46.5 mL), was added N-acetyl-5-iodoisatine (107) (2.50 g, 7.86 mmol) (Aeschlimann, J. A. The relative stability of the quinolone and indolinone rings. *J. Chem. Soc.* 1926, 2908). The mixture was refluxed for 3 h. After cooling to room temperature and then 0° C., a 6 N aqueous hydrochloric acid solution was added (pH=1). The precipitate was filtered and suspended in a saturated aqueous sodium bicarbonate solution (10 mL). The remaining precipitate was filtered and the filtrate was extracted with dichloromethane (6×50 mL). The aqueous layer was acidified up to pH=1 with a 6 N aqueous hydrochloric acid solution and left 1 h at 0° C. The precipitate formed was filtered and dried under vacuum at 35° C. to give compound 108 (0.90 g, 2.86 mmol) as an ocher solid. Yield 36%; mp 361-363° C.; IR (KBr) ν 1219, 1636, 1701, 2800-3150, 3200-3500 cm$^{-1}$; $^1$H NMR (200 MHz, DMSO-d$_6$) δ 6.92 (s, 1H), 7.18 (d, 1H, J=8.7 Hz), 7.84 (dd, 1H, J=1.8, 8.7 Hz), 8.57 (d, 1H, J=1.8 Hz), 12.17 (s, 1H), 14.00 (m, 1H); ESI-MS m/z 313.7 [M−H].

2-chloro-N-[2-diethylamino)ethyl]-6-iodoquinoline-4-carboxamide (109)

To a suspension of compound 108 (150 mg, 0.48 mmol) in anhydrous dichloromethane (3 mL) were successively added, under argon, N,N-dimethylformamide (2 drops) and thionyl chloride (140 μL, 1.92 mmol). The mixture was refluxed for 3 h. After cooling to room temperature, the solvent was evaporated under reduce pressure. The residue was dissolved in anhydrous toluene (5 mL) and the solvent was evaporated under vacuum. The residue was dissolved, under argon, in anhydrous tetrahydrofuran (4 mL) before addition, at 0° C., of a solution of N,N-diethylethylenediamine (135 μL, 0.96 mmol) in anhydrous tetrahydrofuran (2 mL). The mixture was stirred 12 h at room temperature and the solvent was evaporated under vacuum. The residue was dissolved in water (5 mL) and a 10% aqueous sodium bicarbonate solution (3 mL) was added. The aqueous layer was extracted with dichloromethane (4×50 mL). The organic layers were combined, dried on magnesium sulfate, filtered and evaporated under reduce pressure. The residue was chromatographed (Al$_2$O$_3$, CH$_2$Cl$_2$/EtOH, 99/1, v/v) to give compound 109 (0.52 g, 1.20 mmol) as a beige solid. Yield 76%; $R_f$ (Al$_2$O$_3$, CH$_2$Cl$_2$/EtOH, 99/1. v/v) 0.38; mp 106-108° C.; IR (KBr) ν 1270, 1299, 1378, 1482, 1546, 1638, 2966, 3240 cm$^{-1}$; $^1$H NMR (200 MHz, CDCl$_3$) δ 1.03 (t, 6H, J=7.1 Hz), 2.58 (q, 4H, J=7.1 Hz), 2.69 (t, 2H, J=6.0 Hz), 3.55 (q, 2H, J=6.0 Hz), 7.19 (m, 1H), 7.35 (s, 1H), 7.64 (d, 1H, J=8.9 Hz), 7.94 (dd, 1H, J=1.8, 8.9 Hz), 8.53 (d, 1H, J=1.8 Hz).

N-[2-(diethylamino)ethyl]-2-fluoro-6-iodoquinoline-4-carboxamide (110)

Potassium fluoride (183 mg, 3.15 mmol) was dried under vacuum and stirring, at 200° C. for 3 h. After cooling to room temperature, a solution of compound 109 (250 mg, 0.58 mmol) in anhydrous dimethylsulfoxide (4 mL) was added. The mixture was then heated at 140° C., under argon, for 7 h. After cooling to room temperature, water (5 mL) was added. The aqueous layer was extracted with dichloromethane (4×20 mL). The organic layers were combined, dried on magnesium sulphate, filtered and evaporated under vacuum. The residue was chromatographed (Al$_2$O$_3$, AcOEt/cyclohexane, 9/1, v/v) to give compound 110 (100 mg, 0.24 mmol) as a yellow solid. Yield 42%; $R_f$ (Al$_2$O$_3$, AcOEt/cyclohexane, 9/1, v/v) 0.76; mp 75-77° C. (dec.); IR (KBr) ν 1353, 1554, 1593, 1641, 2800-3000, 3248 cm$^{-1}$; $^1$H NMR (200 MHz, CDCl$_3$) δ 1.06 (t, 6H, J=7.1 Hz), 2.64 (q, 4H, J=7.1 Hz), 2.76 (t, 2H, J=6.0 Hz), 3.61 (q, 2H, J=6.0 Hz), 7.17 (d, 1H, $^3J_{H-F}$=2.6 Hz), 7.25 (m, 1H), 7.65 (d, 1H, J=8.9 Hz), 7.97 (dd, 1H, J=1.9, 8.9 Hz), 8.62 (d, 1H, J=1.9 Hz).

EXAMPLE 25

N-[2-[N-ethyl-N-[2-(2-fluoropyridin-3-yloxy)ethyl]amino]ethyl]-6-(tributylstannyl)quinoxaline-2-carboxamide (111)

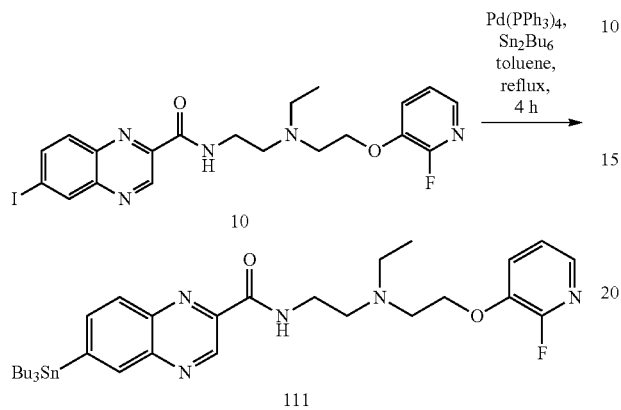

N-[2-[N-ethyl-N-[2-(2-fluoropyridin-3-yloxy)ethyl]amino]ethyl]-6-(tributylstannyl)quinoxaline-2-carboxamide (111)

This compound was prepared, starting from compound 10 (0.40 g, 0.79 mmol), according to the procedure developed for compound 83. Reaction time at reflux: 4 h; the purification was performed using column chromatography (Al$_2$O$_3$, AcOEt/cyclohexane, 6/4, v/v) to give compound III (318 mg, 0.47 mmol) as a red oil. Yield 60%; R$_f$ (Al$_2$O$_3$, AcOEt/cyclohexane, 6/4, v/v) 0.58; IR (CCl$_4$) ν 1120, 1190, 1250, 1283, 1466, 1521, 1682, 2800-3000 cm$^{-1}$; $^1$H NMR (200 MHz, CDCl$_3$) δ 0.86 (t, 9H, J=7.2 Hz), 1.12 (m, 9H), 1.32 (sex, 6H, J=7.2 Hz), 1.57 (m, 6H), 2.71 (q, 2H, J=7.2 Hz), 2.84 (t, 2H, J=6.0 Hz), 2.98 (t, 2H, J=5.6 Hz), 3.61 (q, 2H, J=6.0 Hz), 4.11 (t, 2H, J=5.6 Hz), 6.91 (dd, 1H, J=4.8, 7.7 Hz), 7.20 (m, 1H), 7.59 (td, 1H, $^4$J$_{H-F}$=1.5 Hz, J=1.5, 4.8 Hz), 7.86 (m, 2H), 8.27 (s, 1H, $^3$J119$_{Sn}$/117$_{Sn-H}$=41.0 Hz), 8.46 (te, 1H), 9.61 (s, 1H); ESI-MS m/z 674.3 [M+H]$^+$.

EXAMPLE 26

N-[2-(diethylamino)ethyl]-4-fluoro-6-(tributylstannyl)quinoline-8-carboxamide (112)

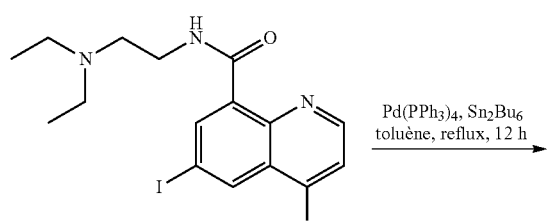

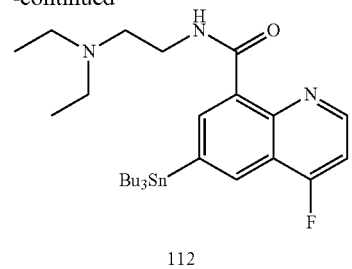

N-[2-(diethylamino)ethyl]-4-fluoro-6-(tributylstannyl)quinoline-8-carboxamide (112)

To a solution of compound 102 (210 mg, 0.51 mmol) in anhydrous toluene (12 mL), beforehand degassed under argon, were successively added, hexabutylditin (399 μL, 0.69 mmol) and freshly prepared tetrakis(triphenylphosphine)palladium(0) (20 mg) (Coulson, D. R.; Satek, L. C.; Grim, S. O. Tetrakis (Triphenylphosphine) Palladium (0) *Inorg. Synth.* 1971, 13, 121-124). The resulting solution was refluxed for 12 h under argon. After cooling to room temperature, the mixture was filtered through Celite®545, washed with toluene (3×10 mL) and the filtrate was evaporated under vacuum. The residue obtained was then chromatographed (Al$_2$O$_3$, cyclohexane/AcOEt, 6/4, v/v) to give compound 112 (182 mg, 0.31 mmol) as a yellow oil. Yield 62%; R$_f$ (Al$_2$O$_3$, cyclohexane/AcOEt, 6/4, v/v) 0.61; IR (CCl$_4$) ν 1564, 1657, 2925, 2961 cm$^{-1}$; $^1$H NMR (200 MHz, CDCl$_3$) δ 0.85 (t, 9H, J=7.2 Hz), 1.06 (t, 6H, J=7.1 Hz), 1.17 (m, 6H), 1.33 (m, 6H), 1.54 (m, 6H), 2.62 (q, 4H, J=7.1 Hz), 2.75 (t, 2H, J=6.5 Hz), 3.66 (q, 2H, J=6.5 Hz), 7.11 (dd, 1H, $^3$J$_{H-F}$=9.5 Hz, J=5.1 Hz), 8.31 (dd, 1H, $^3$J119$_{Sn}$/117$_{Sn-H}$=38.6 Hz, J=0.9 Hz), 8.80 (dd, 1H, $^4$J$_{H-F}$=8.5 Hz, J=5.1 Hz), 8.99 (dd, 1H, $^3$J119$_{Sn}$/117$_{Sn-H}$=32.7 Hz, J=0.9 Hz), 11.24 (m, 1H); ESI-MS m/z 580.2 [M+H]$^+$.

EXAMPLE 27

N-[2-(diethylamino)ethyl]-4-fluoro-6-(tributylstannyl)quinoline-2-carboxamide (113)

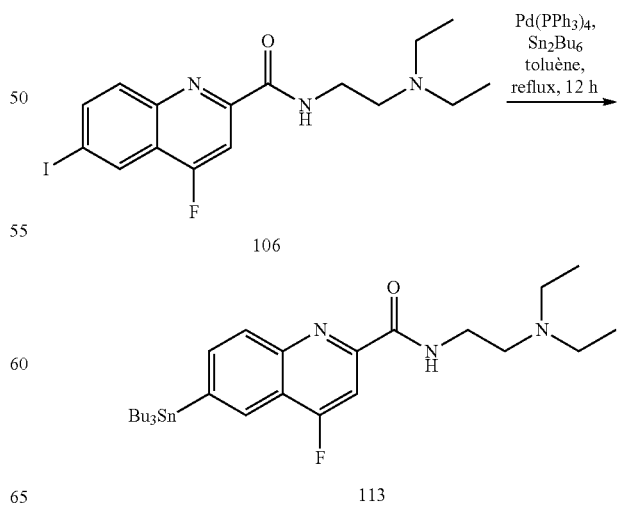

N-[2-(diethylamino)ethyl]-4-fluoro-6-(tributylstannyl)quinoline-2-carboxamide (113)

This compound was prepared, starting from compound 106 (206 mg, 0.50 mmol), according to the procedure developed for compound 112. The purification was performed using column chromatography (Al$_2$O$_3$, cyclohexane/AcOEt, 5/5, v/v) to give compound 113 (165 mg, 0.29 mmol) as an orange oil. Yield 57%; R$_f$ (Al$_2$O$_3$, cyclohexane/AcOEt, 5/5, v/v) 0.73; IR (CCl$_4$) ν 1521, 1684, 2929, 2962 cm$^{-1}$; $^1$H NMR (200 MHz, CDCl$_3$) δ 0.88 (t, 9H, J=7.0 Hz), 1.10 (t, 6H, J=7.1 Hz), 1.17 (m, 6H), 1.33 (m, 6H), 1.55 (m, 6H), 2.64 (q, 4H, J=7.1 Hz), 2.74 (t, 2H, J=6.3 Hz), 3.59 (q, 2H, J=6.3 Hz), 7.88 (d, 1H, J=8.3 Hz), 7.94 (d, 1H, $^3$J$_{H\text{-}F}$=10.4 Hz), 8.04 (dd, 1H, J=1.4, 8.3 Hz), 8.20 (d, 1H, $^3$J119$_{Sn}$/117$_{Sn\text{-}H}$=40.8 Hz), 8.61 (m, 1H); ESI-MS m/z 580.2 [M+H]$^+$.

The chemical structures and physical data of some unlabelled compounds of formulae (Ib) of the invention are illustrated in the following Table I.

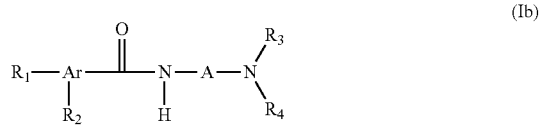

(Ib)

TABLE I

| NC | R$_1$—Ar— / R$_2$ | A | R$_3$ | R$_4$ | Salt | M.p (° C.) |
|---|---|---|---|---|---|---|
| 10 | 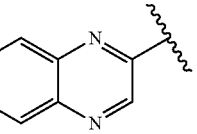 | —CH$_2$—CH$_2$— | Et | 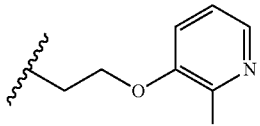 | — | oil |
| 11 | | | | | 2 HCl | 100 |
| 16 | 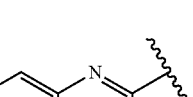 | —CH$_2$—CH$_2$— | Et |  | — | oil |
| 17 | | | | | 2 HCl | 100 |
| 20 | 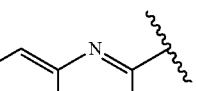 | —CH$_2$—CH$_2$— | Et | 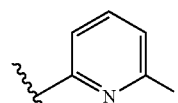 | — | 134 |
| 25 | 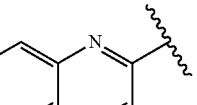 | —CH$_2$—CH$_2$— | Et | 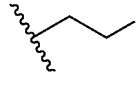 | — | oil |
| 26 | | | | | 2 HCl | 185 |
| 33 | 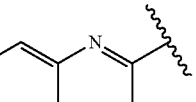 | —CH$_2$—CH$_2$— | Et | 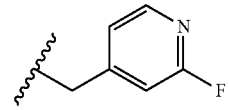 [SMILES: *Cc1ccnc(F)c1] | — | oil |
| 34 | | | | | 2 HCl | 140 |
| 39 | 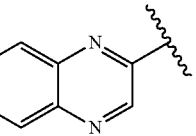 | —CH$_2$—CH$_2$— | Et | 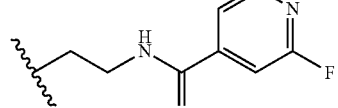 | — | 147 |
| 40 | | | | | 2 HCl | 158 |
| 46 | 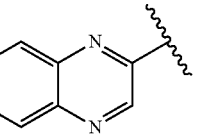 | —CH$_2$—CH$_2$— | Et | 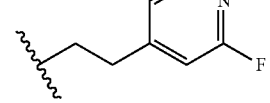 | — | oil |
| 47 | | | | | 2 HCl | 209 |

TABLE I-continued

| NC | R₁—Ar—R₂ | A | R₃ | R₄ | Salt | M.p (° C.) |
|---|---|---|---|---|---|---|
| 52 | 6-iodoquinoxalin-2-yl | —CH₂—CH₂— | Et | | — | 71 |
| 53 | 6-iodoquinoxalin-2-yl | —CH₂—CH₂— | Et | (CH₂)₃-(2-fluoropyridin-4-yl) | 2 HCl | 90 |
| 56 | 6-iodoquinoxalin-2-yl | —CH₂—CH₂— | Et | —CH₂—CH=CH—CH₂F | — | 51 |
| 57 | 6-iodoquinoxalin-2-yl | —CH₂—CH₂— | Et | —CH₂—CH=CH—CH₂F | 2 HCl | 140 |
| 60 | 6-iodoquinoxalin-2-yl | —CH₂—CH₂— | Et | (CH₂)₃-O-(2-nitropyridin-3-yl) | — | oil |
| 63 | 6-iodoquinoxalin-2-yl | —CH₂—CH₂— | Et | (CH₂)₃-NH-(2-bromopyridin-4-yl) | — | 50 |
| 67 | 6-iodoquinolin-2-yl | —CH₂—CH₂— | Et | (CH₂)₃-O-(2-fluoropyridin-3-yl) | — | oil |
| 68 | 6-iodoquinolin-2-yl | —CH₂—CH₂— | Et | (CH₂)₃-O-(2-fluoropyridin-3-yl) | 2 HCl | 100 |
| 70 | 6-iodonaphth-2-yl | —CH₂—CH₂— | Et | (CH₂)₃-O-(2-fluoropyridin-3-yl) | — | oil |
| 71 | 6-iodonaphth-2-yl | —CH₂—CH₂— | Et | (CH₂)₃-O-(2-fluoropyridin-3-yl) | HCl | 158 |
| 73 | 8-methyl-1,6-naphthyridin-2-yl | —CH₂—CH₂— | Et | (CH₂)₃-O-(2-fluoropyridin-3-yl) | — | oil |
| 74 | 8-methyl-1,6-naphthyridin-2-yl | —CH₂—CH₂— | Et | (CH₂)₃-O-(2-fluoropyridin-3-yl) | 2 HCl | 132 |
| 76 | 6-iodoimidazo[1,2-a]pyridin-2-yl | —CH₂—CH₂— | Et | (CH₂)₃-O-(2-fluoropyridin-3-yl) | — | oil |
| 77 | 6-iodoimidazo[1,2-a]pyridin-2-yl | —CH₂—CH₂— | Et | (CH₂)₃-O-(2-fluoropyridin-3-yl) | 2 HCl | 144 |
| 79 | 7-iodo-9-oxo-9,10-dihydroacridin-4-yl | —CH₂—CH₂— | Et | (CH₂)₃-O-(2-fluoropyridin-3-yl) | — | oil |
| 80 | 7-iodo-9-oxo-9,10-dihydroacridin-4-yl | —CH₂—CH₂— | Et | (CH₂)₃-O-(2-fluoropyridin-3-yl) | HCl | 206 |

TABLE I-continued

| NC | R₁—Ar—R₂ | A | $R_3$ | $R_4$ | Salt | M.p (° C.) |
|---|---|---|---|---|---|---|
| 84 | 7-iodo-phenazin-1-yl | —CH₂—CH₂— | Et | 3-(2-fluoropyridin-3-yloxy)propyl | — | oil |
| 85 | 7-iodo-phenazin-1-yl | —CH₂—CH₂— | Et | 3-(2-fluoropyridin-3-yloxy)propyl | 2 HCl | 128 |
| 91 | 6-iodo-quinoxalin-2-yl | 2-fluoropyridine-3,4-diyl-bis(methylene) | Et | Et | — | 148 |
| 92 | 6-iodo-quinoxalin-2-yl | 2-fluoropyridine-3,4-diyl-bis(methylene) | Et | Et | 2 HCl | 198 |
| 96 | 4-fluoro-6-iodo-quinolin-2-yl | —CH₂—CH₂— | Et | Et | — | 89 |
| 102 | 4-fluoro-6-iodo-quinolin-8-yl | —CH₂—CH₂— | Et | Et | — | 80 |
| 106 | 4-fluoro-6-iodo-quinolin-2-yl | —CH₂—CH₂— | Et | Et | — | 59 |
| 110 | 2-fluoro-6-iodo-quinolin-4-yl | —CH₂—CH₂— | Et | Et | — | 76 |

Et denotes an ethyl radical,
M.p denotes the melting point,

Some radiolabelling examples are reported below.

Materials for Radiolabelling with iodine-125 or iodine-131. [$^{125}$I]NaI (3.7 GBq/mL, 643.8 MBq/mg) was purchased from PerkinElmer Life and Analytical Sciences (331 Treble Cove Road, Billerica, Mass. 01862, US) as a no-carrier-added solution in reductant free $1.0e^{-5}$ M aqueous sodium hydroxide solution (pH 8-11). [$^{131}$I]NaI (66.21 GBq/mL, 712.82 GBq/mg) was purchased from PerkinElmer Life and Analytical Sciences (331 Treble Cove Road, Billerica, Mass. 01862, US) as a 0.1 M sodium hydroxide solution (pH 12-14). Extrelut® and citrate buffer solution (pH=4) were purchased from Merck (Darmstadt, Germany). The radio TLC strips (Merck neutral aluminium oxide 60F$_{254}$ plates) were developed with (CH₂Cl₂/EtOH, 97/3, v/v) or (AcOEt/cyclohexane, 6/4, v/v)

and measured on an AMBIS 400 (Scanalytics, CSPI, San Diego, Calif., USA). Analytical HPLC measurements were performed on a system consisting of a HP1100 (Hewlett Packard, Les Ulis, France) and a Flow one $A_{500}$ Radiomatic detector (Packard, Canberra, Australia). The separation was carried out on a $C_{18}$ column (Purospher $RP_{18}$ e, 5 µm) using the following conditions: gradient time=10 min, flow rate=0.5 mL/min, $H_2O/MeOH/(30:70\rightarrow 0:100)$ ($NH_4OH$ 0.2%), λ=254 nm. HPLC purification was performed on a system including a Shimadzu LC 6A pump, SLC 6B controller, a CR5A integrator, a SPD 6AV UV detector and a flow-trough gamma Raytest Steffi detector. The separation was carried out on a $C_{18}$ column (ZORBAX 80 Å, 4.6×150 mm) using the following conditions: gradient time=20 min, flow rate=1 ml/min, $H_2O/MeOH/(50:50\rightarrow 0:100)$ ($NH_4OH$ 0.2%), λ=254 nm. All radiolabelled compounds were shown by TLC or HPLC to the authentic non-radioactive material and to be free of significant chemical and radiochemical impurities.

Materials for Radiolabelling with Fluorine-18. No-carrier-added fluorine-18 (half-life: 109.8 minutes) was produced via the $[^{18}O(p, n)^{18}F]$ nuclear reaction by irradiation of a 2 mL $[^{18}O]$water target (>97%-enriched, Rotem (CortecNet, Paris, France)) on an IBA Cyclone-18/9 (IBA, Louvain-la-Neuve, Belgium) cyclotron (18 MeV proton beam) and the aqueous radioactive solution was then transferred to the appropriate hot cell. Target hardware: commercial, 2-mL, two-port, stainless steel target holder equipped with a domed-end niobium cylinder insert. Target to hot cell liquid-transfer system: 60 m PTFE line (0.8 mm internal diameter; 1/16 inch external diameter), 2.0 bar helium drive pressure, transfer time 3-6 min. Typical production of $[^{18}F]$fluoride at the end of bombardment for a 20 µA, 30 min (10 µA·h) irradiation: 27.7-29.6 GBq (750-800 mCi). Radio-TLCs were run on pre-coated plates of silica gel $60F_{254}$ (VWR) with a mixture of dichloromethane and methanol as solvents (80/20 to 95/5). Radioactive spots were detected using a Berthold TraceMaster 20 automatic TLC linear analyser. Fluorine-18 labelled compounds were HPLC purified using the following equipment and conditions: System: a Waters 600 pump and a Waters 600 Controller, a Shimadzu SPD10-AVP UV-multi-wavelength detector and a miniature ionisation chamber probe; column: semipreparative Symmetry® C-18, Waters (300×7.8 mm); porosity: 7 µm; eluent $H_2O/CH_3CN/TFA$:75/25/0.1 (v/v/v) or $H_2O/CH_3CN$/aqueous 28% $NH_4OH$: 30/70/0.1 or 35/65/0.1 (v/v/v); flow rate: 5 to 7 mL/min; temperature: rt; absorbance detection at λ=254 nm. Chemical and radiochemical purities of all HPLC-purified and formulated compounds for in vivo imaging were determined using analytical HPLC using the following equipment and conditions: System: a Waters Alliance 2690 (or a Waters binary HPLC pump 1525) equipped with a UV spectrophotometer (Photodiode Array Detector, Waters 996) and a Berthold LB509 radioactivity detector; column: analytical Symmetry-M® C-18, Waters (50×4.6 mm); porosity: 5.0 µm; conditions: isocratic elution with solvA/solvB:55/45 (v/v) or 50/50 (v/v) [solvent A: $H_2O$ containing Low-UV PIC® B7 reagent (20 mL for 1000 mL); solvent B: $H_2O/CH_3CN$: 30:70 (v/v) containing Low-UV PIC® B7 reagent (20 mL for 1000 mL)]; flow rate: 2.0 mL/min; temperature: rt; absorbance detection at λ=254 nm.

Radioiodination by Isotopic Exchange (Iodine-125)

EXAMPLE 28

[$^{125}$I]N-[2-[N-ethyl-N-[2-(2-fluoropyridin-3-yloxy)ethyl]amino]ethyl]-6-iodoquinoxaline-2-carboxamide dihydrochloride salt [$^{125}$I]11

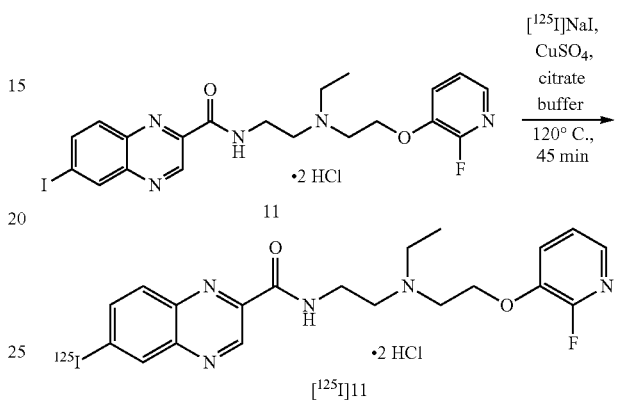

To a solution of compound 11 (2.6 mg, 4.5 µmol) in citrate buffer pH=4 (500 µL) were added, in a closed vial, an aqueous copper sulfate solution (0.5 mg, 100 µL) used as catalyst and [$^{125}$I]NaI (70 µL, 187 MBq). The reaction mixture was heated at 120° C. for 45 min. After cooling to room temperature, the residue was taken up in water (500 µL) and a 1.0 N aqueous NaOH solution (100 µL) was added. The vial cap and septum were removed. The resulting suspension was passed through an Extrelut® column and eluted, after 10 min, with dichloromethane (5<3 mL). The collected organic extracts were evaporated under reduced pressure, taken up with methanol (200 µL), and purified by HPLC at a flow rate of 1 mL/min (retention time: 16.5 min). The fractions containing the product were collected, evaporated to dryness, redissolved in dichloromethane (2 mL) and treated with a 2.0 N hydrochloric acid solution in anhydrous ether (5 mL). The resulting hydrochloride solution was evaporated under reduce pressure, and the dry residue was suspended in anhydrous ether (5 mL). The solvent was then evaporated under vacuum for 30 min to give compound [$^{125}$I]11 (1.8 mg, 3.09 µmol). Radiochemical yield: 53%; specific activity: 32 MBq/µmol; radiochemical purity: 99.7%.

EXAMPLE 29

[$^{125}$I]N-[2-[N-ethyl-N-[2-[(6-fluoropyridin-2-yl)amino]ethyl]amino]ethyl]-6-iodoquinoxaline-2-carboxamide dihydrochloride salt

[$^{125}$I]17

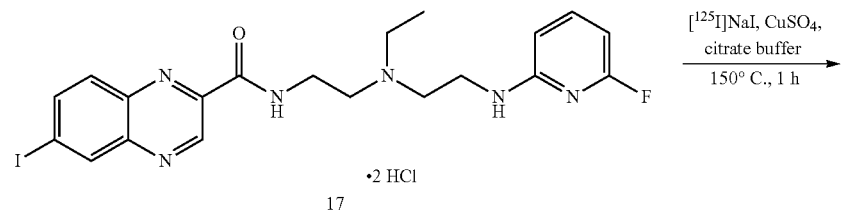

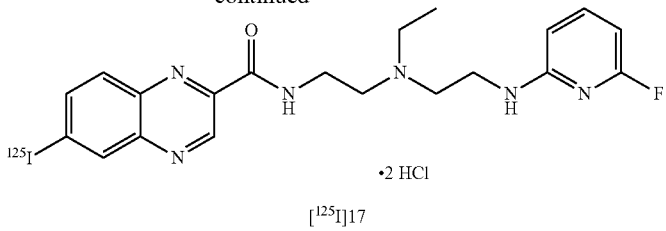

[125I]17

To a solution of compound 17 (2.6 mg, 4.5 μmol) in citrate buffer pH=4 (500 μL) were added, in a closed vial, an aqueous copper sulfate solution (0.5 mg, 100 μL) used as catalyst and [125I]NaI (26 μL, 62 MBq). The reaction mixture was heated at 150° C. for 1 h. After cooling to room temperature, the residue was taken up in water (500 μL) and a 1.0 N aqueous NaOH solution (100 μL) was added. The vial cap and septum were removed. The resulting suspension was passed through an Extrelut® column and eluted, after 10 min, with dichloromethane (5×3 mL). The collected organic extracts were evaporated under reduced pressure, redissolved in dichloromethane (2 mL) and treated with a 2.0 N hydrochloric acid solution in anhydrous ether (5 mL). The resulting hydrochloride solution was evaporated under reduced pressure, and the dry residue was suspended in anhydrous ether (5 mL). The solvent was then evaporated under vacuum for 30 min to give compound [125I]17 (1.6 mg, 2.75 μmol). Radiochemical yield: 66%; specific activity: 15 MBq/μmol; radiochemical purity: 98.8%.

EXAMPLE 30

[125I]N-[2-[[N-ethyl-N-(6-fluoropyridin-2-yl)]amino]ethyl]-6-iodoquinoxaline-2-carboxamide [125I]20

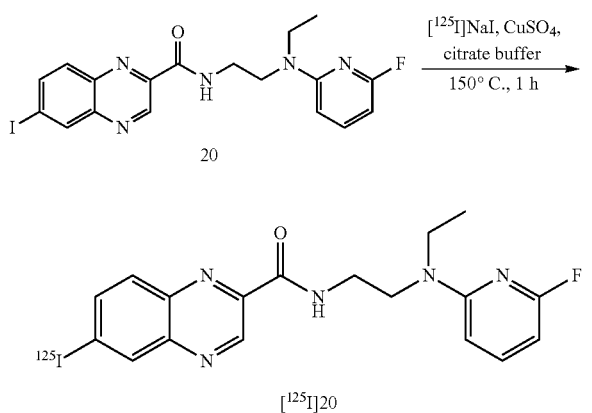

This compound was prepared, starting from compound 20 (1.0 mg, 2.1 μmol) and [125I]NaI (32 μL, 78 MBq), according to the procedure developed for compound [125I]17 except for the final chlorhydrate conversion step to give compound [125I]20 (1.0 mg, 2.15 μmol). Radiochemical yield: 81%; specific activity: 29 MBq/mol; radiochemical purity: 99.8%.

EXAMPLE 31

[125I]N-[2-[[N-ethyl-N-(2-fluoroethyl)]amino]ethyl]-6-iodoquinoxaline-2-carboxamide dihydrochloride salt [125I]26

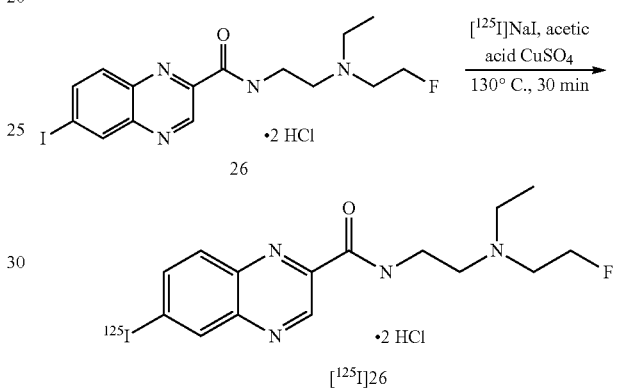

To a solution of compound 26 (3.0 mg, 6.1 mol) in acetic acid (600 μL) were added, in a closed vial, a copper sulfate solution in acetic acid (150 μL, 1 mg·mL⁻¹) used as catalyst and [125I]NaI (50 μL, 119 MBq). The reaction mixture was heated at 130° C. for 30 min. After cooling to room temperature, the residue was taken up in water (500 μL) and a 1.0 N aqueous NaOH solution (100 μL) was added. The vial cap and septum were removed. The resulting suspension was passed through an Extrelut® column and eluted, after 10 min, with dichloromethane (5×3 mL). The collected organic extracts were evaporated under reduced pressure, taken up with methanol (200 μL), and purified by HPLC at a flow rate of 1 ml/min (retention time: 10.9 min). The fractions containing the product were collected, evaporated to dryness, redissolved in dichloromethane (2 mL) and treated with a 2.0 N hydrochloric acid solution in anhydrous ether (5 mL). The resulting hydrochloride solution was evaporated under reduce pressure, and the dry residue was suspended in anhydrous ether (5 mL). The solvent was then evaporated under vacuum for 30 min to give compound [125I]26 (2.1 mg, 4.29 μmol). Radiochemical yield: 33%; specific activity 9 MBq/μmol; radiochemical purity: 97.2%.

EXAMPLES 32 to 40

Other radioiodinated compounds were prepared, starting from the following "initial compound", according to the procedure developed for compound [125I]11 to give the final iodinated tracers.

The experimental conditions and characterization of final compounds are summarized in Table II below.

TABLE II

| Ex | Initial compound | Final compound | Reaction Temp. (° C.) | Reaction time (min) | Retention time (min) | Radiochemical Yield (%) | Specific activity (MBq/µmol) | Radiochemical purity (%) |
|----|---|---|---|---|---|---|---|---|
| 32 | 34 | [$^{125}$I]34 | 130 | 20 | 11.6 | 26 | 7 | 99.9 |
| 33 | 40 | [$^{125}$I]40 | 130 | 27 | 10.6 | 45 | 16 | 98.3 |
| 34 | 47 | [$^{125}$I]47 | 130 | 60 | 13.4 | 33 | 30 | 99.6 |
| 35 | 53 | [$^{125}$I]53 | 130 | 45 | 14.4 | 34 | 24 | 94.2 |
| 36 | 57 | [$^{125}$I]57 | 130 | 30 | 14.2 | 34 | 23 | 98.3 |
| 37 | 71 | [$^{125}$I]71 | 130 | 60 | 11.4 | 41 | 21 | 99.9 |
| 38 | 74 | [$^{125}$I]74 | 130 | 45 | 11.9 | 22 | 15 | 99.9 |
| 39 | 85 | [$^{125}$I]85 | 130 | 45 | 15.7 | 41 | 42 | 99.0 |
| 40 | 92 | [$^{125}$I]92 | 130 | 45 | 15.4 | 30 | 48 | 98.5 |

Radioiodo-destannylation (Iodine-125)

EXAMPLE 41

[$^{125}$I]N-[2-(diethylamino)ethyl]-4-fluoro-6-iodoquinoline-8-carboxamide [$^{125}$I]102

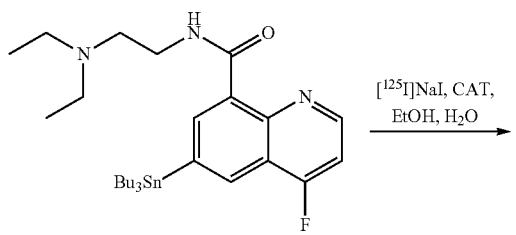

In a closed vial containing compound 112 (0.50 mg, 0.86 mol) in EtOH (100 µL) were added, in the following order: a citrate buffer solution pH=4 (25 µL), [$^{125}$I]NaI (90 µL, 218 MBq) and an aqueous solution of chloramine T monohydrate (100 µL, 0.5 mg·mL$^{-1}$). The resulting solution was vortexed at room temperature for 45 min. The reaction was quenched with an aqueous 1 N sodium hydroxide solution (200 µL). The mixture was vortexed for 5 min and the vial cap and septum were removed. The reaction mixture was transferred to an Extrelut® column and the vial was rinsed with a solution of H$_2$O/EtOH (1/1, v/v, 2×100 µL). After 10 min, the column was eluted with dichloromethane (5×2 mL). The organic extracts were collected and evaporated under reduced pressure. The residue was taken up with methanol (200 µL), and purified by HPLC at a flow rate of 1 mL/min (retention time: 12.7 min). The fractions containing the product were collected and evaporated to dryness to yield the expected compound [$^{125}$I]102 (108 MBq). Radiochemical yield: 49%; specific activity: 96.5 GBq/µmol; radiochemical purity: 99.9%.

EXAMPLE 42

[$^{125}$I]N-[2-(diethylamino)ethyl]-4-fluoro-6-iodoquinoline-2-carboxamide[$^{125}$I]106

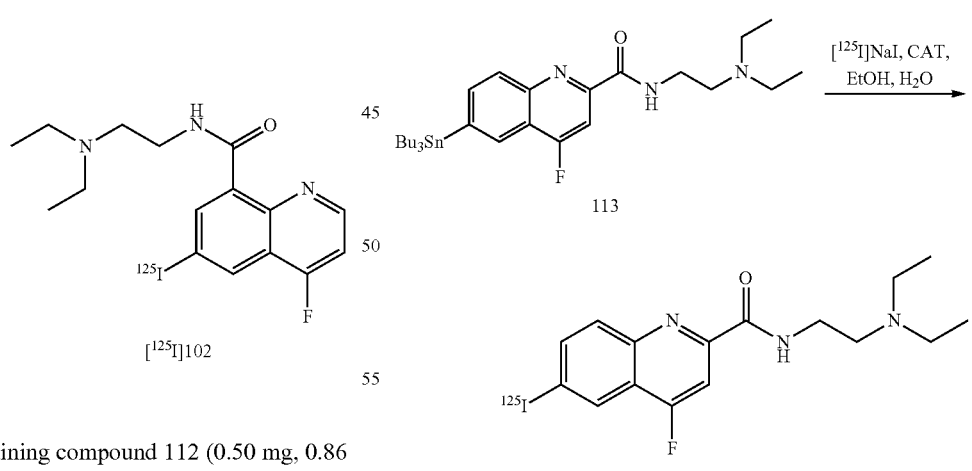

This compound was prepared, starting from compound 113 (0.5 mg, 0.86 µmol) and [$^{125}$I]NaI (60 µL, 149 MBq), according to the procedure developed for compound [$^{125}$I]102. Reaction time at room temperature: 45 min to give [$^{125}$I]106 (55 MBq); retention time: 13.4 min; radiochemical yield: 37%; specific activity: 96.5 GBq/mol; radiochemical purity: 98.3%.

Radioiodo-destannylation (Iodine-131)

EXAMPLE 43

[$^{131}$I]N-[2-[N-ethyl-N-[2-(2-fluoropyridin-3-yloxy)ethyl]amino]ethyl]-6-iodoquinoxaline-2-carboxamide dihydrochloride salt [$^{131}$I]11

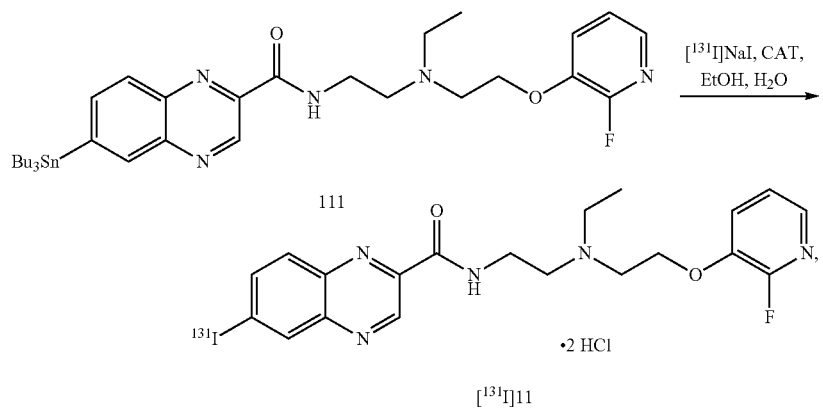

In a closed vial containing compound III (0.52 mg, 0.77 µmol) in ethanol (500 µL) were added, in the following order: a citrate buffer solution pH=4 (150 µL), [$^{131}$I]NaI (117 µL, 2.42 GBq) and an aqueous solution of chloramine T monohydrate (400 µL, 0.5 mg·mL$^{-1}$). The resulting solution was vortexed at room temperature for 30 min. The reaction was quenched successively with an aqueous sodium metabisulfite solution (400 µL, 0.2 g·mL$^{-1}$) and an aqueous 3 N sodium hydroxide solution (500 µL). The mixture was vortexed for 5 min and the vial cap and septum were removed. The reaction mixture was transferred to an Extrelut® column and the vial was rinsed with a solution of H$_2$O/EtOH (1/1, v/v, 2×100 µL). After 10 min, the column was eluted with dichloromethane (5×2 mL). The organic extracts were collected, evaporated under reduced pressure, taken up with methanol (200 µL), and purified by HPLC at a flow rate of 1 mL/min (retention time: 18.0 min). The fractions containing the product were collected, evaporated to dryness, redissolved in dichloromethane (2 mL) and treated with a 2.0 N hydrochloric acid solution in anhydrous ether (5 mL). The resulting hydrochloride solution was evaporated under reduce pressure, and the dry residue was suspended in anhydrous ether (5 mL). The solvent was then evaporated under vacuum for 30 min to yield the expected compound [$^{131}$I]11 (1.14 GBq). Radiochemical yield: 47%, 106.9 GBq/µmol; radiochemical purity: 98.5%.

Radiofluorination (Fluorine-18)

EXAMPLE 44

[$^{18}$F]N-[2-[N-ethyl-N-[2-(2-fluoropyridin-3-yloxy)ethyl]amino]ethyl]-6-iodoquinoxaline-2-carboxamide [$^{18}$F]10

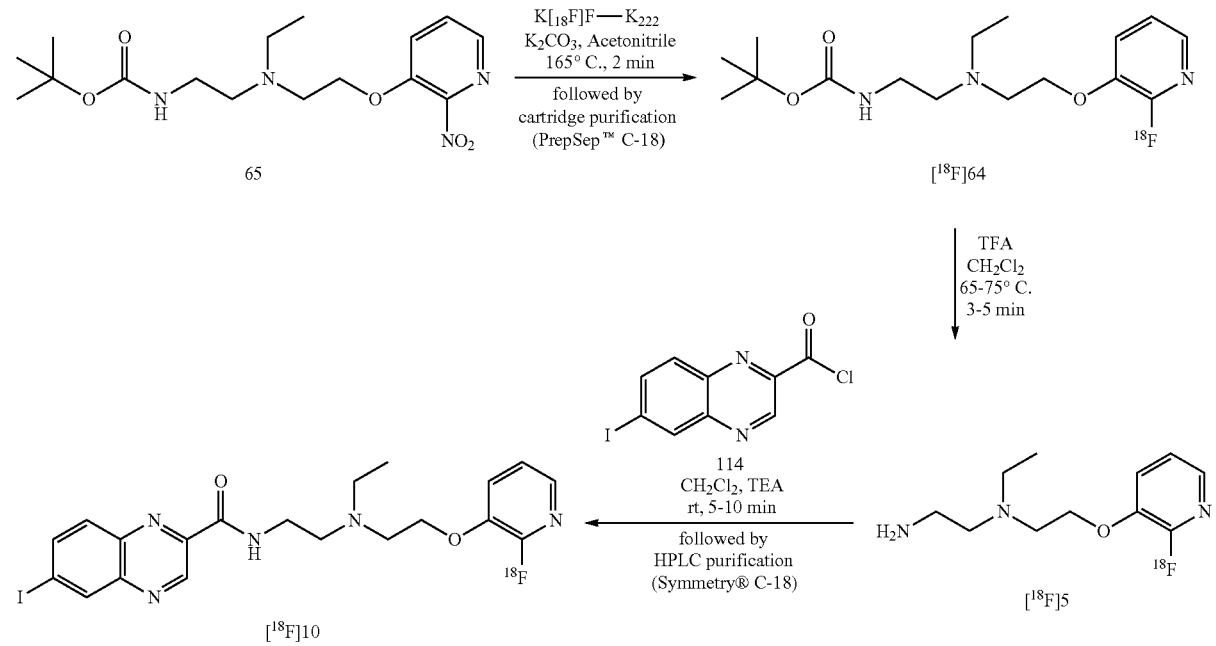

Compound [$^{18}$F]10 was prepared using procedures such as those described in the section "Radiofluorination strategies—typical example 6".

Prerequisite: Preparation of the K[$^{18}$F]F-K$_{222}$-complex. No-carrier-added cyclotron-produced fluorine-18 was isolated as [$^{18}$F]fluoride ion by passing the irradiated [$^{18}$O]water target, using helium pressure (1.5-2.0 bar), through an anion exchange resin (SepPak®Light Waters Accell™ Plus QMA cartridge, chloride form, beforehand washed with 1 M aqueous sodium hydrogencarbonate (2 mL) and rinsed with water (20 mL) and acetonitrile (10 mL)). Helium was blown through the column to maximally extract [$^{18}$O]water. The [$^{18}$F]fluoride ion was then eluted from the resin, using an aqueous potassium carbonate solution (1.0 mL of a 4.5 mg/mL (or 1.0 mg/mL) solution), into a Vacutainer® tube containing Kryptofix®222 (12.0 to 15.0 mg). The resulting solution was then gently concentrated to dryness at 145-150° C. under a nitrogen stream for 10 min to give no-carrier-added K[$^{18}$F]F-K$_{222}$ complex as a white semi-solid residue.

Fluorine-18 Incorporation, N-Boc Removal, Subsequent Acylation Reaction, and HPLC Purification. Acetonitrile (800 μL) containing precursor 65 (3.0 to 4.0 mg, 8.5-11.3 μmol) was added into the Vacutainer® tube containing the dried K[$^{18}$F]F-K$_{222}$ complex. The tube (open) was thoroughly vortexed (30 s) and then placed in a heating block (at 165° C., for 2 min) without stirring the contents. The reaction vessel was then cooled using an ice-water bath, the remaining radioactivity was measured. The residue was taken up with dimethylsulfoxide (1 mL). The resulting mixture was then diluted with water (1 mL) and transferred onto a C$_{18}$ cartridge (PrepSep™ R-C18 Extraction Column, Fisher Scientific, activated beforehand with ethanol (2 mL) and then rinsed with water (10 mL)), pre-filled with water (2 mL). The tube was rinsed twice with water (1 mL), which was also transferred and added to the diluted reaction mixture on top of the cartridge. An additional portion of water (2 mL) was further added to the diluted reaction mixture on top of the cartridge. The whole was then passed through the cartridge, which was then washed with water (3 mL) and partially dried for 0.5 min by applying a nitrogen stream. The intermediate tert-butyl N-[2-[N-ethyl-N-[2-(2-[$^{18}$F]fluoropyridin-3-yloxy)ethyl]amino]ethyl]carbamate ([$^{18}$F]64) was eluted from the cartridge with dichloromethane (3 mL) into a 5 mL reaction vial containing trifluoroacetic acid (TFA, 0.1 mL). Twice 1 mL of dichloromethane was used to wash the cartridge and to completely transfer [$^{18}$F]64. The resulting dichloromethane/TFA solution (50/1, v/v) was concentrated to dryness (at 65-75° C. under a gentle nitrogen stream for 4-6 min) giving the desired N-(2-aminoethyl)-N-ethyl-N-[2-(2-[$^{18}$F]fluoropyridin-3-yloxy)ethyl]amine ([$^{18}$F]5). This residue was first redissolved in dichloromethane (2 mL) and concentrated again to dryness to minimize trifluoroacetic acid presence (at 65-75° C. under a gentle nitrogen stream for another 2-3 min), then redissolved in a mixture of triethylamine and dichloromethane (1/1, v/v, 400 μL). After addition of 200 μL of a solution of 6-iodoquinoxaline-2-carbonylchloride (114) (Denoyer, D.; Labarre, P.; Papon, J.; Miot-Noirault, E.; Galmier, M. J.; Madelmont, J. C.; Chezal, J. M.; Moins, N. Development of a high-performance liquid chromatographic method for the determination of a new potent radioiodinated melanoma imaging and therapeutic agent. *Journal of Chromatography B*, 2008, 875, 411-418) in dichloromethane (20 mg/mL or 12.5 mol), the reaction mixture was allowed to react for 5 to 10 min at room temperature. The reaction mixture was then concentrated to dryness at 65-75° C. under a gentle nitrogen stream for 3-5 min. Finally, the residue was redissolved in a mixture of H$_2$O and acetonitrile (1/1, v/v, 1 mL) and the crude was injected onto HPLC. Isocratic elution, performed using H$_2$O/CH$_3$CN/TFA:75/25/0.1 (v/v/v) as eluent, gave pure labelled N-[2-[N-ethyl-N-[2-(2-[$^{18}$F]fluoropyridin-3-yloxy)ethyl]amino]ethyl]-6-iodoquinoxaline-2-carboxamide ([$^{18}$F]10), t$_R$: 9.0-10.0 min.

Formulation. Formulation of the labelled product [$^{18}$F]10 for i. v. injection was effected as follows: The HPLC-collected fraction containing the radiotracer was diluted with water (30 mL). The resulting solution was passed through a SepPak®Plus C18 cartridge (Waters, washed with 2 mL of ethanol and then rinsed with 10 mL of water prior to use). The cartridge was washed with water (10 mL) and partially dried by applying a nitrogen stream for 10 s. The radiotracer [$^{18}$F]10 was eluted with 2 mL of ethanol followed by 8 mL of physiological saline. Finally, physiological saline was added to take the ethanol concentration below 10%. This whole process was performed using a remote-controlled dedicated home-made device based on a literature procedure.

Quality Control. Chemical and radiochemical purities were assessed on an aliquot of the preparation by TLC and HPLC, with a sample of authentic compound 10 (HPLC: solvA/solvB:55/45 (v/v), t$_R$: 2.10 min—TLC (dichloromethane/Methanol: 95/5): R$_f$: 0.3).

EXAMPLE 45

[$^{18}$F]N-[2-(diethylamino)ethyl]-4-fluoro-6-iodoquinoline-2-carboxamide [$^{18}$F]106

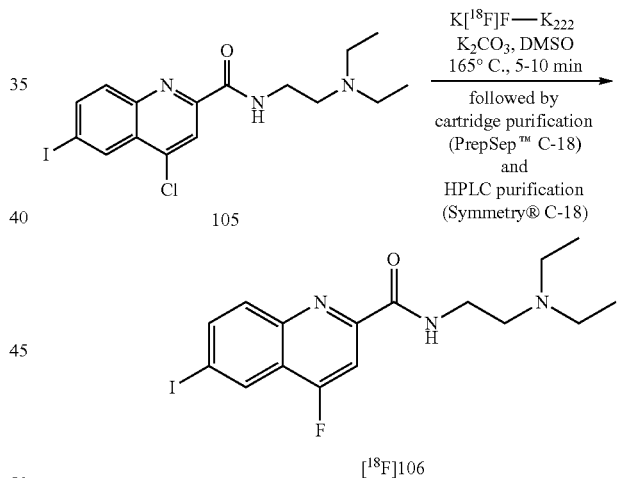

Compound [$^{18}$F]106 was prepared using procedures such as those described in the section "Radiofluorination strategies—typical example 4".

Prerequisite: The K[$^{18}$F]F-K$_{222}$-complex was prepared as described in example 44.

Fluorine-18 Incorporation and HPLC Purification. DMSO (600 μL) containing precursor 105 (5.0 mg, 11.5 μmol) was added into the Vacutainer® tube containing the dried K[$^{18}$F]F-K$_{222}$ complex. The tube (open) was thoroughly vortexed (30 s) and then placed in a heating block (at 165° C., for 5 to 10 min) without stirring the contents. The reaction vessel was then cooled using an ice-water bath, the remaining radioactivity was measured. The reaction mixture was then diluted with water (1 mL) and transferred onto a C$_{18}$ cartridge (PrepSep™ R-C$_{18}$ Extraction Column, Fisher Scientific, activated beforehand with ethanol (2 mL) and then rinsed with water (10 mL)), pre-filled with water (2 mL). The tube was rinsed twice with water (1 mL), which was also transferred and added to the diluted reaction mixture on top of the cartridge. An additional portion of water (2 mL) was further added to the diluted reaction mixture on top of the cartridge. The whole was then passed through the cartridge, which was then washed with water (3 mL) and partially dried for 0.5 min by applying a nitrogen stream. [$^{18}$F]106 was eluted from the cartridge with dichloromethane (3 mL) into an empty 5 mL reaction vial. Elution was repeated twice with 1 mL of dichloromethane for maximal transfer of [$^{18}$F]106. The incorporation yield was estimated after the C18 cartridge elution by the dichloromethane over total eluted radioactivity (DMSO/H$_2$O+dichloromethane) ratio. The dichloromethane solution was then concentrated to dryness at 65-75° C. under a gentle nitrogen stream for 3-5 min. Finally, the residue was redissolved in the HPLC solvent used for purification (1.0 mL) and the solution was injected onto HPLC. Isocratic elution, performed using H$_2$O/CH$_3$CN/aqueous 28% NH$_4$OH: 30/70/0.1 or 35/65/0.1 (v/v/v) as eluent, gave pure labelled [$^{18}$F]106, t$_R$: 10.5-11.5 min.

Formulation. Formulation of the labelled product [$^{18}$F]106 for i.v. injection was effected as follows as described in example 44 for the labelled product [$^{18}$F]10. Alternatively, formulation of the labelled product for i.v. injection was also effected as follows: The HPLC-collected fraction containing the radiotracer was diluted with water (30 mL). The resulting solution was passed through a Chromafix® PS-RP cartridge (Macherey-Nagel, washed with 2 mL of ethanol and then rinsed with 10 mL of water prior to use). The cartridge was washed with water (10 mL) and partially dried by applying a nitrogen stream for 10 s. The radiotracer was eluted with 2 mL of ethanol containing 1% of acetic acid followed by 8 mL of physiological saline. Finally, physiological saline was added to take the ethanol concentration below 10%. This whole process was performed using a remote-controlled dedicated home-made device based on a literature procedure.

Quality Control. Chemical and radiochemical purities were assessed on an aliquot of the preparation by TLC and HPLC, with a sample of authentic compound 106 (HPLC: solvA/solvB: 50/50 (v/v), t$_R$: 1.75 min—TLC (80/20): R$_f$: 0.38).

Some of the compounds of the invention have been subject of pharmacological tests reported below.

Pharmacology Experimentation

Cell Culture. The transplantable B16F0 melanoma cells originating from C57BL/6J mice were obtained from ATCC (Manassas, USA). The melanocytes were grown as monolayers in culture flasks in Eagle's MEM-glutaMAX medium (Invitrogen, Cergy Pontoise, France) supplemented with 10% FCS (Biowest, Nuaillé, France), 1% vitamins, 1 mM non essential amino acids, 1 mM sodium pyruvate and 4 µg/µL gentamycin (Invitrogen). The cells were grown at 37° C. in a humidified incubator containing 5% CO$_2$.

Animals. All experiments were carried out in accordance with the institution recommendations based on the guide for the care and use of laboratory animals. For therapy experiment, we used 6- to 8-week-old C57BL/6J male mice (Charles River Laboratories).

Tumour Implantation. For transplantation, cells grown in monolayer culture to confluence were trypsinized and washed with phosphate buffer saline (PBS). They were resuspended in PBS and each mouse received 0.1 mL subcutaneously (3×10$^5$ cells) on the left flank in order to allow a tumour growth on the body side. Ten days later, the tumours became palpable with a percentage of tumour take of 98-100%.

Biodistribution Study by Scintigraphic Imaging:

The in vivo biodistribution and kinetic profile of each radiolabelled (iodine-125) compound have been studied in C57BL6 male mice bearing the B16 F0 murine melanoma by repeated planar scintigraphic imaging which allows the tumour uptake follow-up in the same animal.

Gamma Camera. In vivo radionuclide imaging was performed using a γ IMAGER (Biospace Mesures, Paris, France) especially dedicated for small animal, a scintigraphic camera with a continuous 4 mm thick×120 mm diameter CsI(Na) crystal, a position-sensitive Hamamatsu R3292 photomultiplier and a 10 cm field of view.

Imaging Protocol. On day 14 after tumour implantation (tumour weight 0.25±0.10 g) each [$^{125}$I]-radioiodinated compound was administered intravenously via a tail vein (0.1 µmol, range 3.7 to 7 MBq/animal) in three mice for each compound. At different times after administration (1, 3, 6, 24, 72 hours, 5, 7, 10 and 15 days), mice were anesthetized with 0.2 mL, for a 20 g mouse, of a ketamine-xylazine mixture in saline (1-0.25 mL for 5 mL) by i. p. administration, and repeated planar scintigraphic whole body imaging (mouse laying in anterior position on the camera field) were performed by an acquisition time of 10 min. For this study, the camera was equipped with a 1.8/0.2/20 collimator (hole diameter/septum thickness/height in mm).

Tumoural Radioactivity Quantification Approach. The injected activity to each mouse was determined from scintigraphic imaging of the syringe before and after the injection using the γ-IMAGER.

Regions of interest (ROIs) were delineated over the whole body image: whole body uptake area (or the various fixing areas, eyes, thyroid and abdomen) and one for the tumour uptake area. In the various ROIs, the activity (cpm) was quantified using the Biospace measures γ VISION+software. These values were normalized to the injected dose. For the tumour, the activity was also normalized to the tumour weight. Firstly, the volume was calculated from the two dimensions caliper measurement (Bissery, M. C.; Guenard, D.; Gueritte-Voegelin, F.; Lavelle, F. Experimental antitumour activity of taxotere (RP 56976, NSC 628503) a taxol analogue. *Cancer res.* 1991, 51, 4845-4852). Secondly, the weight was determined from the volume value corrected by a factor determined from a large panel of experiments (Weight g=volume mm$^3$×0.6). The data were expressed as % ID/g of B 16F0 melanoma tumour.

This in vivo quantification of the melanoma uptake for a new compound by scintigraphic imaging has been performed after different validation studies:

(i) For the evaluation of system response to activity variations and sensitivity, an in vitro study with the same collimator as for mice has been performed on phantoms consisting of a 10 mm-thick Plexiglas plate with holes of 0.9 cm diameter with half-spherical shaped bottoms. The holes have been filled with a iodine-125 solution of defined activity (7 activities ranging from 37 kBq to 3.7 MBq, with a 2 dilution factor, 4 samples per activity and 3 acquisitions per sample). For quantitative analysis of scintigraphic images, rectangular regions of interest (ROIs) were placed over hole patterns and the hole activity expressed in counts per minute (cpm). The FIG. 1 in annex shows the correlation between camera quantificatied values and values obtained with the gamma counter with a coefficient of 0.9979.

(ii) A comparison camera quantified in vivo values with values determined using the whole body sectioning conventional autoradiographic method has been done for several compounds. The correlation coefficient obtained between the two methods was 0.92.

(iii) For the compound N-(2-diethylaminoethyl)-6-iodoquinoxaline-2-carboxamide, which is described in PCT application n°PCT/IB2007/052992 as compound n°45 in table I of said patent application (hereinafter called "ICF01012"), the tumour uptake has been quantified by 3 methods: camera imaging, autoradiography and counting of tumour tissue after dissection (gamma counter), values are summarized below.

|  |  | 1 H | 3 H | 6 H | 24 H | 72 H |
|---|---|---|---|---|---|---|
| [$^{125}$I]ICF01012 | camera | 21.8 ± 6.6 | 26.2 ± 6.6 | 29.6 ± 8.4 | 28.0 ± 8.1 | 12.3 ± 3.7 |
|  | autoradiography | 17 ± 11.1 | 27.7 ± 7.0 | 36.4 ± 7.6 | 21.7 ± 10.8 | 12.5 ± 1.6 |
|  | tissue counting | 14.9 ± 5.7 | 28.1 ± 8.9 | 29.9 ± 2.8 | 29.7 ± 3.1 | 11.4 ± 2.6 |

Radioactive concentration values in tumour expressed as % injected dose per gram of tissue (% ID/g).

This method, comparatively to the conventional autoradiographic method on animal slices very time consuming (three weeks for the study of one molecule), allows rapidly a selection of molecules on the basis of the tumour uptake.

Results. The tumoural uptake kinetics of the various radioiodinated compounds were summarized in Table II.

Radionuclide Therapy Experiment

[$^{131}$I]11 treatment was administered intravenously at days 6 and 10 after tumour implantation (2×18.5 MBq) in groups of 10 mice. In the same conditions untreated-animals were studied. From three days before the treatment and along the experiment, lugol's iodine solution was added in the two mice groups alimentation to block iodine thyroid uptake. To monitor tumoral growth, tumor volume in mm$^3$ was calculated twice a week from the measurement of two perpendicular diameters using a caliper according to the formula L×S$^2$/2 where L and S are the largest and smallest diameters in mm respectively. At day 19 of the experiment, mice were sacrificed. Tumours were removed, dissected and weighted.

TABLE III

Tumoural uptake kinetics in melanoma bearing mice at various times post injection (radioactive concentration values in tumour expressed as % injected dose per gram of tissue (% ID/g)).

|  | [$^{125}$I]ICF01012 | [$^{125}$I]11 | [$^{125}$I]17 | [$^{125}$I]26 | [$^{125}$I]34 | [$^{125}$I]40 |
|---|---|---|---|---|---|---|
| 1 H | 21.8 ± 6.6 | 12.7 ± 2.3 | 13.1 ± 6.8 | 21.4 ± 4.9 | 10.3 ± 6.6 | 9.6 ± 0.7 |
| 3 H | 26.3 ± 6.6 | 20.2 ± 4.2 | 13.7 ± 6.1 | 22.5 ± 3.6 | 12.0 ± 4.8 | 8.8 ± 1.6 |
| 6 H | 29.6 ± 8.4 | 18.8 ± 1.6 | 12.5 ± 3.9 | 25.0 ± 8.0 | 15.4 ± 6.7 | 12.1 ± 3.2 |
| 24 H | 28.0 ± 8.2 | 18.2 ± 0.6 | 8.6 ± 0.9 | 24.8 ± 6.5 | 16.0 ± 7.4 | 12.1 ± 4.6 |
| 72 H | 12.3 ± 3.7 | 10.3 ± 1.7 | 5.7 ± 1.5 | 20.0 | 10.0 ± 2.6 | 9.6 ± 7.1 |
| 120 H | 7.3 ± 3.6 | 5.2 ± 1.2 | 2.6 ± 0.4 | 8.4 | 7.1 ± 1.8 | 5.1 ± 3.3 |
| 168 H | 3.4 ± 0.3 | 3.2 ± 0.4 | 1.5 ± 0.2 | nd | nd | nd |
| 240 H | 1.9 ± 0.4 | 1.7 ± 0.4 | 0.8 ± 0.1 | 1.6 | 1.9 ± 0.9 | nd |
| 360 H | nd | 0.6 ± 0.3 | 0.4 ± 0.2 | 0.6 | 0.8 ± 0.5 | nd |

|  | [$^{125}$I]47 | [$^{125}$I]53 | [$^{125}$I]57 | [$^{125}$I]74 | [$^{125}$I]85 | [$^{125}$I]92 | [$^{125}$I]106 |
|---|---|---|---|---|---|---|---|
| 1 H | 12.1 ± 4.1 | 9.1 ± 1.8 | 10.8 ± 2.3 | 5.6 ± 1.7 | 11.4 ± 1.7 | 5.6 ± 2.0 | 6.0 ± 1.3 |
| 3 H | 13.3 ± 6.0 | 9.3 ± 0.6 | 12.3 ± 2.8 | 5.5 ± 2.4 | 12.3 ± 1.7 | 6.5 ± 3.2 | 8.0 ± 0.9 |
| 6 H | 14.5 ± 6.6 | 14.1 ± 3.9 | 13.9 ± 1.3 | 5.3 ± 2.4 | 13.8 ± 2.5 | 6.7 ± 1.9 | 9.5 ± 1.8 |
| 24 H | 11.2 ± 2.5 | 16.3 ± 8.9 | 15.0 ± 0.5 | 5.2 ± 2.0 | 13.8 ± 2.3 | 6.4 ± 1.8 | 8.4 ± 0.8 |
| 72 H | 7.7 ± 0.9 | 9.5 ± 5.9 | 10.0 ± 0.9 | 3.3 ± 2.0 | 5.8 ± 0.2 | 4.1 ± 1.5 | 4.9 ± 1.2 |
| 120 H | 5.2 ± 1.7 | 5.1 ± 3.3 | 5.6 ± 1.0 | 1.6 ± 0.7 | 3.7 ± 0.6 | 2.4 ± 0.7 | 3.0 ± 0.1 |
| 168 H | 3.0 ± 1.0 | 2.5 ± 2.1 | 3.3 ± 0.6 | 1.1 ± 0.5 | 2.0 ± 0.9 | 1.5 ± 0.4 | 2.3 ± 0.6 |
| 240 H | 1.6 ± 0.5 | 1.4 ± 1.0 | 1.9 ± 0.3 | 0.5 ± 0.3 | 1.2 ± 0.5 | 0.8 ± 0.3 | 1.5 ± 0.1 |
| 360 H | 1.1 ± 0.3 | 0.7 ± 0.5 | 1.3 ± 0.6 | 0.4 ± 0.3 | 0.7 ± 0.4 | 0.7 ± 0.1 | 0.7 ± 0.1 |

No standard deviation when only one determination per time.
n.d.: non determined.

Most of the compounds exhibited a significant tumoural concentration from 1 h post injection. The higher tumoural concentrations were observed with compounds [$^{125}$I]11 and [$^{125}$I]26 (more than 20% ID/g at 3 h post injection and until 72 h for [$^{125}$I]26). However, many compounds exhibited significant and durable concentrations in melanoma tumor (≥10% DI/g at 72 h post injection for six radioiodinated tracers. After 15 days, the tumoural activity is still quantifiable for all the compounds studied, labelled with iodine-125.

These results show the potentiality of these compounds in medical imaging (SPECT and/or PET), namely for the diagnosis of malignant melonoma. Besides, their specific and durable tumoural uptake should be of particular interest for an application to targeted radionuclide therapy. Compound 11 has been selected for further evaluations in order to validate the multi-modality concept (PET imaging and radionuclide therapy).

Statistical Analyses. In experiment data are given as mean+SEM and were analyzed by the Student or ANOVA tests.

Figure 2:
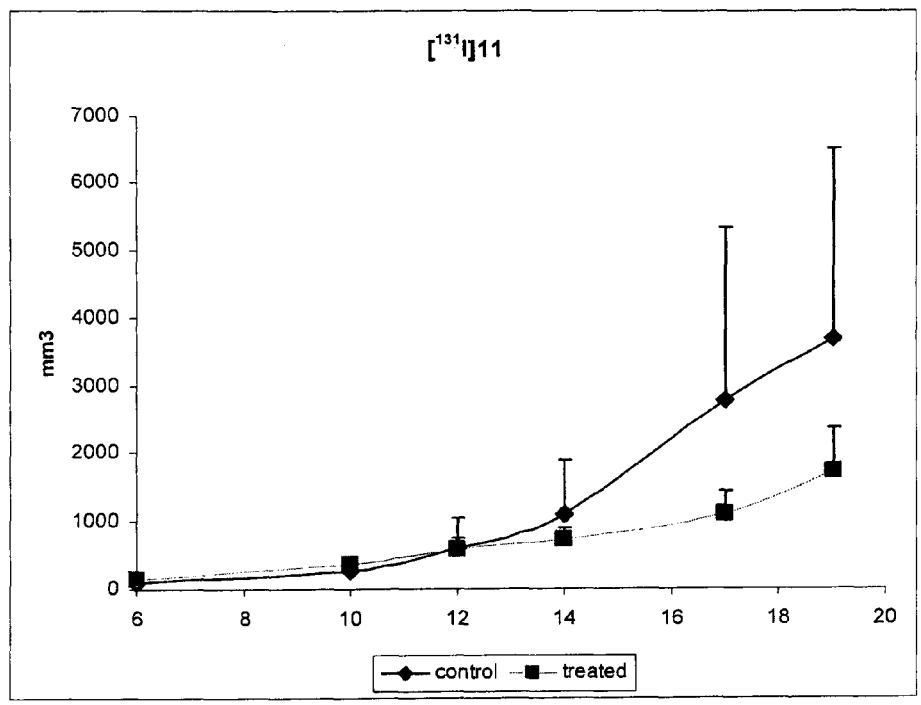
FIG. 2: Effect of [$^{131}$I]11 targeted radionuclide therapy on growth rate of B16F0 murine melanoma tumors in a representative experiment.

Anti-tumoural Efficacy of Targeted Radionuclide Therapy. To assess the therapeutic efficacy of compound [$^{131}$I]11 in C57BL/6J mice bearing subcutaneous B16F0 melanoma cells, we injected twice 18.5 MBq [$^{131}$I]11 into group of 10 mice. Tumour growth expressed as the tumour volume at each time point is shown in FIG. 2 in annex. B16F0 tumours in the untreated group showed exponential growth with 2.82±0.30 days as doubling time. [$^{131}$I]11-treated B16F0 tumours exhibited a growth inhibition phase (GIP) for day 6 to 17 and doubling times were determined as 3.83±0.34. These results showed that [$^{131}$I]11 treatment significantly slowed the B16F0 tumoural growth (p<0.001). The body weight of mice in all groups was stable (data not shown). The weight of tumours at 19 days were 2.29±1.03 g and 0.72±0.28 g respectively for controls and treated. These values differed very significantly, p=0.01 with a ratio T/C=0.31.

All these data confirmed a potential efficacy of [$^{131}$I]11 for targeted radionuclide therapy of melanoma.

PET Imaging

Figure 3:
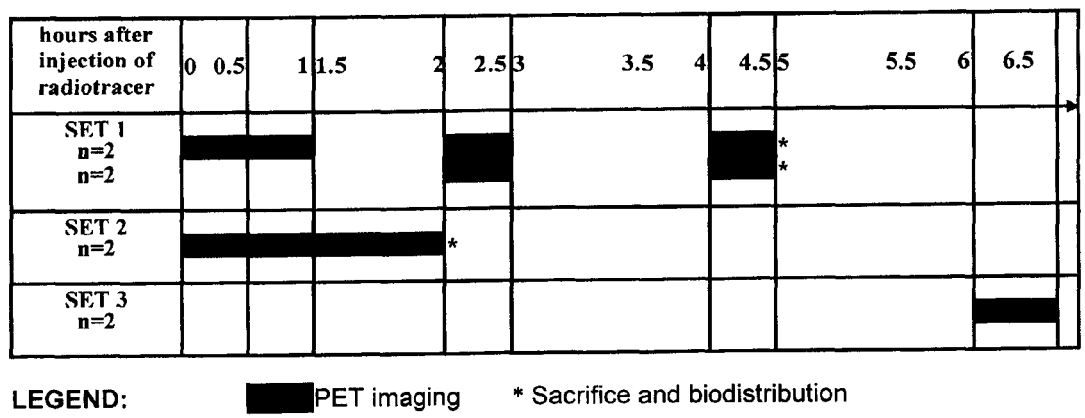
FIG. 3: Time line of PET imaging and biodistribution studies.

Imaging Protocol. Three sets of mice were prepared for PET imaging as described in FIG. 3 in annex:

(Set 1) Four C57BL6 mice bearing both B16F10 and B16F0 murine melanoma tumour grafts on the flanks were anaesthetized with isoflurane and injected with [$^{18}$F]10 (200 μCi). Two were imaged immediately during the first hour after injection, allowed to recover from anaesthesia, anaesthetized again at two hours post injection and imaged between two and two-and-a-half hour after injection, allowed to recover from anaesthesia, anaesthetized again at four hours post injection and imaged between four and four-and-a-half hour after injection, then sacrificed and their organs weighed and counted. Two other mice were allowed to recover from anaesthesia, anaesthetized at two hours post injection and imaged between two and two-and-a-half hour after injection, allowed to recover from anaesthesia, anaesthetized again at four hours post injection and imaged between four and four-and-a-half hour after injection, then sacrificed and their organs weighed and counted.

(Set 2) Two C57BL6 mice bearing both B16F10 and B16F0 murine melanoma tumour grafts on the shoulders (so as to avoid contaminating signals originating from with digestive and urinary tracts) were injected with [$^{18}$F]10 (200 μCi), imaged under isoflurane anesthesia continuously during two hours, then sacrificed and their organs weighed and counted.

(Set 3) One C57BL6 mouse bearing both B16F10 and B16F0 murine melanoma tumour grafts on the shoulders (so as to avoid contaminating signals originating from with digestive and urinary tracts) was injected with [$^{18}$F] 10 (600 μCi), allowed to recover, anaesthetized with isoflurane six hours post injection, imaged during 30 minutes between six and six-and-a-half hours post injection.

Figure 4:
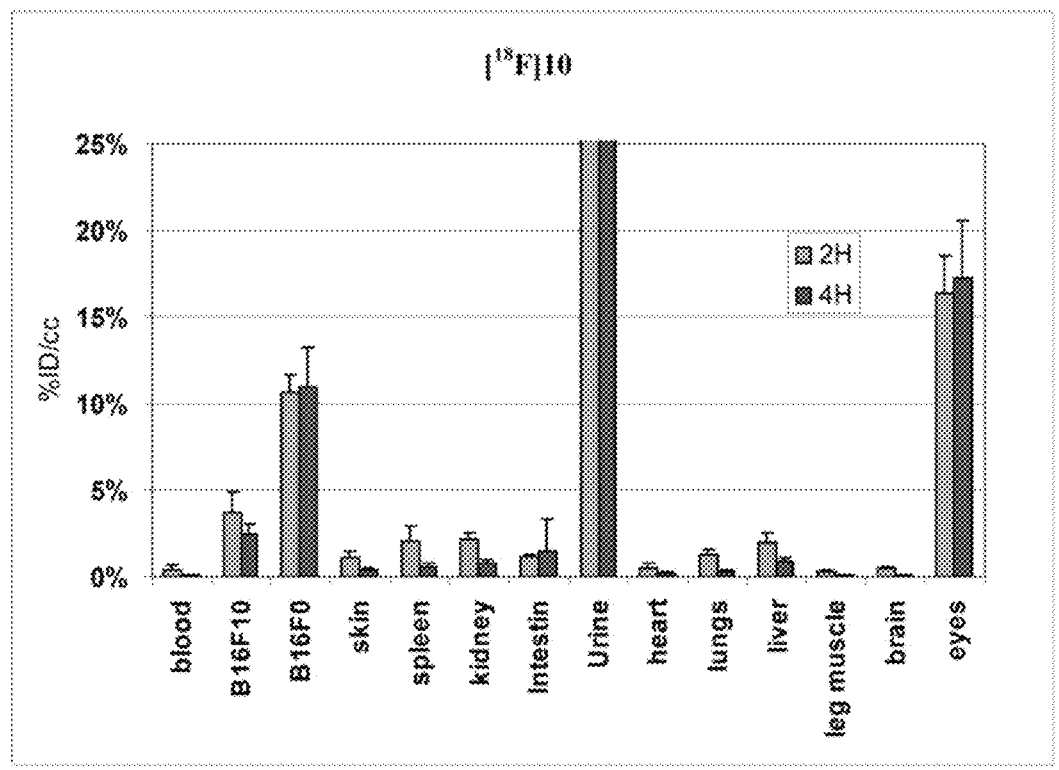
FIG. 4: Concentration of [$^{18}$F]10 in selected organs after i.v. injection in B16F0 melanoma-bearing C57B16 mice from SET 1 and 2.

Biodistribution. [$^{18}$F]10 biodistribution was analysed for the mice of set 1 (n=4) four-and-a-half hours after injection, and for the mice of set 2 (n=2) two-and-a-half hours after injection. Animals were sacrificed by lethal injection of pentobarbital and organs were collected, weighed and radioactivity of each sample was measured on a Cobra gamma counter (Packard). Results are corrected for decay and expressed in percentage of injected dose per cubic centimeter of tissue (% ID/CC) assuming an organ density of one gram per cubic centimetre. Results of [$^{18}$F]10 biodistribution are presented in FIG. 4 in annex and clearly show the capacity of radiotracer [$^{18}$F]10 to specifically target melanoma tumours in vivo.

Figure 5:
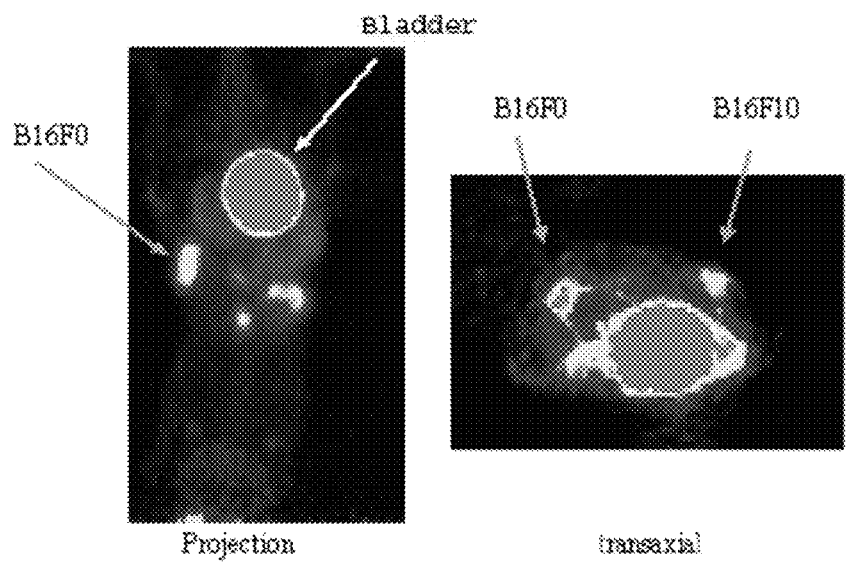
FIG. 5: In vivo PET imaging of compound [$^{18}$F]10 in a B16F0 and B16F10 melanoma-bearing C57B16 mouse from SET 1.
Figure 6:
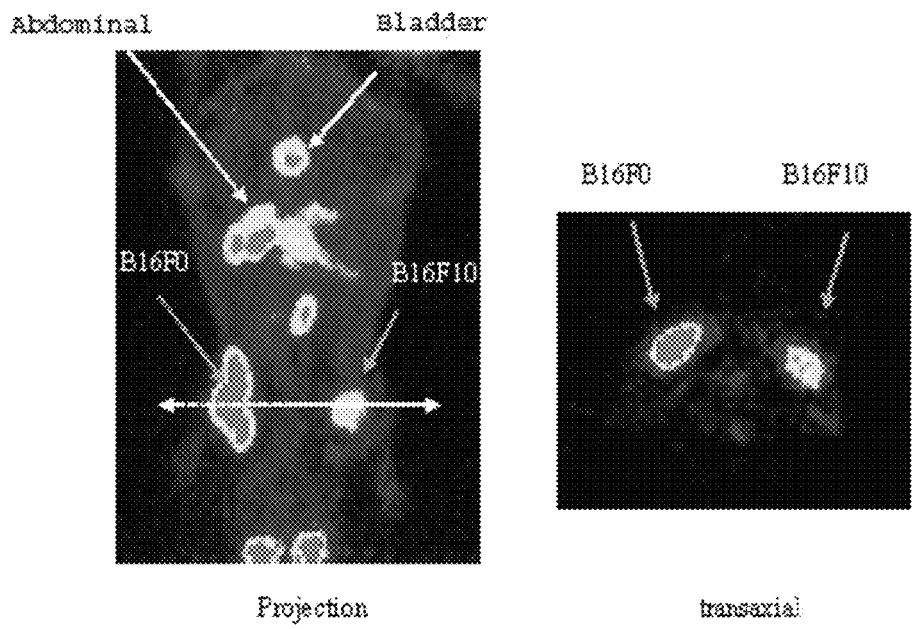
FIG. 6: In vivo PET imaging of compound [$^{18}$F]10 in a B16F0 and B16F10 melanoma-bearing C57B16 mouse from SET 3.
Figure 7:
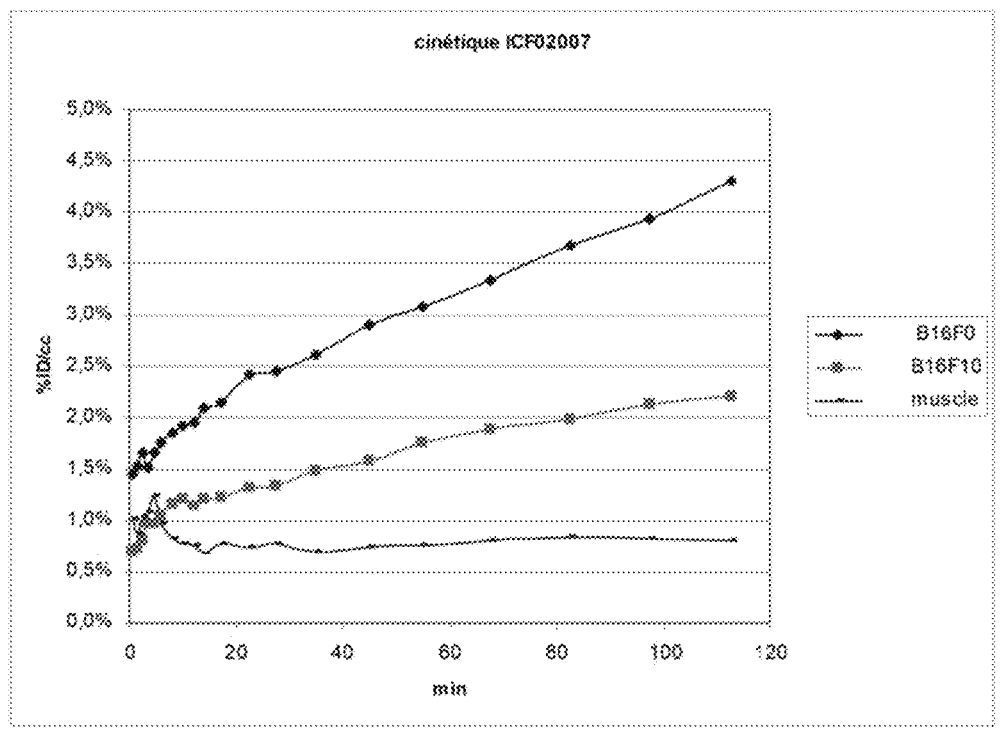
FIG. 7: time activity curves generated from dynamic PET images of [$^{18}$F]10 (also called [$^{18}$F]ICF02007) in a B16F0 and B16F10 melanoma-bearing C57B16 mouse from SET 2.
Figure 8:
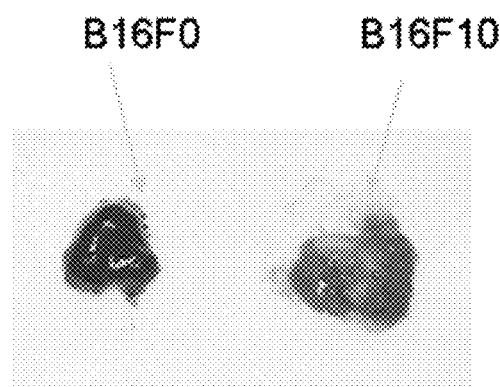
FIG. 8: Illustration of the pigmentation difference between B16F0 and B16F10 tumor specimens obtained from mice subcutaneously grafted with these two cell lines.

PET Imaging. The organs' pharmacokinetics were extracted by manual segmentation of PET images into volumes of interest (VOI) drawn using Anatomist software and covering major organs and tumour grafts. Mean Time Activity Curves (TACs) was then extracted from each organ's VOI and plotted using Excel software. All values of radioactivity concentrations were normalized for radioactivity decay, as well as by the injected dose of radiotracer, and expressed as percentage of the injected dose per volume of tissue (% ID/cc). The analysis of the PET images showed evident contrast between the B16F0 and B16F10 murine melanoma grafts and the surrounding tissue as a consequence of increased uptake of the radiolabelled compound [$^{18}$F]10 in the tumour grafts two and two-and-a-half hours post injection (FIG. 5 from a mouse of Set 1) as well as between six and six-and-a-half hours after radiotracer injection (FIG. 6 from the mouse of Set 3). This contrast is a consequence of the differences in the levels of uptake of [$^{18}$F]10 between B16F10 or B16F0 murine melanoma tumour grafts melanoma and normal tissue, as demonstrated by the results of [$^{18}$F]10 kinetics from the dynamic acquisition of PET data in mice of Set 2 presented in FIG. 7 in annex. Interestingly, there was a clear difference in the uptake of [$^{18}$F]10 between the B16F10 and the B16F0 murine melanoma grafts. At 2 and 4 hours post injection, uptake expressed as a percentage of injected dose per volume tumour graft was more than two-to-three times higher in B16F0 than in B6F10 tumour grafts implanted in the same animal (see FIGS. 5 and 6). The difference in the levels of uptake of [$^{18}$F]10 correlated with the level of concentration of melanin in the two tumour types (see FIG. 8 in annex). Using standard melanine dosage techniques (at 400 nm with a standard curve realised with commercial melanine) it was shown that B16F0 contains five times more melanine than B16F10. This is reflected in the two-to-three times higher uptake of [$^{18}$F]10 in B16F0 with respect to B16F10 as shown in FIG. 7.

The previous results show that the compounds of the present invention can be used for the diagnosis with SPECT or PET imaging and/or the treatment of melanoma by targeted radionuclide therapy.

According to one of its aspects, the present invention relates to the use of an effective amount of a compound of formulae (I), (Ia), (Ib), (Ic) or (Id) or one of its pharmaceutically acceptable salts for the preparation of a composition for the diagnosis and/or the treatment of melanoma.

According to another aspect, the present invention relates to compounds of formulae (I), (Ia), (Ib), (Ic) or (Id) or one of its pharmaceutically acceptable salts as radiopharmaceutical and/or imaging agent for the diagnosis and/or the treatment of melanoma.

According to another of its aspects, the present invention relates to a method for the diagnosis and/or the treatment of melanoma wherein it comprises at least one step of administration to a patient suffering from melanoma or potentially suffering from melanoma of an effective amount of a compound of formulae (I), (Ia), (Ib), (Ic) or (Id) or one of its pharmaceutically acceptable salts, said compound being beforehand radiolabelled.

According to another of its aspects, the present invention relates to a radiopharmaceutical composition comprising a radiolabelled compound of formulae (I), (Ia), (Ib), (Ic) or (Id). The radiolabelling occurs in particular by means of a radionuclide as described above.

According to another of its aspects, the present invention relates to a radiopharmaceutical composition comprising, as active principle, a compound of formulae (I), (Ia), (Ib), (Ic) or (Id) according to the invention, wherein it comprises a fluorine-18 atom or one of its pharmaceutically acceptable salts.

The said radiopharmaceutical composition advantageously comprises an effective amount of such a compound of formulae (I), (Ia), (Ib), (Ic) or (Id), wherein it comprises a fluorine-18 atom, and also one or more excipients. Such excipients are chosen according to the type of formulation.

The present invention furthermore relates to the use of a compound of formulae (I), (Ia), (Ib), (Ic) or (Id) or one of its pharmaceutically acceptable salts for the preparation of a radiopharmaceutical composition intended for medical imaging, more particularly for the diagnosis of melanoma.

According to another aspect, the present invention relates to compounds of formulae (I), (Ia), (Ib), (Ic) or (Id) or one of its pharmaceutically acceptable salts as medical imaging agents, more particularly for the diagnosis of melanoma.

Another aspect of the present invention pertains to a method of PET imaging which employs a fluorine-18 radiolabelled compound of formulae (I), (Ia), (Ib), (Ic) or (Id) as described above.

The patient/subject may be an animal, mammal or human.

According to one aspect, the present invention relates to the method of imaging comprising the following steps:
introducing the radiolabelled compound of formulae (I), (Ia), (Ib), (Ic) or (Id) into a subject,
imaging a part or the whole body of the subject.

A subject-matter of the present invention is a noninvasive method for the determination of the tissue distribution of tumour cells of melanoma on the human body, comprising the stages of at least one injection of a radiopharmaceutical composition comprising at least one compound of formulae (I), (Ia), (Ib), (Ic) or (Id), wherein it comprises a fluorine-18 atom, or one of its pharmaceutically acceptable salts and of at least one determination of the concentration of the radioactivity.

Methods of PET imaging are well known to the man skilled in the art.

Likewise, the present invention relates to the use of a compound of formulae (I), (Ia), (Ib), (Ic) or (Id) or one of its pharmaceutically acceptable salts for the preparation of a radiopharmaceutical composition intended for the treatment of melanoma.

According to another aspect, the present invention relates to compounds of formulae (I), (Ia), (Ib), (Ic) or (Id) or one of its pharmaceutically acceptable salts as radiopharmaceutical compounds for the treatment of melanoma.

The present invention, according to another of its aspects, relates to a method for the treatment of melanoma which comprises the administration to a patient suffering from melanoma and more particularly from disseminated melanoma of an effective amount of a compound of formulae (I), (Ia), (Ib), (Ic) or (Id), wherein it comprises a iodine-131 atom, or one of its pharmaceutically acceptable salts.

Another aspect of the invention pertains to the use of an unlabelled compound of formulae (I), (Ia), (Ib), (Ic) or (Id) as described above and an alkaline radioactive halide in the manufacture of a medicament for the use in the diagnosis and/or the treatment of melanoma.

According to another aspect, the present invention relates to unlabelled compounds of formulae (I), (Ia), (Ib), (Ic) or (Id) or one of its pharmaceutically acceptable salts for use, when combined with an alkaline radioactive halide, as radiopharmaceutical and/or imaging agent for the diagnosis and/or the treatment of melanoma.

According to another aspect, the present invention relates to a method of treatment of melanoma comprising a step of imaging with a radiolabelled compound of formulae (I), (Ia), (Ib), (Ic) or (Id) by fluorine-18 PET for diagnosis of melanoma lesions allowing, in a subject, a staging of the disease and then by treating said melanoma lesions, for example by injecting a compound of formulae (I), (Ia), (Ib), (Ic) or (Id) which can be radiolabelled by iodine-131, astatine-211 or iodine-125, in particular denoting the same chemical structure with the exception of labelling, and following the evolution of the melanoma and the efficacy of the treatment by one or more successive imaging steps by fluorine-18 PET imaging. Indeed the fluorine-18 PET imaging allows a quantization of radioactivity present in the tumor, which is of particular interest to dosimetry studies in order to evaluate and adjust the therapeutic treatment of melanoma.

According to a particular aspect, the chemical structure for the imaging and the treatment is identical, except with respect to labelling, which is carried out on demand for each specific application.

The radiolabelled compound according to the present invention may be administered to a subject/patient by any convenient route of administration, whether systemically/peripherally or topically.

The invention claimed is:
1. A compound of formula (Ic)

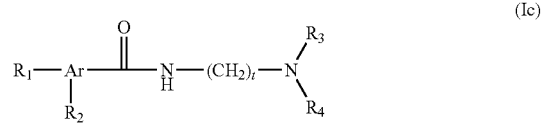

(Ic)

in which
Ar is pyridyl, quinolyl, isoquinolyl, quinoxalinyl, acridinyl, acridonyl, phenazinyl, naphthyl, naphthyridinyl or imidazopyridyl,
$R_1$ is a iodine atom or a labelled iodine atom,
$R_2$ represents a hydrogen atom, a $(C_1-C_4)$alkyl, a $(C_1-C_4)$ alkoxy group, a halogen, a labelled halogen, an —SH group, an —OH group, an —$NR_5R_6$ group or a —$N^+R_5R_6R_7X^-$ group, wherein $X^-$ is monovalent anion and $R_5$, $R_6$ and $R_7$ independently represent a hydrogen atom or a $(C_1-C_4)$alkyl group,
t is an integer ranging from 2 to 4,
$R_3$ and $R_4$ represent the formula (φ)

—$(CH_2)_q$-T-$(CH_2)_r$—$R_{15}$   (φ)

wherein
q and r are integers independently ranging from 0 to 4,
T represents a bond, a $(C_1-C_4)$alkylene group, a $(C_2-C_{10})$ alkenylene group, a $(C_2-C_{10})$alkynylene group, —O—, —NH—, —CONH— or —NHCO—, and
$R_{15}$ represents a hydrogen atom; a halogen; a labelled halogen; a radionuclide; a —$SO_2R_{12}$ group wherein $R_{12}$ is a $(C_1-C_4)$alkyl group, a $(C_3-C_8)$cycloalkyl, an aryl

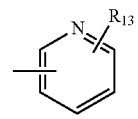

group or a heteroaryl group; or a group, wherein $R_{13}$ represents a hydrogen atom; a halogen; a labelled halogen; a radionuclide; a —$NO_2$ group; a —$NR_5R_6$ group or a —$N^+R_5R_6R_7X^-$ group, wherein $R_5$, $R_6$ and $R_7$ independently represent a hydrogen atom, a $(C_1-C_4)$alkyl group, an aryl group or an arylalkyl group and $X^-$ is a monovalent anion; and its addition salts with pharmaceutically acceptable acids; with the proviso that the compound of formula (Ic) comprises at least one fluorine atom, a labelled fluorine atom, or a precursor group selected from the group consisting of a —$NO_2$ group; a halogen with the exclusion of fluorine; a —$N^+R_5R_6R_7$- group wherein, $R_5$, $R_6$ and $R_7$, independently represent a hydrogen atom, a $(C_1-C_4)$alkyl group, an aryl group or an arylalkyl group and X- is a monovalent anion; a $OSO_2R_{12}$ group wherein $R_{12}$ is a $(C_1-C_6)$alkyl group, a $(C_3-C_8)$cycloalkyl, an aryl group or a heteroaryl group; or a —$Sn[(C_1-C_4)alkyl]_3$ group; the $R_1$—Ar group comprises at least a halogen other than a fluorine atom, a labelled halogen atom, or a radionuclide other than a labelled fluorine atom, or a precursor group selected in the group consisting of a halogen with the exclusion of fluorine; a —OSO$_2$R$_{12}$ group wherein R$_{12}$ is a (C$_1$-C$_6$) alkyl group, a (C$_3$-C$_8$)cycloalkyl, an aryl group or a heteroaryl group; or a —Sn[(C$_1$-C$_4$)alkyl]$_3$ group.

2. The compound of formula (Ic) according to claim 1, comprising at least one fluorine atom or labelled fluorine atom located in the R$_2$, R$_3$ or R$_4$ group; the R$_1$—Ar group comprises at least a halogen other than a fluorine atom, a labelled halogen atom or a radionuclide other than a labelled fluorine atom, or precursor group as defined according to claim 1.

3. The compound of formula (Ic) according to claim 1, wherein t is equal to 2.

4. The compound according to claim 1, which is:
N-[2-[N-ethyl-N-[2-(2-fluoropyridin-3-yloxy)ethyl] amino]ethyl]-6-iodoquinoxaline-2-carboxamide (10),
N-[2-[N-ethyl-N-[2-[(6-fluoropyridin-2-yl)amino]ethyl] amino]ethyl]-6-iodoquinoxaline-2-carboxamide (16),
N-[2-[[N-ethyl-N-(6-fluoropyridin-2-yl)]amino]ethyl]-6-iodoquinoxaline-2-carboxamide (20),
N-[2-[[N-ethyl-N-(2-fluoroethyl)]amino]ethyl]-6-iodoquinoxaline-2-carboxamide (25),
N-[2-[[N-ethyl-N-(2-fluoropyridin-4-yl)methyl]amino] ethyl]-6-iodoquinoxaline-2-carboxamide (33),
N-[2-[N-ethyl-N-[2-[[(2-fluoropyridin-4-yl)carbonyl] amino]ethyl]amino]ethyl]-6-iodoquinoxaline-2-carboxamide (39),
N-[2-[[N-ethyl-N-2-(2-fluoropyridin-4-yl)ethyl]amino] ethyl]-6-iodoquinoxaline-2-carboxamide (46),
N-[2-[[N-ethyl-N-3-(2-fluoropyridin-4-yl)propyl]amino] ethyl]-6-iodoquinoxaline-2-carboxamide (52),
N-[2-[N-ethyl-N-((E)-4-fluorobut-2-enyl)]amino]ethyl]-6-iodoquinoxaline-2-carboxamide (56)
N-[2-[N-ethyl-N-[2-(2-nitropyridin-3-yloxy)ethyl] amino]ethyl]-6-iodoquinoxaline-2-carboxamide (60)
N-[2-[N-[2-[(6-bromopyridin-2-yl)amino]ethyl]-N-(ethyl)amino]ethyl]-6-iodoquinoxaline-2-carboxamide (63)
N-[2-[N-ethyl-N-[2-(2-fluoropyridin-3-yloxy)ethyl] amino]ethyl]-6-iodoquinoline-2-carboxamide (67)
N-[2-[N-ethyl-N-[2-(2-fluoropyridin-3-yloxy)ethyl] amino]ethyl]-6-iodonaphthalene-2-carboxamide (70)
N-[2-[N-ethyl-N-[2-(2-fluoropyridin-3-yloxy)ethyl] amino]ethyl]-8-iodo-[1,6]naphthyridine-2-carboxamide (73)
N-[2-[N-ethyl-N-[2-(2-fluoropyridin-3-yloxy)ethyl] amino]ethyl]-6-iodoimidazo[1,2-α]pyridine-2-carboxamide (76)
N-[2-[N-ethyl-N-[2-(2-fluoropyridin-3-yloxy)ethyl] amino]ethyl]-7-iodoacridone-4-carboxamide (79)
N-[2-[N-ethyl-N-[2-(2-fluoropyridin-3-yloxy)ethyl] amino]ethyl]-7-iodophenazine-1-carboxamide (84)
N-[2-(diethylamino)ethyl]-4-fluoro-6-iodoquinoline-3-carboxamide (96)
N-[2-(diethylamino)ethyl]-4-fluoro-6-iodoquinoline-8-carboxamide (102)
N-[2-(diethylamino)ethyl]-4-fluoro-6-iodoquinoline-2-carboxamide (106)
N-[2-(diethylamino)ethyl]-2-fluoro-6-iodoquinoline-4-carboxamide (110), or
and their pharmaceutically acceptable salts.

5. A radiolabelled compound according to claim 4, comprising a radionuclide which is a radioisotope being iodine-123, iodine-124, iodine-125, iodine-131, bromine-75, bromine-76, bromine-77, fluorine-18, astatine-210 or astatine-211.

6. A radiolabelled compound according to claim 4, wherein R$_1$ is iodine-123, iodine-125 or iodine-131.

7. The compound according to claim 1, which is N-[2-[N-ethyl-N-[2-(2-fluoropyridin-3-yloxy)ethyl]amino]ethyl]-6-iodoquinoxaline-2-carboxamide (10) or its dihydrochloride salt (11).

8. A radiolabelled compound according to claim 7, wherein R$_1$ is iodine-123, iodine-125 or iodine-131.

9. A radiolabelled compound according to claim 1, comprising a radionuclide which is a radioisotope being iodine-123, iodine-124, iodine-125, iodine-131, bromine-75, bromine-76, bromine-77, fluorine-18, astatine-210 or astatine-211.

10. A radiopharmaceutical or a diagnostic composition comprising, as active principle, a radiolabelled compound or one of its pharmaceutically acceptable salts as defined according to claim 9, for the treatment and/or the diagnosis of melanoma.

11. An imaging composition comprising, as imaging agent, a radiolabelled compound or one of its pharmaceutically acceptable salts according to claim 9, for scintigraphic imaging by SPECT and by PET.

12. A radiolabelled compound according to claim 1, wherein R$_1$ is iodine-123, iodine-125 or iodine-131.

13. A radiolabelled compound according to claim 1, which is [$^{125}$I]N-[2-[N-ethyl-N-[2-(2-fluoropyridin-3-yloxy)ethyl] amino]ethyl]-6-iodoquinoxaline-2-carboxamide ([$^{125}$I]10) or its dihydrochloride salt ([$^{125}$I]11).

14. A radiolabelled compound according to claim 1, which is [$^{131}$I]N-[2-[N-ethyl-N-[2-(2-fluoropyridin-3-yloxy)ethyl] amino]ethyl]-6-iodoquinoxaline-2-carboxamide ([$^{131}$I]10) or its dihydrochloride salt ([$^{131}$I]11).

15. A radiolabelled compound according to claim 1, which is [$^{18}$F]N-[2-[N-ethyl-N-[2-(2-fluoropyridin-3-yloxy)ethyl] amino]ethyl]-6-iodoquinoxaline-2-carboxamide ([$^{18}$F]10).

* * * * *